(12) United States Patent
Nesvadba et al.

(10) Patent No.: US 7,288,613 B2
(45) Date of Patent: Oct. 30, 2007

(54) N-ALKOXY-4,4-DIOXY-POLYALKYL-PIPERIDINE COMPOUNDS, THEIR CORRESPONDING N-OXIDES AND CONTROLLED RADICAL POLYMERIZATION THEREWITH

(75) Inventors: Peter Nesvadba, Marly (CH);
Marie-Odile Zink, Mulhouse (FR);
Wiebke Wunderlich, Bologna (IT)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 0 days.

(21) Appl. No.: 11/364,537

(22) Filed: Feb. 28, 2006

(65) Prior Publication Data

US 2006/0149011 A1    Jul. 6, 2006

Related U.S. Application Data

(63) Continuation of application No. 10/450,229, filed as application No. PCT/EP01/13072 on Nov. 12, 2001, now abandoned.

(30) Foreign Application Priority Data

Dec. 14, 2000 (EP) .................................. 00811190

(51) Int. Cl.
C08F 2/38 (2006.01)
C08F 4/00 (2006.01)

(52) U.S. Cl. .................. 526/204; 526/310; 526/328; 526/329; 526/329.7; 526/346; 525/267; 525/293; 525/299; 252/183.11; 546/17; 546/18; 546/242

(58) Field of Classification Search .................. 546/17, 546/18, 242; 526/204, 310, 328, 329, 329.7, 526/346; 525/267, 293, 299; 252/183.11
See application file for complete search history.

(56) References Cited

U.S. PATENT DOCUMENTS

| | | | |
|---|---|---|---|
| 4,105,626 A | 8/1978 | Brunetti et al. | 260/45.8 |
| 4,581,429 A | 4/1986 | Solomon et al. | 526/220 |
| 6,353,107 B1 | 3/2002 | Kramer et al. | 546/216 |
| 6,479,603 B1 | 11/2002 | Yang et al. | 526/204 |
| 2003/0065184 A1 | 4/2003 | Nesvadba et al. | 546/216 |
| 2003/0216494 A1 | 11/2003 | Roth et al. | 524/95 |

FOREIGN PATENT DOCUMENTS

| | | |
|---|---|---|
| DE | 19858098 | 6/2000 |
| EP | 0574666 | 12/1993 |
| GB | 2335190 | 9/1999 |
| JP | 51-143674 | 10/1976 |

OTHER PUBLICATIONS

Derwent Abstr. 93-406779/51 for EP 0574666 (Dec. 1993).

*Primary Examiner*—Fred Teskin
(74) *Attorney, Agent, or Firm*—Tyler A. Stevenson

(57) ABSTRACT

The present invention relates to selected 1-alkoxy-2,2,6,6 tetramethyl piperidine, 1-alkoxy-2,2 diethyl-6,6 dimethyl piperidine and 1-alkoxy-2,6 diethyl-2,3,6 dimethyl piperidine derivatives which are substituted in the 4 position by two oxygen atoms forming an open chain or cyclic ketal structure, a polymerizable composition comprising a) at least one ethylenically unsaturated monomer and b) said piperidine derivatives. Further aspects of the present invention are a process for polymerizing ethylenically unsaturated monomers, and the use of 1-alkoxy-2,2,6,6 tetramethyl piperidine, 1-alkoxy-2,2 diethyl-6,6 dimethyl piperidine and 1-alkoxy-2,6 diethyl-2,3,6 dimethyl piperidine derivatives which are substituted in the 4 position by two oxygen atoms forming an open chain or cyclic ketal structure for controlled polymerization. The intermediate N-oxyl derivatives, a composition of the N-oxyl derivatives with ethylenically unsaturated monomers and a free radical initiator, as well as a process for polymerization are also subjects of the present invention.

5 Claims, No Drawings

N-ALKOXY-4,4-DIOXY-POLYALKYL-PIPERIDINE COMPOUNDS, THEIR CORRESPONDING N-OXIDES AND CONTROLLED RADICAL POLYMERIZATION THEREWITH

This is a continuation of application Ser. No. 10/450,229, filed on Jun. 11, 2003 abandoned, which is a national stage application of international app. PCT/EP 01/13072, filed Nov. 12, 2001, the disclosures of which are incorporated by reference.

The present invention relates to selected 1-alkoxy-2,2,6,6 tetramethyl piperidine, 1-alkoxy-2,2 diethyl-6,6 dimethyl piperidine and 1-alkoxy-2,6 diethyl-2,3,6 dimethyl piperidine derivatives which are substituted in the 4 position by two oxygen atoms forming an open chain or cyclic ketal structure, a polymerizable composition comprising a) at least one ethylenically unsaturated monomer and b) said piperidine derivatives. Further aspects of the present invention are a process for polymerizing ethylenically unsaturated monomers, and the use of 1-alkoxy-2,2,6,6 tetramethyl piperidine, 1-alkoxy-2,2 diethyl-6,6 dimethyl piperidine and 1-alkoxy-2,6 diethyl-2,3,6 dimethyl piperidine derivatives which are substituted in the 4 position by two oxygen atoms forming an open chain or cyclic ketal structure for controlled polymerization. The intermediate N-oxyl derivatives, a composition of the N-oxyl derivatives with ethylenically unsaturated monomers and a free radical initiator, as well as a process for polymerization are also subjects of the present invention.

The compounds of the present invention provide polymeric resin products having low polydispersity. The polymerization process proceeds with good monomer to polymer conversion efficiency. In particular, this invention relates to stable free radical-mediated polymerization processes which provide homopolymers, random copolymers, block copolymers, multiblock copolymers, graft copolymers and the like, at enhanced rates of polymerization and enhanced monomer to polymer conversions.

U.S. Pat. No. 4,581,429 to Solomon et al., issued Apr. 8, 1986, discloses a free radical polymerization process which controls the growth of polymer chains to produce short chain or oligomeric homopolymers and copolymers, including block and graft copolymers. The process employs an initiator having the formula (in part) R'R"N—O—X, where X is a free radical species capable of polymerizing unsaturated monomers. The reactions typically have low conversion rates. Specifically mentioned radical R'R"N—O. groups are derived from 1,1,3,3 tetraethylisoindoline, 1,1,3,3 tetrapropylisoindoline, 2,2,6,6 tetramethylpiperidine, 2,2,5,5 tetramethylpyrrolidine or di-t-butylamine. However, the suggested compounds do not fulfill all requirements. Particularly the polymerization of acrylates does not proceed fast enough and/or the monomer to polymer conversion is not as high as desired.

EP-A-0 574 666 describes some novel 1-oxyl-2,2,6,6 tetramethylpiperidine compounds and their preparation, which have an open chain or cyclic ketal structure in the 4 position.

U.S. Pat. No. 4,105,626 discloses also nitroxides and their preparation which are derived from 2,6-diethyl-2,6-dimethyl piperidine which have a ketal structure in 4 position.

However none of the nitroxide and nitroxylether compounds have been described as regulators/initiators for controlled radical polymerization.

GB 2335190 firstly discloses polymerization regulators/initiators on the basis of 2,2,6,6-tetraalkylpiperidine, wherein the alkyl groups have from 1 to 6 carbon atoms and at least one group is different from methyl. No specific compound having a ketal structure in the 4-position is mentioned.

It has now been found, that amongst those 2,2,6,6-tetraalkylpiperidines generically disclosed in U.S. Pat. No. 4,581,429 and GB 2335190 those are of particular value which are derivatives of 1-alkoxy-2,2,6,6 tetramethyl piperidine, 1-alkoxy-2,2 diethyl-6,6 dimethyl piperidine and of 1-alkoxy-2,6 diethyl-2,3,6 dimethyl piperidine which are substituted in the 4 position by two oxygen atoms forming an open chain or cyclic ketal structure.

The ketal structure in 4 position ensures high thermal stability which is important for storage, particularly at elevated temperatures. The ketal structure is thermally significantly more stable compared to the corresponding 4-oxo compound.

The compounds exhibit an unchanged initiating/regulating activity even after storage at elevated temperatures as for example used in conventional stability tests.

Another problem associated with nitroxyl or nitroxylether mediated free radical polymerization is the formation of a significant color of the resulting polymer. The compounds of the present invention which have a ketal structure in 4-position impart significantly less color to the polymer compared to other prior art compounds of similar structure.

The steric hindrance introduced by the two ethyl groups instead of two methyl groups further leads to an increased initiating activity and control of polymerization.

The particular substitution pattern in 2 and 6 position of the piperidine ring allows high monomer to polymer conversions in short times and low polydispersities which are generally below 2. High monomer to polymer conversions are even achieved with acrylates, such as ethyl- or butyl-acrylate. The temperature necessary to achieve high conversion in short times may be for example as low as 120° C.

One subject of the present invention is a polymerizable composition, comprising a) at least one ethylenically unsaturated monomer or oligomer, and b) a compound of formula Ia, IIa or IIIa

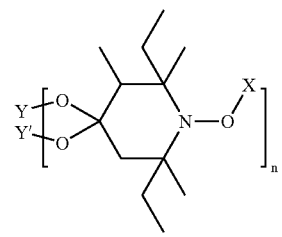

(Ia)

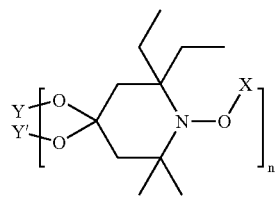

(IIa)

-continued

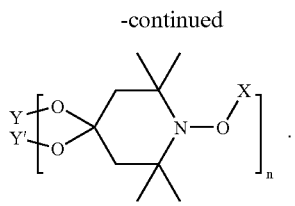
(IIIa)

wherein n is 1 or 2;

X is selected from the group consisting of —CH$_2$-phenyl, CH$_3$CH-phenyl, (CH$_3$)$_2$C-phenyl, (C$_5$-C$_6$cycloalkyl)$_2$CCN, (CH$_3$)$_2$CCN, —CH$_2$CH=CH$_2$, CH$_3$CH—CH=CH$_2$, 3-cyclohexenyl, 3-cyclopentenyl, (C$_1$-C$_4$alkyl)CR$_{20}$—C(O)-phenyl, (C$_1$-C$_4$)alkyl-CR$_{20}$—C(O)—(C$_1$-C$_4$)alkoxy, (C$_1$-C$_4$)alkyl-CR$_{20}$—C(O)—(C$_1$-C$_4$)alkyl, (C$_1$-C$_4$)alkyl-CR$_{20}$—C(O)—N-di(C$_1$-C$_4$)alkyl, (C$_1$-C$_4$)alkyl-CR$_{20}$—C(O)—NH(C$_1$-C$_4$)alkyl, (C$_1$-C$_4$)alkyl-CR$_{20}$—C(O)—NH$_2$ and a group of formula

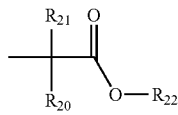

wherein R$_{20}$ is hydrogen or (C$_1$-C$_4$)alkyl, R$_{21}$ is hydrogen, C$_1$-C$_4$alkyl or phenyl and R$_{22}$ is C$_1$-C$_{12}$alkyl which is unsubstituted or substituted by OH or N(R$_{20}$)(R$_{21}$) or which is interrupted by O or NR$_{20}$;

if n is 1

Y and Y' are independently C$_1$-C$_{12}$alkyl, C$_3$-C$_{12}$alkenyl, C$_3$-C$_{12}$alkinyl, C$_5$-C$_8$cycloalkyl, phenyl, naphthyl, C$_7$-C$_9$phenylalkyl; or Y and Y' together form one of the bivalent groups —C(R$_1$)(R$_2$)—CH(R$_3$)—, CH(R$_1$)—CH$_2$—C(R$_2$)(R$_3$)—, —CH(R$_2$)—CH$_2$—C(R$_1$)(R$_3$)—, —CH$_2$—C(R$_1$)(R$_2$)—CH(R$_3$)—, o-phenylene, 1,2-cyclohexyliden, —CH$_2$—CH=CH—CH$_2$— or

wherein

R$_1$ is hydrogen, C$_1$-C$_{12}$alkyl, COOH, COO—(C$_1$-C$_{12}$)alkyl or CH$_2$OR$_4$;

R$_2$ and R$_3$ are independently hydrogen, methyl ethyl, COOH or COO—(C$_1$-C$_{12}$)alkyl;

R$_4$ is hydrogen, C$_1$-C$_{12}$alkyl, benzyl, or a monovalent acyl residue derived from an aliphatic, cycloaliphatic or aromatic monocarboxylic acid having up to 18 carbon atoms;

if n is 2

Y and Y' together form one of the tetravalent groups

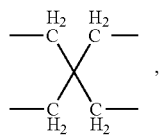

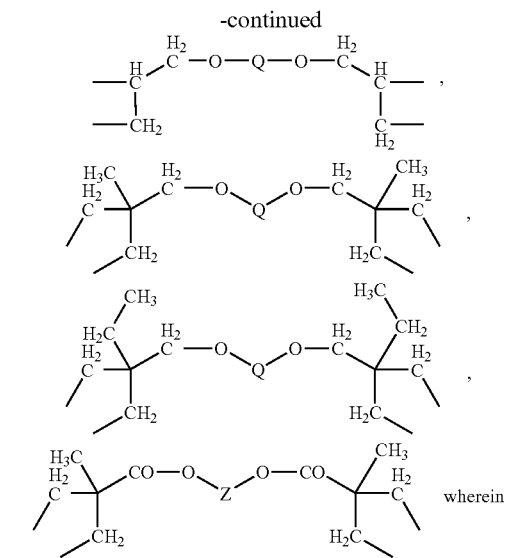

Q is a bisacyl residue which is derived from a C$_2$-C$_{12}$dicarboxylic acid or C$_1$-C$_{12}$alkylene; and Z is C$_1$-C$_{12}$alkylene.

Preferred is a polymerizable composition wherein the compound is of formula Ia or IIa.

C$_1$-C$_{12}$alkyl can be linear or branched. Examples are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl or dodecyl.

Alkenyl having from 3 to 12 carbon atoms is a branched or unbranched radical, for example propenyl, 2-butenyl, 3-butenyl, isobutenyl, n-2,4-pentadienyl, 3-methyl-2-butenyl, n-2-octenyl, n-2-dodecenyl, isododecenyl.

Alkenyl having from 3 to 25 carbon atoms is a branched or unbranched radical, for example propinyl (—CH$_2$—C≡CH), 2-butinyl, 3-butinyl, n-2-octinyl or n-2-dodecenyl.

Examples of alkoxy are methoxy, ethoxy, propoxy, isopropoxy, butoxy, isobutoxy, pentoxy, isopentoxy, hexoxy, heptoxy or octoxy.

C$_7$-C$_9$phenylalkyl is for example benzyl, α-methylbenzyl, α,α-dimethylbenzyl or 2-phenylethyl, benzyl is preferred.

C$_1$-C$_{12}$alkylene is a branched or unbranched radical, for example methylene, ethylene, propylene, trimethylene, tetramethylene, pentamethylene, hexamethylene, heptamethylene, octamethylene, decamethylene or dodecamethylene.

C$_5$-C$_8$cycloalkyl is for example cyclopentyl, cyclohexyl, cycloheptyl, methylcyclopentyl or cyclooctyl.

Examples of a monocarboxylic acid having up to 18 carbon atoms are formic acid, acetic acid, propionic acid, the isomers of valeric acid, methyl ethyl acetic acid, trimethyl acetic acid, capronic acid, lauric acid or stearic acid. Examples for unsaturated aliphatic acids are acrylic acid, methacrylic acid, crotonic acid, linolic acid and oleic acid.

Typical examples of cycloaliphatic carboxylic acids are cyclohexane carboxylic acid or cyclopentane carboxylic acid.

Examples of aromatic carboxylic acids are benzoic acid, salicylic acid or cinnamic acid.

Examples of dicarboxylic acids are oxalic acid, malonic acid, succinic acidglutaric acid adipic acid, sebatic acid, fumaric acid, maleic acid, phthalic acid, isophthalic acid, terephthalic acid.

Preferred is a polymerizable composition wherein in the compound of formula Ia, IIa or IIIa X is selected from the group consisting of —CH$_2$-phenyl, CH$_3$CH-phenyl, (CH$_3$)$_2$C-phenyl, (C$_5$-C$_6$cycloalkyl)$_2$CCN, (CH$_3$)$_2$CCN, 3-cyclohexenyl and the other substituents are as defined above, most preferably X is CH$_3$CH-phenyl.

Also preferred is a polymerizable composition wherein in the compound of formula Ia, IIa or IIIa X is selected from the group consisting of —CH$_2$-phenyl, CH$_3$CH-phenyl, (CH$_3$)$_2$C-phenyl, (C$_5$-C$_6$cycloalkyl)$_2$CCN, (CH$_3$)$_2$CCN, 3-cyclohexenyl;

n is 1

Y and Y' are independently C$_1$-C$_{12}$alkyl, C$_3$-C$_{12}$alkenyl, C$_3$-C$_{12}$alkinyl, C$_5$-C$_8$cycloalkyl, phenyl, naphthyl, C$_7$-C$_9$phenylalkyl; or Y and Y' together form one of the bivalent groups —C(R$_1$)(R$_2$)—CH(R$_3$)—, CH(R$_1$)—CH$_2$—C(R$_2$)(R$_3$)—, —CH(R$_2$)—CH$_2$—C(R$_1$)(R$_3$)—, —CH$_2$—C(R$_1$)(R$_2$)—CH(R$_3$)—, o-phenylene, 1,2-cyclohexyliden, —CH$_2$—CH═CH—CH$_2$— or

;

wherein

R$_1$ is hydrogen, C$_1$-C$_{12}$alkyl, COOH, COO—(C$_1$-C$_{12}$)alkyl or CH$_2$OR$_4$;

R$_2$ and R$_3$ are independently hydrogen, methyl ethyl, COOH or COO—(C$_1$-C$_{12}$)alkyl;

R$_4$ is hydrogen, C$_1$-C$_{12}$alkyl, benzyl, or a monovalent acyl residue derived from an aliphatic, cycloaliphatic or aromatic monocarboxylic acid having up to 18 carbon atoms.

More preferred is a polymerizable composition wherein in the compound of formula Ia, IIa or IIIa X is CH$_3$CH-phenyl;

n is 1

Y and Y' are independently C$_1$-C$_{12}$alkyl, C$_3$-C$_{12}$alkenyl, phenyl or benzyl; or Y and Y' together form one of the bivalent groups —C(R$_1$)(R$_2$)—CH(R$_3$)—, CH(R$_1$)—CH$_2$—C(R$_2$)(R$_3$)—, —CH(R$_2$)—CH$_2$—C(R$_1$)(R$_3$)—, —CH$_2$—C(R$_1$)(R$_2$)—CH(R$_3$)—, —CH$_2$—CH═CH—CH$_2$— or; wherein R$_1$ is hydrogen, C$_1$-C$_{12}$alkyl, COO—(C$_1$-C$_{12}$)alkyl or CH$_2$OR$_4$;

R$_2$ and R$_3$ are independently hydrogen, methyl ethyl, or COO—(C$_1$-C$_{12}$)alkyl;

R$_4$ is hydrogen, C$_1$-C$_{12}$alkyl, benzyl, or a monovalent acyl residue derived from an aliphatic, cycloaliphatic or aromatic monocarboxylic acid having up to 12 carbon atoms.

Most suitable individual compounds are given in Tables 1, 2 and 3

TABLE 1

Compounds according to formula (Ia)

| | |
|---|---|
| 1 | 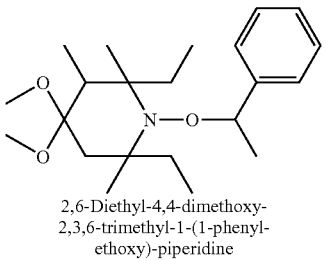<br>2,6-Diethyl-4,4-dimethoxy-2,3,6-trimethyl-1-(1-phenyl-ethoxy)-piperidine |
| 2 | 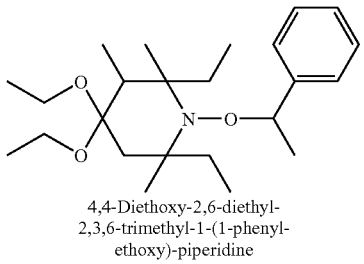<br>4,4-Diethoxy-2,6-diethyl-2,3,6-trimethyl-1-(1-phenyl-ethoxy)-piperidine |
| 3 | 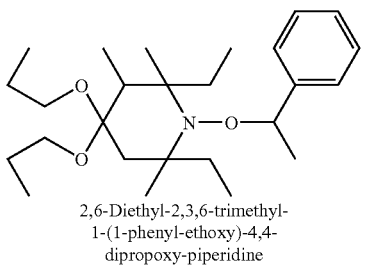<br>2,6-Diethyl-2,3,6-trimethyl-1-(1-phenyl-ethoxy)-4,4-dipropoxy-piperidine |

TABLE 1-continued
Compounds according to formula (Ia)
4
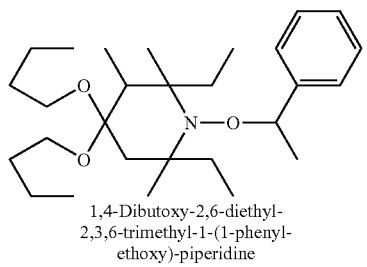
1,4-Dibutoxy-2,6-diethyl-
2,3,6-trimethyl-1-(1-phenyl-
ethoxy)-piperidine
5
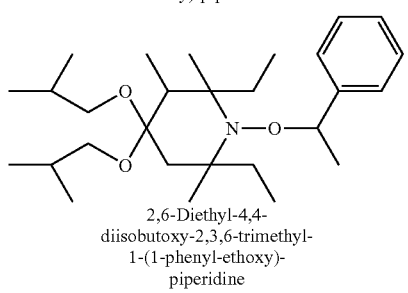
2,6-Diethyl-4,4-
diisobutoxy-2,3,6-trimethyl-
1-(1-phenyl-ethoxy)-
piperidine
6
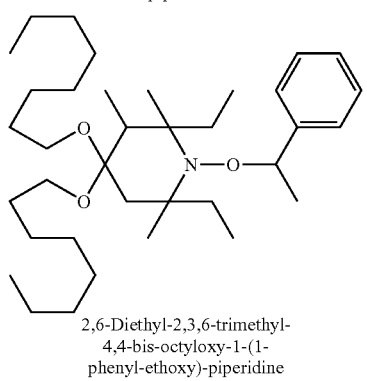
2,6-Diethyl-2,3,6-trimethyl-
4,4-bis-octyloxy-1-(1-
phenyl-ethoxy)-piperidine
7
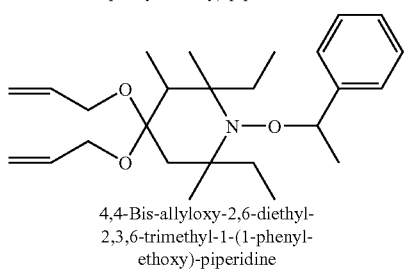
4,4-Bis-allyloxy-2,6-diethyl-
2,3,6-trimethyl-1-(1-phenyl-
ethoxy)-piperidine
8
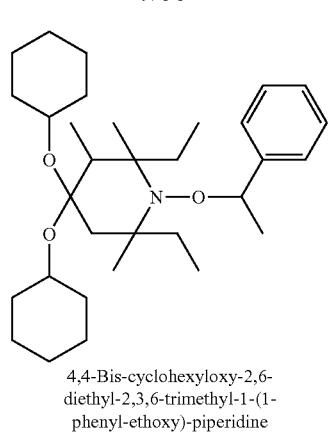
4,4-Bis-cyclohexyloxy-2,6-
diethyl-2,3,6-trimethyl-1-(1-
phenyl-ethoxy)-piperidine TABLE 1-continued
Compounds according to formula (Ia)
9
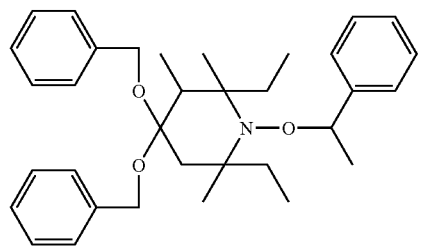
4,4-Bis-benzyloxy-2,6-
diethyl-2,3,6-trimethyl-1-(1-
phenyl-ethoxy)-piperidine
10
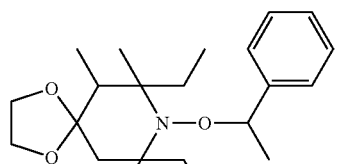
7,9-Diethyl-6,7,9-trimethyl-8-
(1-phenyl-ethoxy)-1,4-dioxa-
8-aza-spiro[4.5]decane
11
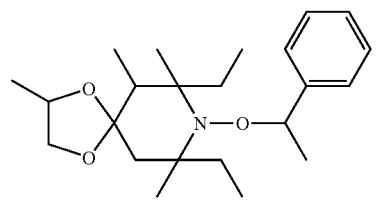
7,9-Diethyl-2,6,7,9-
tetramethyl-8-(1-phenyl-
ethoxy)-1,4-dioxa-8-aza-
spiro[4.5]decane
12
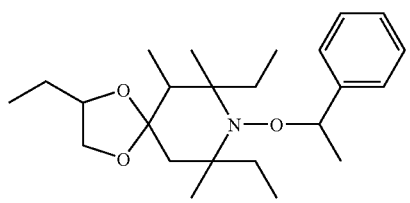
2,7,9-Triethyl-6,7,9-
trimethyl-8-(1-phenyl-
ethoxy)-1,4-dioxa-8-aza-
spiro[4.5]decane
13
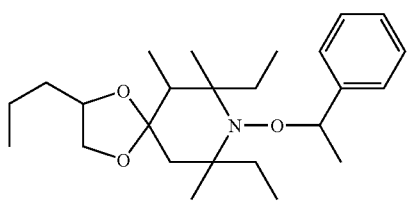
7,9-Diethyl-6,7,9-trimethyl-8-
(1-phenyl-ethoxy)-2-propyl-
1,4-dioxa-8-aza-
spiro[4.5]decane TABLE 1-continued Compounds according to formula (Ia)

14 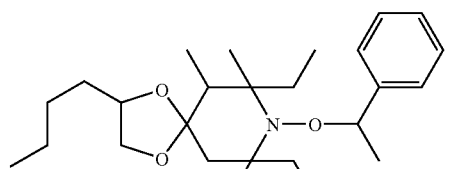

2-Butyl-7,9-diethyl-6,7,9-
trimethyl-8-(1-phenyl-
ethoxy)-1,4-dioxa-8-aza-
spiro[4.5]decane 15 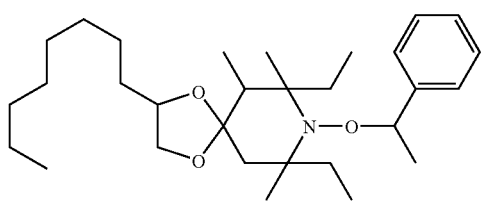

7,9-Diethyl-6,7,9-trimethyl-
2-octyl-8-(1-phenyl-
ethoxy)-1,4-dioxa-8-aza-
spiro[4.5]decane 16 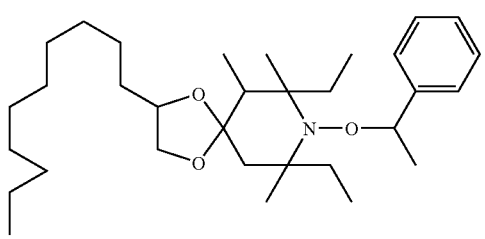

2-Decyl-7,9-diethyl-6,7,9-
trimethyl-8-(1-phenyl-
ethoxy)-1,4-dioxa-8-aza-
spiro[4.5]decane 17 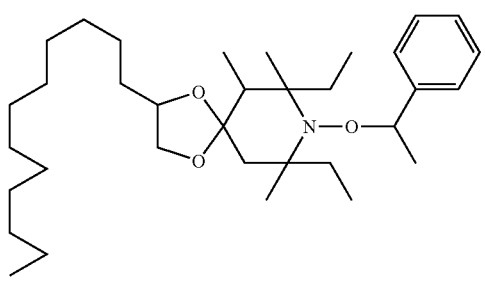

2-Dodecyl-7,9-diethyl-
6,7,9-trimethyl-8-(1-phenyl-
ethoxy)-1,4-dioxa-8-aza-
spiro[4.5]decane 18 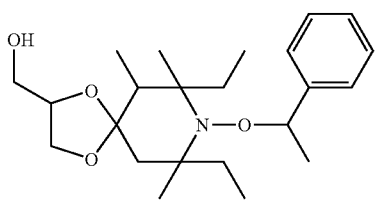

[7,9-Diethyl-6,7,9-trimethyl-
8-(1-phenyl-ethoxy)-1,4-
dioxa-8-aza-spiro[4.5]dec-
2-yl]-methanol TABLE 1-continued Compounds according to formula (Ia)

19 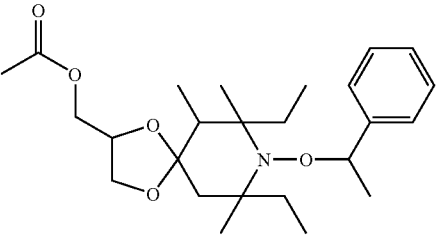

Acetic acid 7,9-diethyl-8-
hydroxy-6,7,9-trimethyl-1,4-
dioxa-8-aza-spiro[4.5]dec-2-
ylmethyl ester; compound
with isopropyl-benzene 20 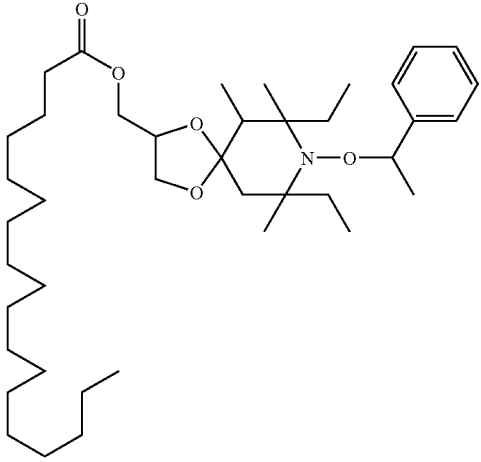

Octadecanoic acid 7,9-
diethyl-6,7,9-trimethyl-8-(1-
phenyl-ethoxy)-1,4-dioxa-
8-aza-spiro[4.5]dec-2-
ylmethyl ester 21 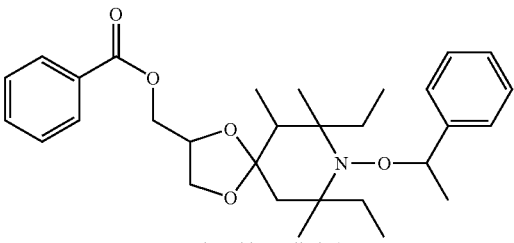

Benzoic acid 7,9-diethyl-8-
hydroxy-6,7,9-trimethyl-
1,4-dioxa-8-aza-
spiro[4.5]dec-2-ylmethyl
ester; compound with
isopropyl-benzene 22 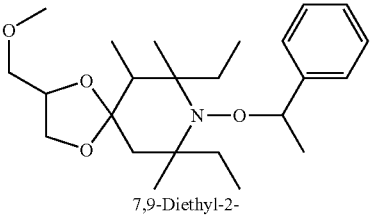

7,9-Diethyl-2-
methoxymethyl-6,7,9-
trimethyl-8-(1-phenyl-
ethoxy)-1,4-dioxa-8-aza-
spiro[4.5]decane TABLE 1-continued Compounds according to formula (Ia)

23 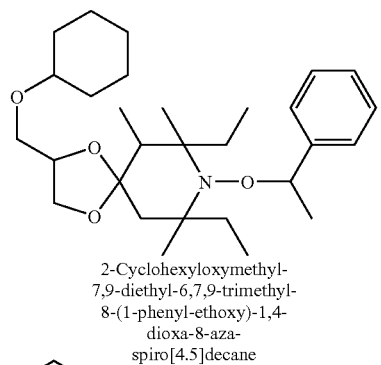

2-Cyclohexyloxymethyl-
7,9-diethyl-6,7,9-trimethyl-
8-(1-phenyl-ethoxy)-1,4-
dioxa-8-aza-
spiro[4.5]decane 24 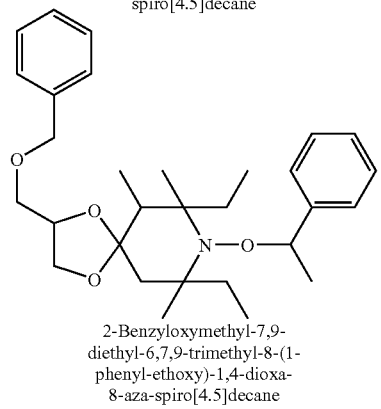

2-Benzyloxymethyl-7,9-
diethyl-6,7,9-trimethyl-8-(1-
phenyl-ethoxy)-1,4-dioxa-
8-aza-spiro[4.5]decane 25 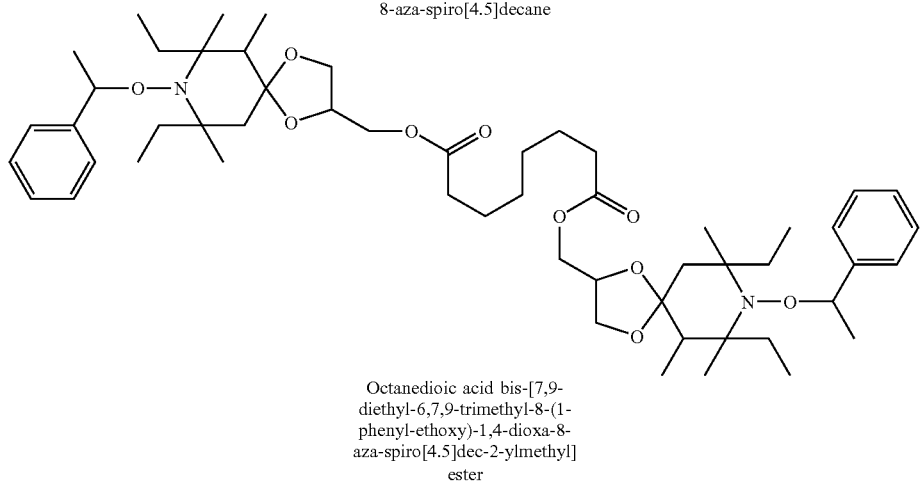

Octanedioic acid bis-[7,9-
diethyl-6,7,9-trimethyl-8-(1-
phenyl-ethoxy)-1,4-dioxa-8-
aza-spiro[4.5]dec-2-ylmethyl]
ester 26 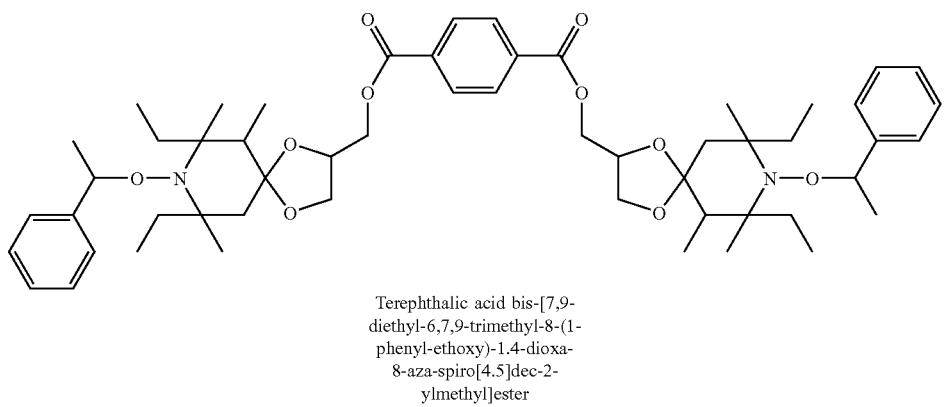

Terephthalic acid bis-[7,9-
diethyl-6,7,9-trimethyl-8-(1-
phenyl-ethoxy)-1,4-dioxa-
8-aza-spiro[4.5]dec-2-
ylmethyl]ester TABLE 1-continued Compounds according to formula (Ia)

27

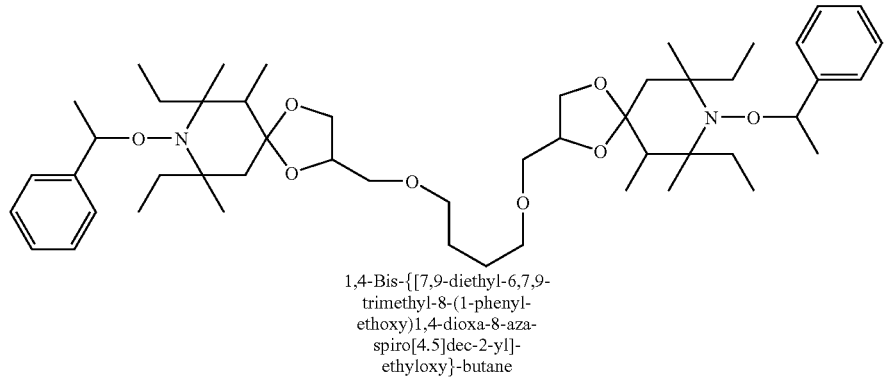

1,4-Bis-{[7,9-diethyl-6,7,9-
trimethyl-8-(1-phenyl-
ethoxy)1,4-dioxa-8-aza-
spiro[4.5]dec-2-yl]-
ethyloxy}-butane

28

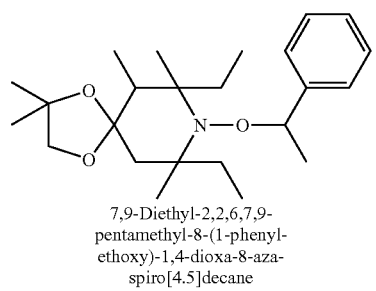

7,9-Diethyl-2,2,6,7,9-
pentamethyl-8-(1-phenyl-
ethoxy)-1,4-dioxa-8-aza-
spiro[4.5]decane

29

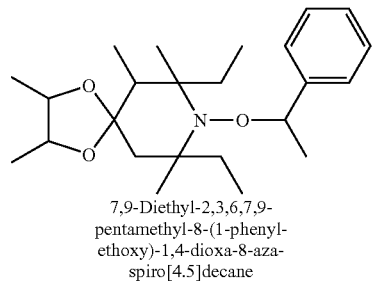

7,9-Diethyl-2,3,6,7,9-
pentamethyl-8-(1-phenyl-
ethoxy)-1,4-dioxa-8-aza-
spiro[4.5]decane

30

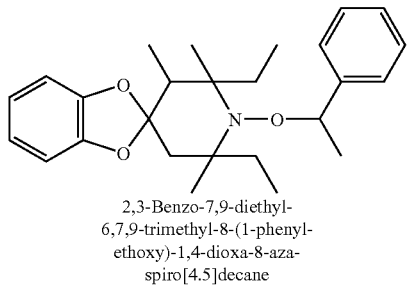

2,3-Benzo-7,9-diethyl-
6,7,9-trimethyl-8-(1-phenyl-
ethoxy)-1,4-dioxa-8-aza-
spiro[4.5]decane

31

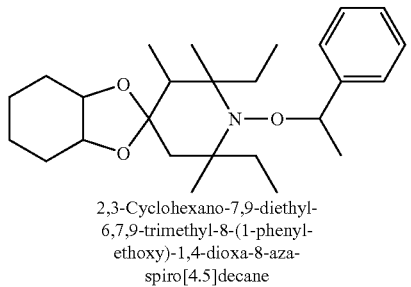

2,3-Cyclohexano-7,9-diethyl-
6,7,9-trimethyl-8-(1-phenyl-
ethoxy)-1,4-dioxa-8-aza-
spiro[4.5]decane TABLE 1-continued Compounds according to formula (Ia)

32 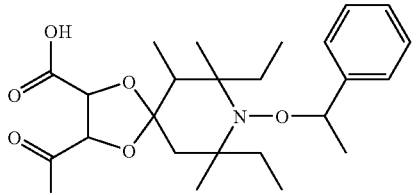

7,9-Diethyl-6,7,9-trimethyl-
8-(1-phenyl-ethoxy)-1,4-
dioxa-8-aza-
spiro[4.5]decane-2,3-
dicarboxylic acid 33 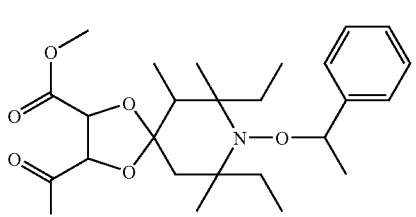

7,9-Diethyl-6,7,9-trimethyl-
8-(1-phenyl-ethoxy)-1,4-
dioxa-8-aza-
spiro[4.5]decane-2,3-
dicarboxylic acid dimethyl
ester 34 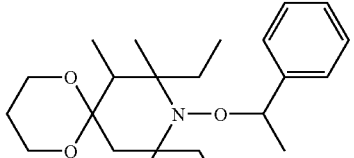

8,10-Diethyl-7,8,10-
trimethyl-9-(1-phenyl-
ethoxy)-1,5-dioxa-9-aza-
spiro[5.5]undecane 35 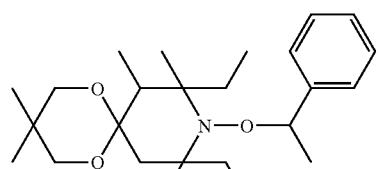

8,10-Diethyl-3,3,7,8,10-
pentamethyl-9-(1-phenyl-
ethoxy)-1,5-dioxa-9-aza-
spiro[5.5]undecane 36 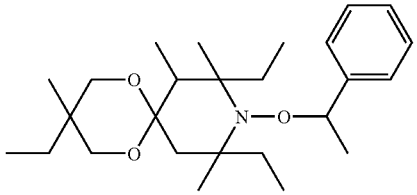

3,8,10-Triethyl-3,7,8,10-
tetramethyl-9-(1-phenyl-
ethoxy)-1,5-dioxa-9-aza-
spiro[5.5]undecane TABLE 1-continued Compounds according to formula (Ia)

37 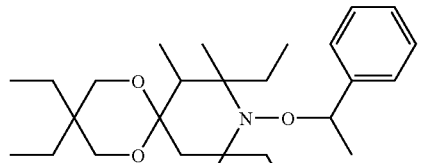

3,3,8,10-Tetraethyl-7,8,10-
trimethyl-9-(1-phenyl-
ethoxy)-1,5-dioxa-9-aza-
spiro[5.5]undecane 38 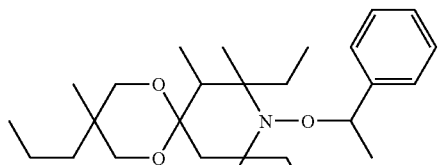

8,10-Diethyl-3,7,8,10-
tetramethyl-9-(1-phenyl-
ethoxy)-3-propyl-1,5-dioxa-
9-aza-spiro[5.5]undecane 39 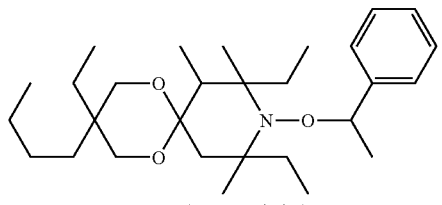

3-Butyl-3,8,10-triethyl-
7,8,10-trimethyl-9-(1-
phenyl-ethoxy)-1,5-dioxa-
9-aza-spiro[5.5]undecane 40 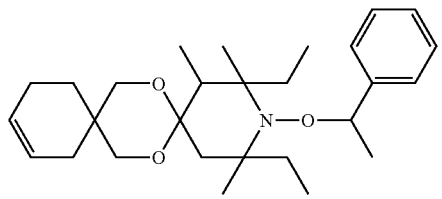

2,4-Diethyl-1,2,4-trimethyl-3-
(1-phenyl-ethoxy)-7,16-
dioxa-3-aza-
dispiro[5.2.5.2]hexadec-11-
ene 41 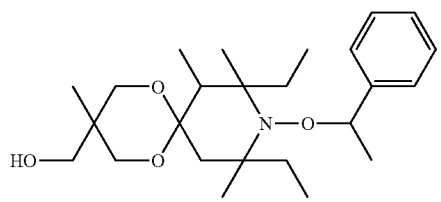

[8,10-Diethyl-3,7,8,10-
tetramethyl-9-(1-phenyl-
ethoxy)-1,5-dioxa-9-aza-
spiro[5.5]undec-3-yl]-
methanol TABLE 1-continued Compounds according to formula (Ia)

42 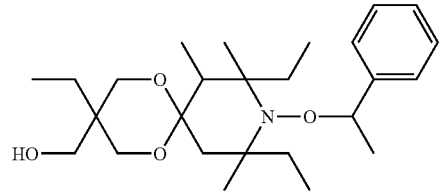

[3,8,10-Triethyl-7,8,10-
trimethyl-9-(1-phenyl
ethoxy)-1,5-dioxa-9-aza-
spiro[5.5]undec-3-yl]-
methanol 43 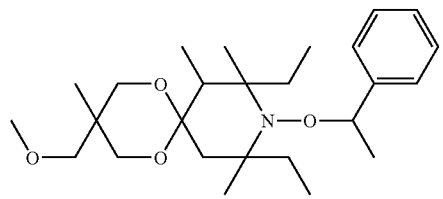

8,10-Diethyl-3-
methoxymethyl-3,7,8,10-
tetramethyl-9-(1-phenyl-
ethoxy)-1,5-dioxa-9-aza-
spiro[5.5]undecane 44 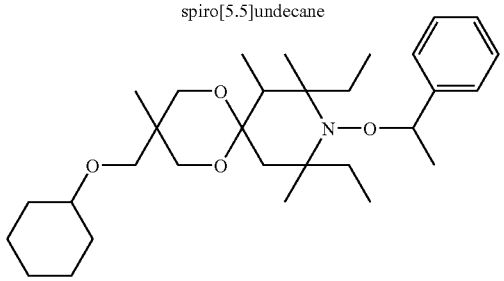

3-Cyclohexyloxymethyl-
8,10-diethyl-3,7,8,10-
tetramethyl-9-(1-phenyl-
ethoxy)-1,5-dioxa-9-aza-
spiro[5.5]undecane 45 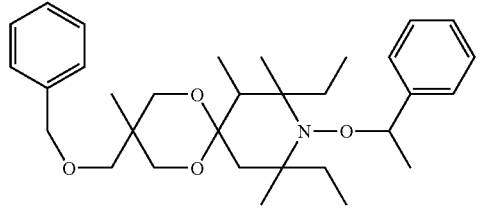

3-Benzyloxymethyl-8,10-
diethyl-3,7,8,10-
tetramethyl-9-(1-phenyl-
ethoxy)-1,5-dioxa-9-aza-
spiro[5.5]undecane 46 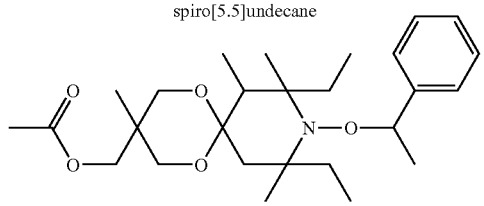

Acetic acid 8,10-diethyl-
3,7,8,10-tetramethyl-9-(1-
phenyl-ethoxy)-1,5-dioxa-9-
aza-spiro(5.5]undec-3-
ylmethyl ester TABLE 1-continued Compounds according to formula (Ia)

47

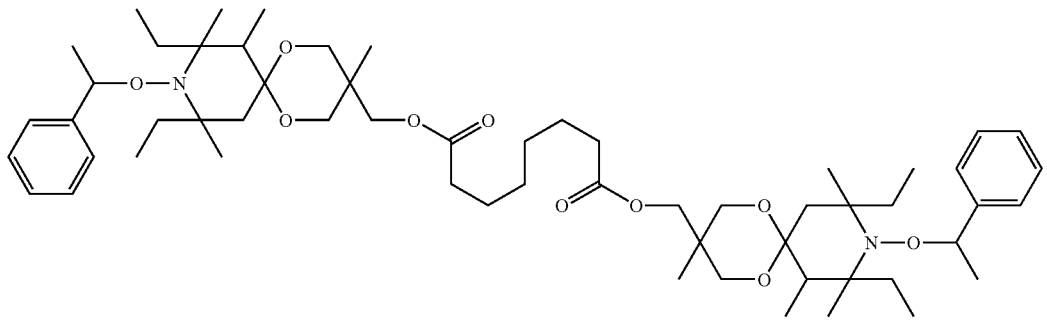

Octanedioic acid bis-[8,10-
diethyl-3,7,8,10-
tetramethyl-9-(1-phenyl-
ethoxy)-1,5-dioxa-9-aza-
spiro[5.5]undec-3-ylmethyl]
ester

48

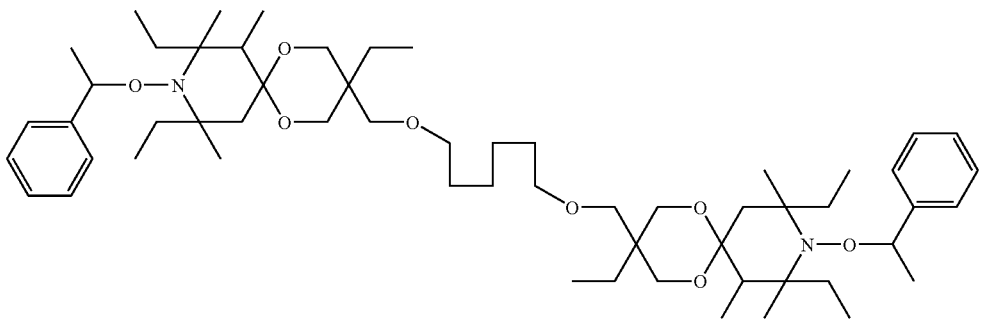

1,6-Bis-{3,8,10-triethyl-
7,8,10-trimethyl-9-(1-
phenyl-ethoxy)-1,5-dioxa-
9-aza-spiro[5.5]undec-3-
methyloxy}-hexane

49

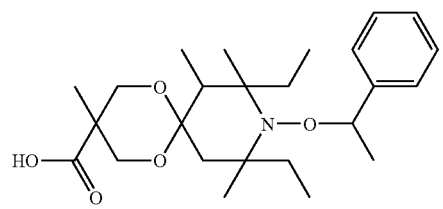

8,10-Diethyl-3,7,8,10-
tetramethyl-9-(1-phenyl-
ethoxy)-1,5-dioxa-9-aza-
spiro[5.5]undecane-3-
carboxylic acid

50

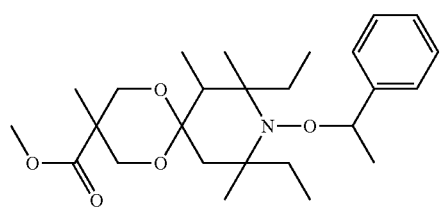

8,10-Diethyl-3,7,8,10-
tetramethyl-9-(1-phenyl-
ethoxy)-1,5-dioxa-9-aza-
spiro[5.5]undecane-3-
carboxylic acid methyl
ester TABLE 1-continued Compounds according to formula (Ia)

51 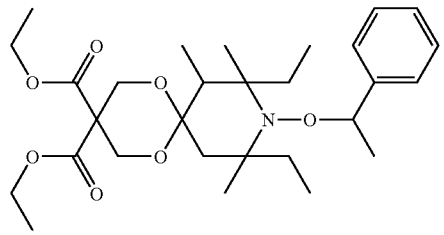

8,10-Diethyl-7,8,10-
trimethyl-9-(1-phenyl-
ethoxy)-1,5-dioxa-9-aza-
spiro[5.5]undecane-3,3-
dicarboxylic acid diethyl
ester 52 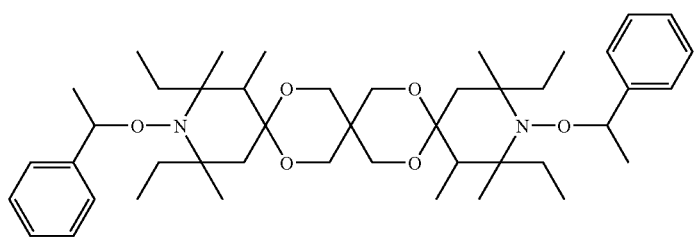

1,6-Bis-{3,8,10-triethyl-
7,8,10-trimethyl-9-(1-phenyl-
ethoxy)-1,5-dioxa-9-aza-
spiro[5.5]undec-3-
methyloxy}-hexane 53 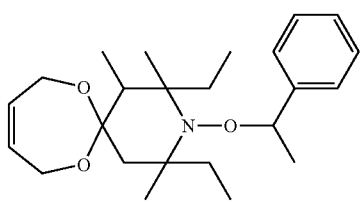

2,4-Diethyl-1,2,4-trimethyl-
3-(1-phenyl-ethoxy)-7,12-
dioxa-3-aza-
spiro[5.6]dodec-9-ene 54 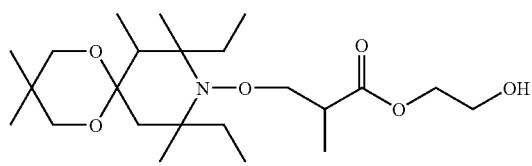

2-(8,10-Diethyl-3,3,7,8,10-
pentamethyl-1,5-dioxa-9-
aza-spiro[5.5]undec-9-
yloxy)-propionic acid 2-
hydroxy-ethyl ester TABLE 2
Compounds according to formula IIa
1
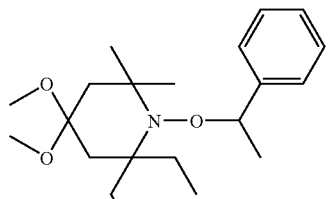
2,2-Diethyl-4,4-dimethoxy-
6,6-dimethyl-1-(1-phenyl-
ethoxy)-piperidine
2
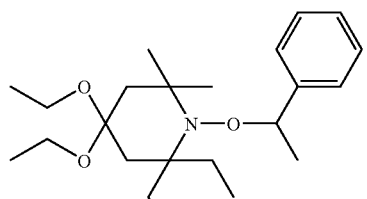
4,4-Diethoxy-2,2-diethyl-
6,6-dimethyl-1-(1-phenyl-
ethoxy)-piperidine
3
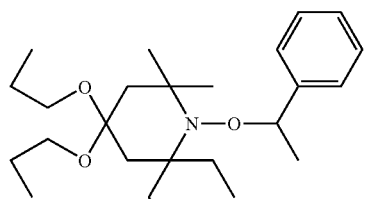
2,2-Diethyl-6,6-dimethyl-1-
(1-phenyl-ethoxy)-4,4-
dipropoxy-piperidine
4
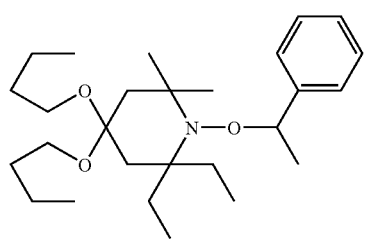
4,4-Dibutoxy-2,2-diethyl-6,6-
dimethyl-1-(1-phenyl-ethoxy)-
piperidine
5
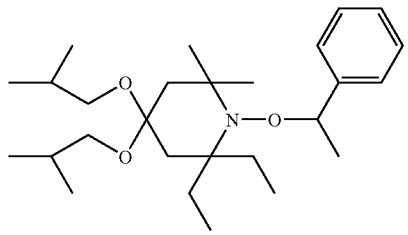
2,2-Diethyl-4,4-
diisobutoxy-6,6-dimethyl-1-
(1-phenyl-ethoxy)-
piperdine TABLE 2-continued
Compounds according to formula IIa
6
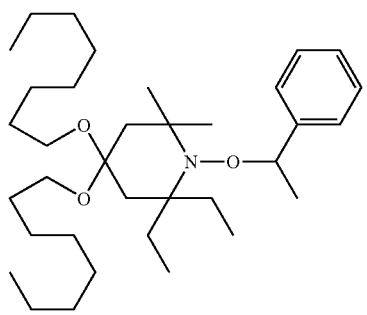
2,2-Diethyl-6,6-dimethyl-4,4-
bis-octyloxy-1-(1-phenyl-
ethoxy)-pipendine
7
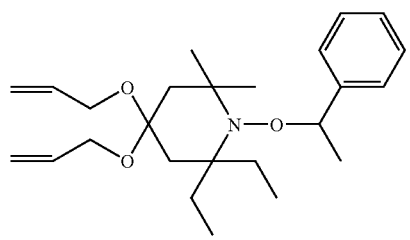
4-Bis-allyloxy-2,2-diethyl-
6,6-dimethyl-1-(1-phenyl-
ethoxy)-piperidine
8
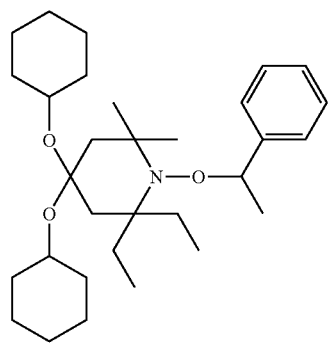
4,4-Bis-cyclohexyloxy-2,2-
diethyl-6,6-dimethyl-1-(1-
phenyl-ethoxy)-piperidine
9
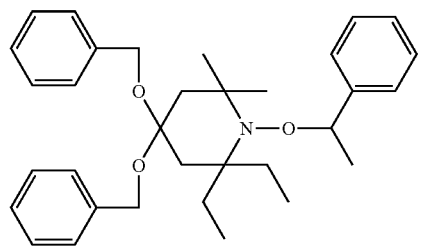
4,4-Bis-benzyloxy-2,2-
diethyl-6,6-dimethyl-1-(1-
phenyl-ethoxy)-piperidine TABLE 2-continued
Compounds according to formula IIa
10
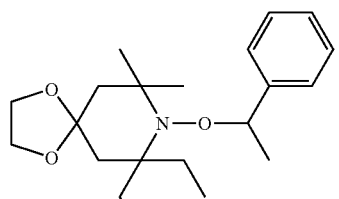
7,7-Diethyl-9,9-dimethyl-8-(1-phenyl-ethoxy)-1,4-dioxa-8-aza-spiro[4.5]decane
11
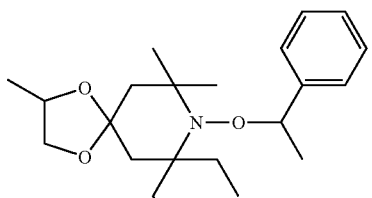
7,7-Diethyl-2,9,9-trimethyl-8-(1-phenyl-ethoxy)-1,4-dioxa-8-aza-spiro[4.5]-decane
12
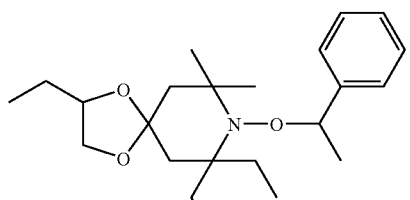
2,7,7-Triethyl-9,9-dimethyl-8-(1-phenyl-ethoxy)-1,4-dioxa-8-aza-spiro[4.5]decane
13
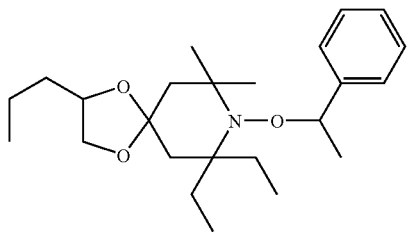
7,7-Diethyl-9,9-dimethyl-8-(1-phenyl-ethoxy)-2-propyl-1,4-dioxa-8-aza-spiro[4.5]decane
14
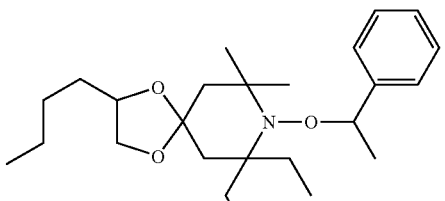
2-Butyl-7,7-diethyt-9,9-dimethyl-8-(1-phenyl-ethoxy)-1,4-dioxa-8-aza-spiro[4.5]decane TABLE 2-continued
Compounds according to formula IIa
15 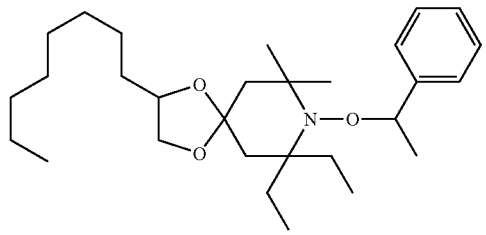
7,7-Diethyl-9,9-dimethyl-2-
octyl-8-(1-phenyl-ethoxy)-
1,4-dioxa-8-aza-
spiro[4.5]decane
16 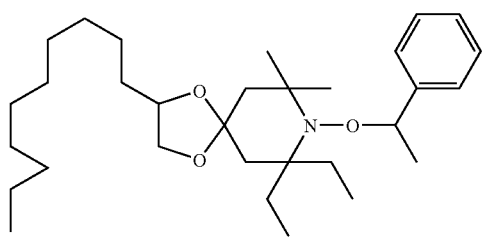
2-Decyl-7,7-diethyl-9,9-
dimethyl-8-(1-phenyl-ethoxy)-
1,4-dioxa-8-aza-
spiro[4.5]decane
17 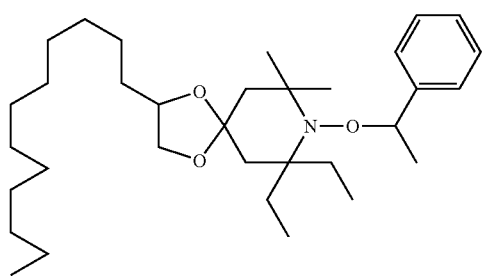
2-Dodecyl-7,7-diethyl-9,9-
dimethyl-8-(1-phenyl-
ethoxy)-1,4-dioxa-8-aza-
spiro[4.5]decane
18 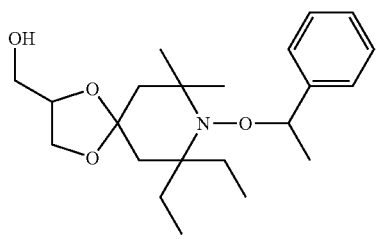
[7,7-Diethyl-9,9-dimethyl-8-
(1-phenyl-ethoxy)-1,4-dioxa-
8-aza-spiro[4.5]dec-2-yl]-
methanol TABLE 2-continued
Compounds according to formula IIa
19
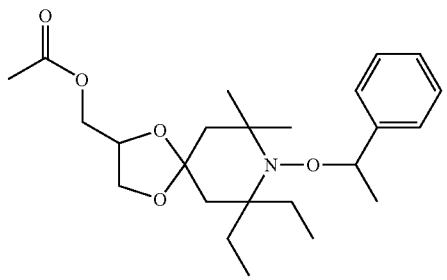
Acetic acid 7,7-diethyl-8-
hydroxy-9,9-dimethyl-1,4-
dioxa-8-aza-spiro[4.5]dec-2-
ylmethyl ester; compound
with isopropyl-benzene
20
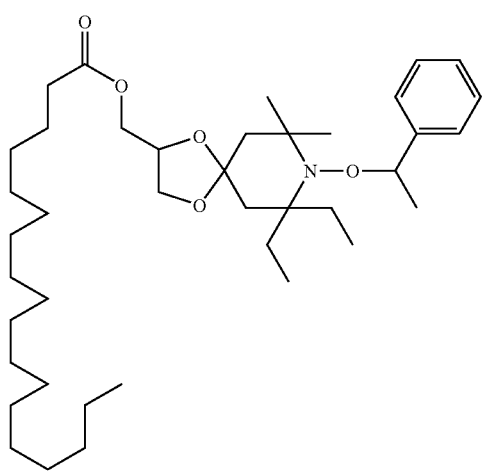
Octadecanoic acid 7,7-
diethyl-9,9-dimethyl-8-(1-
phenyl-ethoxy)-1,4-dioxa-
8-aza-spiro[4.5]dec-2-
ylmethyl ester
21
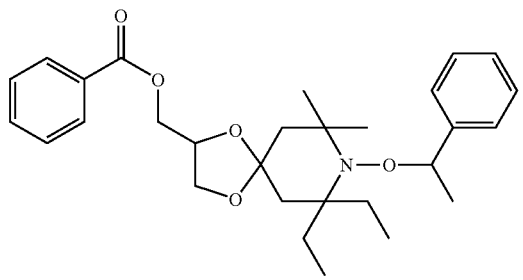
Benzoic acid 7,7-diethyl-8-
hydroxy-9,9-dimethyl-1,4-
dioxa-8-aza-spiro[4.5]dec-2-
ylmethyl ester; compound
with isopropyl-benzene TABLE 2-continued Compounds according to formula IIa 22 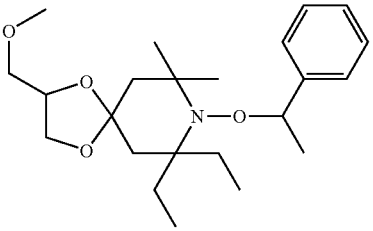

7,7-Diethyl-2-methoxymethyl-
9,9-dimethyl-8-(1-phenyl-
ethoxy)-1,4-dioxa-8-aza-
spiro[4.5]decane 23 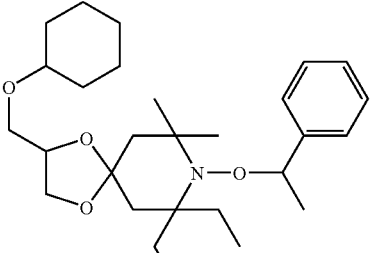

2-Cyclohexyloxymethyl-
7,7-diethyl-9,9-dimethyl-8-
(1-phenyl-ethoxy)-1,4-
dioxa-8-aza-
spiro[4.5]decane 24 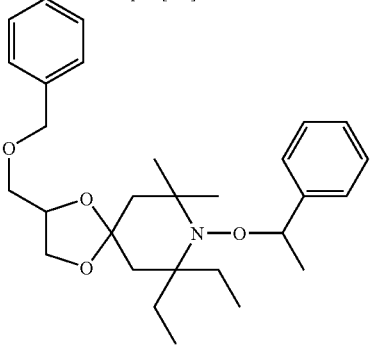

2-Benzyloxymethyl-7,7-
diethyl-9,9-dimethyl-8-(1-
phenyl-ethoxy)-1,4-dioxa-8-
aza-spiro[4.5]decane 25 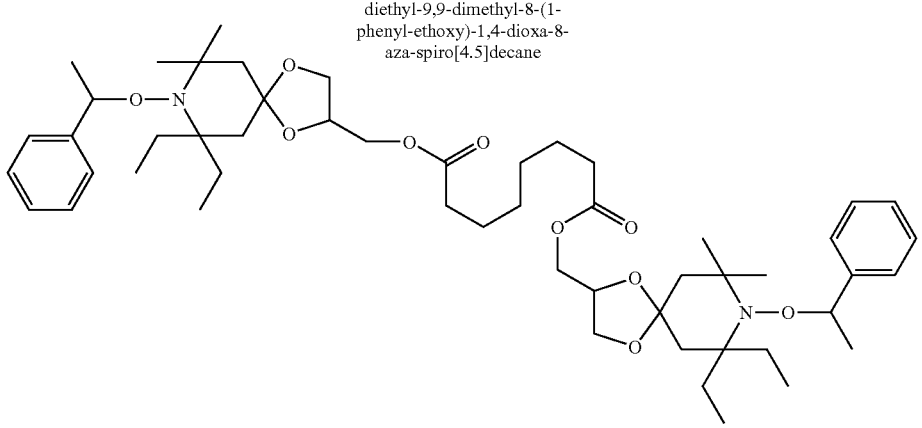

Octanedioic acid bis-[7,7-
diethyl-9,9-dimethyl-8-(1-
phenyl-ethoxy)-1,4-dioxa-8-
aza-spiro[4.5]dec-2-ylmethyl]
ester TABLE 2-continued
Compounds according to formula IIa
26
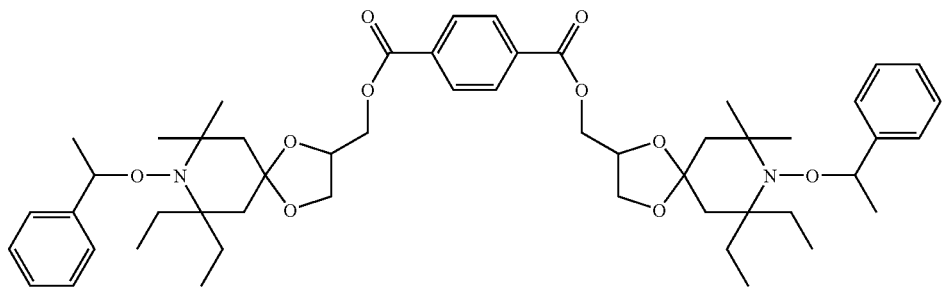
Terephthalic acid bis-[7,7-diethyl-9,9-dimethyl-8-(1-phenyl-ethoxy)-1,4-dioxa-8-aza-spiro[4.5]dec-2-ylmethyl] ester
27
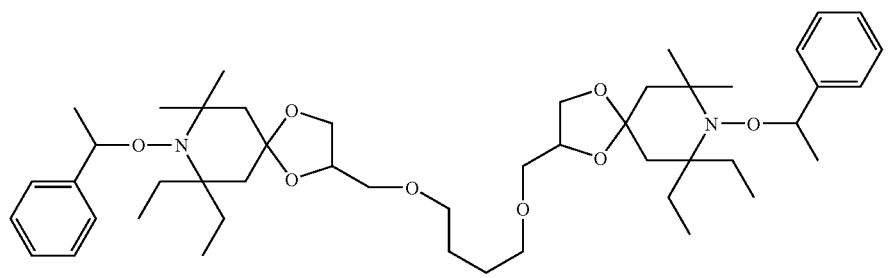
1,4-Bis-{[7,7-diethyl-9,9-dimethyl-8-(1-phenyl-ethoxy)-1,4-dioxa-8-aza-spiro[4.5]dec-2-yl]-methyloxy}-butane
28
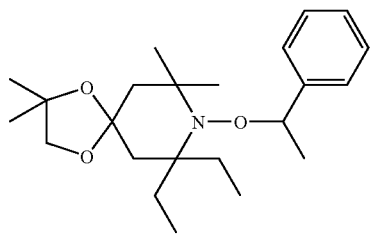
7,7-Diethyl-2,2,9,9-tetramethyl-8-(1-phenyl-ethoxy)-1,4-dioxa-8-aza-spiro[4.5]decane
29
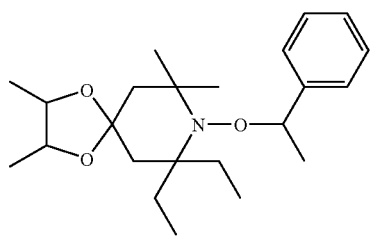
7,7-Diethyl-2,3,9,9-tetramethyl-8-(1-phenyl-ethoxy)-1,4-dioxa-8-aza-spiro[4.5]decane TABLE 2-continued
Compounds according to formula IIa
30 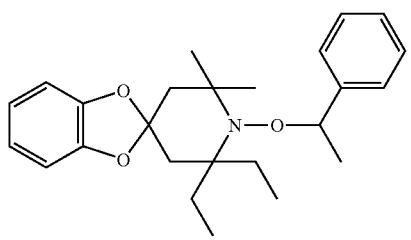
2,3-Benzo-7,7-diethyl-9,9-
dimethyl-8-(1-phenyl-
ethoxy)-1,4-dioxa-8-aza-
spiro[4.5]decane
31 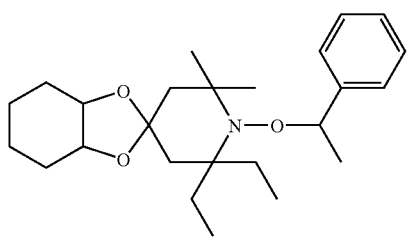
2,3-Cyclohexano-7,7-diethyl-
9,9-dimethyl-8-(1-phenyl-
ethoxy)-1,4-dioxa-8-aza-
spiro[4.5]decane
32 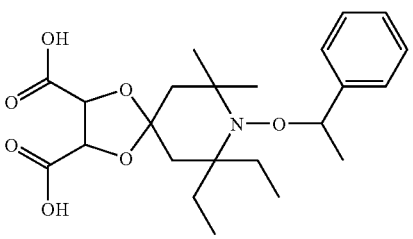
7,7-Diethyl-9,9-dimethyl-8-
(1-phenyl-ethoxy)-1,4-
dioxa-8-aza-
spiro[4.5]decane-2,3-
dicarboxylic acid
33 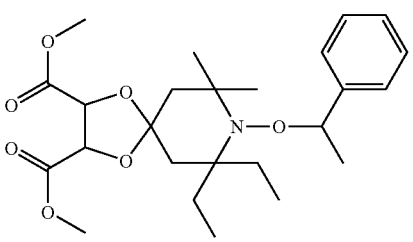
7,7-Diethyl-9,9-dimethyl-8-
(1-phenyl-ethoxy)-1,4-dioxa-
8-aza-spiro[4.5]decane-2,3-
dicarboxylic acid dimethyl
ester TABLE 2-continued
Compounds according to formula IIa
34 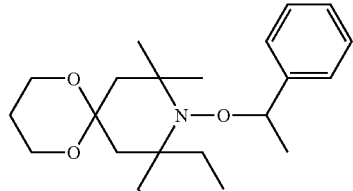
8,8-Diethyl-10,10-dimethyl-9-
(1-phenyl-ethoxy)-1,5-dioxa-
9-aza-spiro[5.5]undecane
35 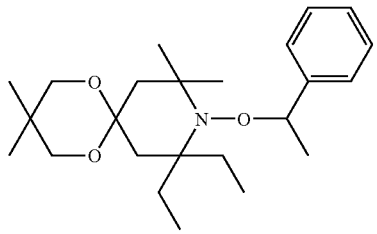
8,8-Diethyl-3,3,10,10-
tetramethyl-9-(1-phenyl-
ethoxy)-1,5-dioxa-9-aza-
spiro[5.5]undecane
36 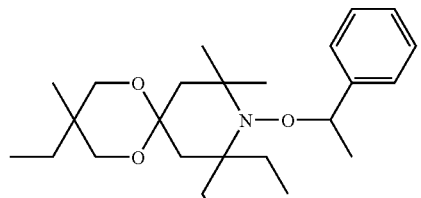
3,8,8-Triethyl-3,10,10-
trimethyl-9-(1-phenyl-
ethoxy)-1,5-dioxa-9-aza-
spiro[5.5]undecane
37 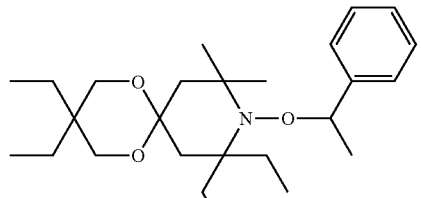
3,3,8,8-Tetraethyl-10,10-
dimethyl-9-(1-phenyl-ethoxy)-
1,5-dioxa-9-aza-
spiro[5.5]undecane
38 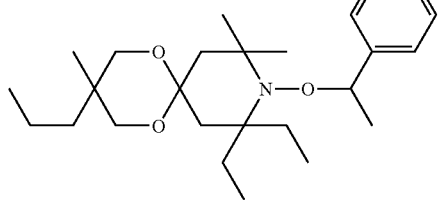
8,8-Diethyl-3,10,10-
trimethyl-9-(1-phenyl-
ethoxy)-3-propyl-1,5-dioxa-
9-aza-spiro[5.5]undecane TABLE 2-continued
Compounds according to formula IIa
39
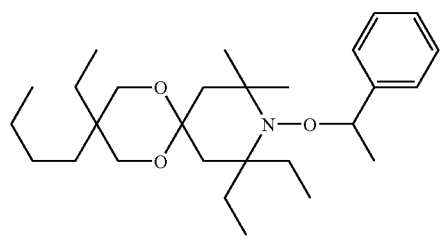
3-Butyl-3,8,8-triethyl-10,10-
dimethyl-9-(1-phenyl-
ethoxy)-1,5-dioxa-9-aza-
spiro[5.5]undecane
40
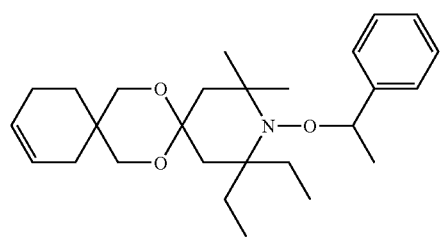
2,2-Diethyl-4,4-dimethyl-3-(1-
phenyl-ethoxy)-7,16-dioxa-3-
aza-dispiro[5.2.5.2]hexadec-
11-ene
41
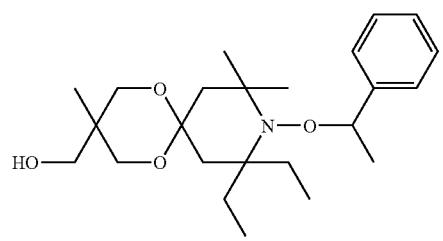
[8,8-Diethyl-3,10,10-tri-
methyl-9-(1-phenyl-eth-
oxy)-1,5-dioxa-9-aza-
spiro[5.5]undec-3-yl]-
methanol
42
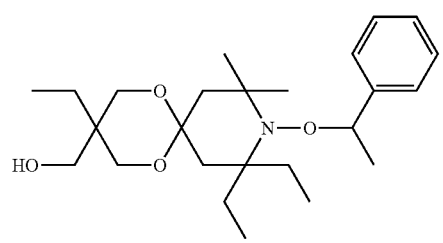
[3,8,8-Triethyl-10,10-
dimethyl-9-(1-phenyl-
ethoxy)-1,5-dioxa-9-aza-
spiro[5.5]undec-3-yl]-
methanol TABLE 2-continued Compounds according to formula IIa

43

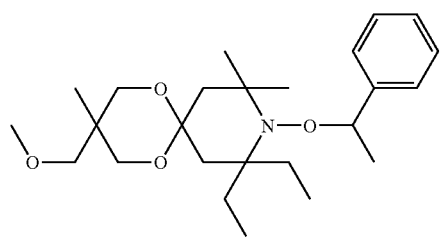

8,8-Diethyl-3-methoxymethyl-
3,10,10-trimethyl-9-(1-phenyl-
ethoxy)-1 5-dioxa-9-aza-
spiro[5.5]undecane

44

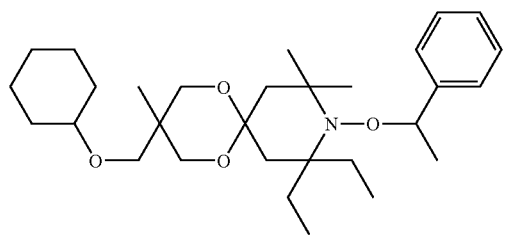

3-Cyclohexyloxymethyl-
8,8-diethyl-3,10,10-
trimethyl-9-(1-phenyl-
ethoxy)-1,5-dioxa-9-aza-
spiro[5.5]undecane

45

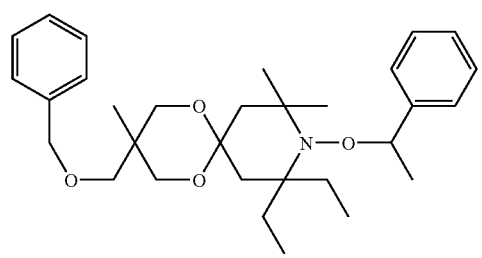

3-Benzyloxymethyl-8,8-
diethyl-3,10,10-trimethyl-9-
(1-phenyl-ethoxy)-1,5-dioxa-
9-aza-spiro[5.5]undecane

46

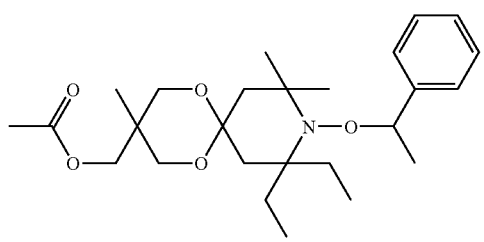

Acetic acid 8,8-diethyl-
3,10,10-trimethyl-9-(1-phenyl-
ethoxy)-1,5-dioxa-9-aza-
spirot[5.5]undec-3-ylmethyl
ester TABLE 2-continued Compounds according to formula IIa 47 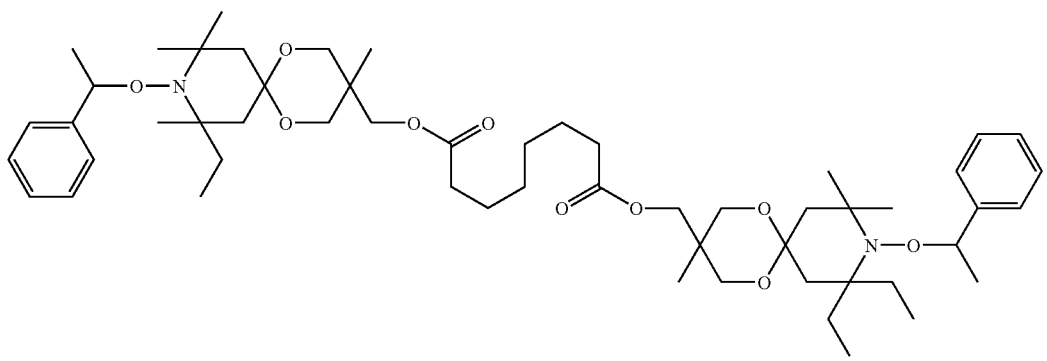

Octanedioic acid bis-[8,8-
diethyl-3,10,10-trimethyl-9-
(1-phenyl-ethoxy)-1,5-
dioxa-9-aza-
spiro[5.5]undec-3-ylmethyl]
ester 48 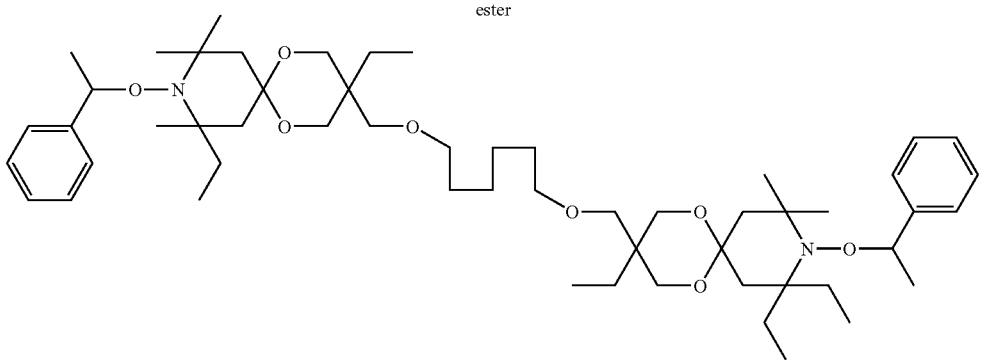

1,6-Bis{[3,8,8-triethyl-10,10-
dimethyl-9-(1-phenyl-
ethoxy)-1,5-dioxa-9-aza-
spiro[5.5]undec-3-yl]-
methyloxy}-1-hexane 49 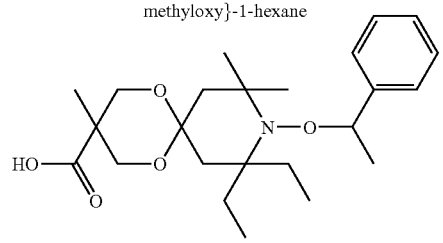

8,8-Diethyl-3,10,10-trimethyl-
9-(1-phenyl-ethoxy)-1,5-
dioxa-9-aza-
spiro[5.5]undecane-3-
carboxylic acid 50 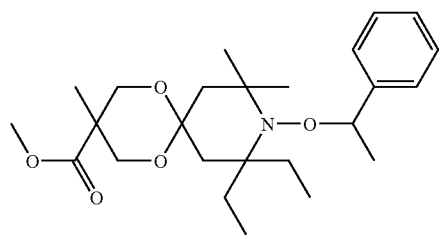

8,8-Diethyl-3,10,10-
trimethyl-9-(1-phenyl-
ethoxy)-1,5-dioxa-9-aza-
spiro[5.5]undecane-3-
carboxylic acid methyl
ester TABLE 2-continued Compounds according to formula IIa

51

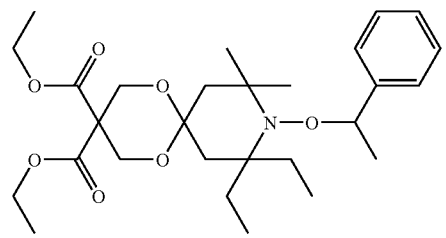

8,8-Diethyl-10,10-dimethyl-
9-(1-phenyl-ethoxy)-1,5-
dioxa-9-aza-
spiro[5 5]undecane-3,3-
dicarboxylic acid diethyl
ester

52

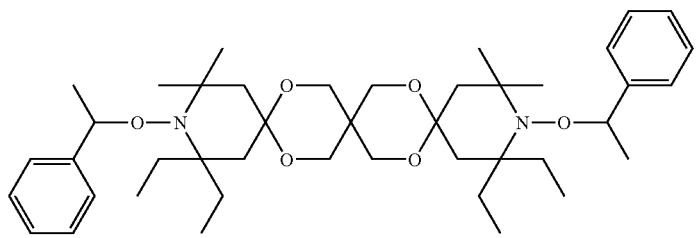

3,3-Bisspiro{8,8-diethyl-
10,10-dimethyl-9-(1-phenyl-
ethoxy)-1,5-dioxa-9-aza-
spiro[5.5]undecane}

53

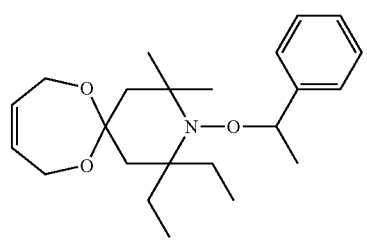

2,2-Diethyl-4,4-dimethyl-3-
(1-phenyl-ethoxy)-7,12-
dioxa-3-aza-
spiro[5.6]dodec-9-ene

TABLE 3

Compounds according to formula IIIa

1

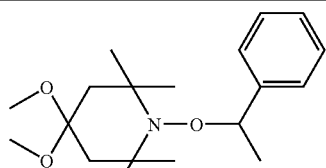

4,4-Dimethoxy-2,2,6,6-
tetramethyl-1-(1-phenyl-
ethoxy)-piperidine

TABLE 3-continued
Compounds according to formula IIIa
2 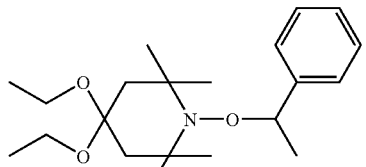
4,4-Diethoxy-2,2,6,6-
tetramethyl-1-(1-phenyl-
ethoxy)-piperidine
3 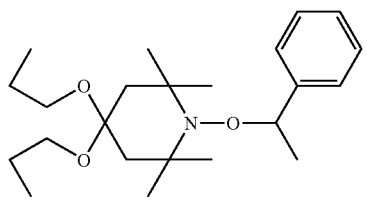
2,2,6,6-Tetramethyl-1-(1-
phenyl-ethoxy)-4,4-
dipropoxy-piperidine
4 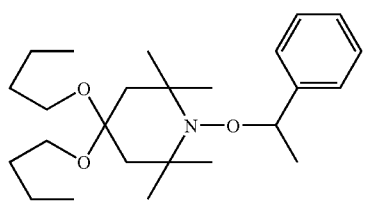
4,4-Dibutoxy-2,2,6,6-
tetramethyl-1-(1-phenyl
ethoxy)-piperidine
5 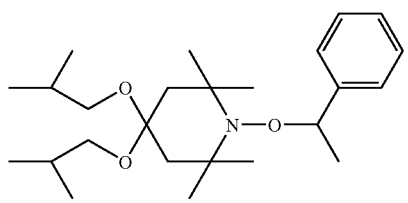
4-Diisobutoxy-2,2,6,6-
tetramethyl-1-(1-phenyl
ethoxy)-piperidine
6 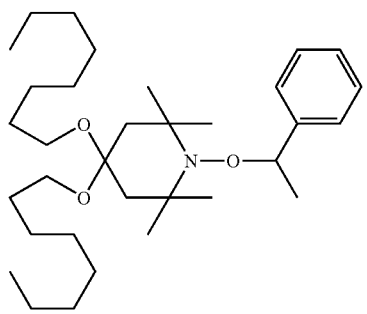
2,2,6,6-Tetramethyl-4,4-bis-
octyloxy-1-(1-phenyl
ethoxy)-piperidine TABLE 3-continued
Compounds according to formula IIIa
7
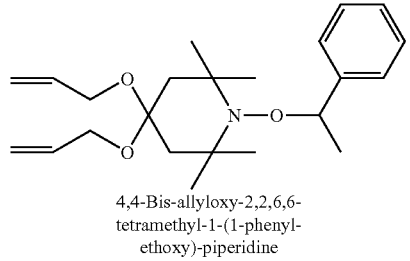
4,4-Bis-allyloxy-2,2,6,6-
tetramethyl-1-(1-phenyl-
ethoxy)-piperidine
8
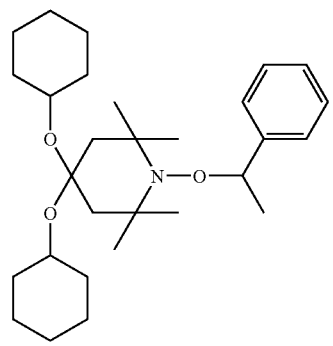
4,4-Bis-cyclohexyloxy-
2,2,6,6-tetramethyl-1-(1-
phenyl-ethoxy)-piperidine
9
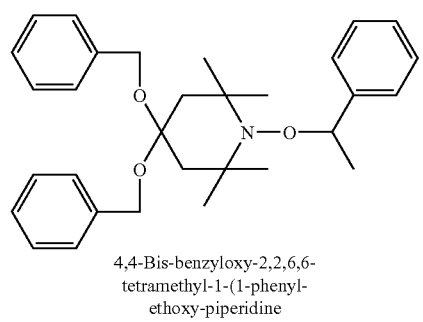
4,4-Bis-benzyloxy-2,2,6,6-
tetramethyl-1-(1-phenyl-
ethoxy-piperidine
10
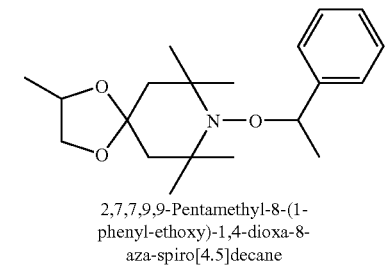
2,7,7,9,9-Pentamethyl-8-(1-
phenyl-ethoxy)-1,4-dioxa-8-
aza-spiro[4.5]decane
11
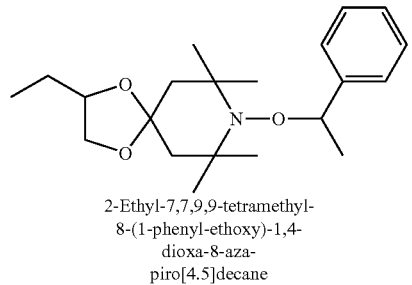
2-Ethyl-7,7,9,9-tetramethyl-
8-(1-phenyl-ethoxy)-1,4-
dioxa-8-aza-
piro[4.5]decane TABLE 3-continued
Compounds according to formula IIIa
12
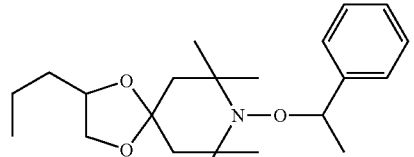
7,7,9,9-Tetramethyl-8-(1-
phenyl-ethoxy)-2-propyl-
1,4-dioxa-8-aza-
spiro[4.5]decane
13
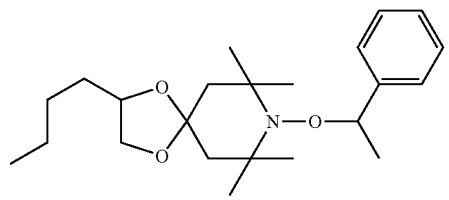
2-Butyl-7,7,9,9-tetramethyl-
8-(1-phenyl-ethoxy)-1,4-
dioxa-8-aza-
spiro[4.5]decane
14
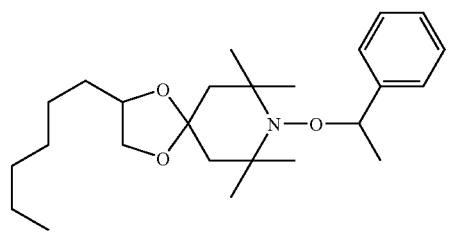
7,7,9,9-Tetramethyl-2-
octyl-8-(1-phenyl-ethoxy)-
1,4-dioxa-8-aza-
spiro[4.5]decane
15
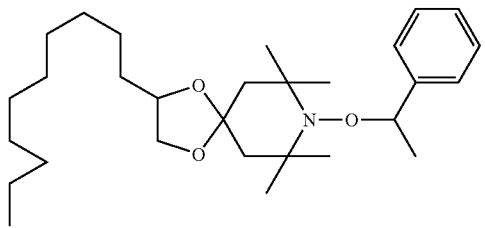
2-Decyl-7,7,9,9-
tetramethyl-8-(1-phenyl-
ethoxy)-1,4-dioxa-8-aza-
spiro[4.5]decane
16
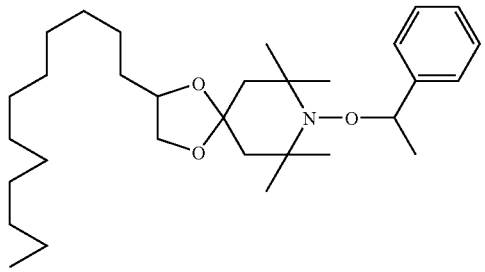
2-Dodecyl-7,7,9,9-
tetramethyl-8-(1-phenyl-
ethoxy)-1,4-dioxa-8-aza-
spiro[4.5]decane TABLE 3-continued Compounds according to formula IIIa 17
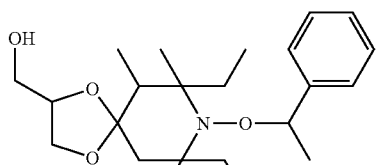
[7,7,9,9-Tetramethyl-8-(1-phenyl-ethoxy)-1,4-dioxa-8-aza-spiro[4.5]dec-2-yl]-methanol 18
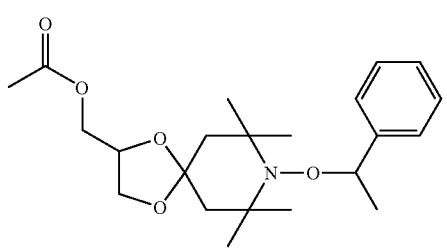
Acetic acid 8-hydroxy-7,7,9,9-tetramethyl-1,4-dioxa-8-aza-spiro[4.5]dec-2-ylmethyl ester; compound with isopropyl-benzene 19
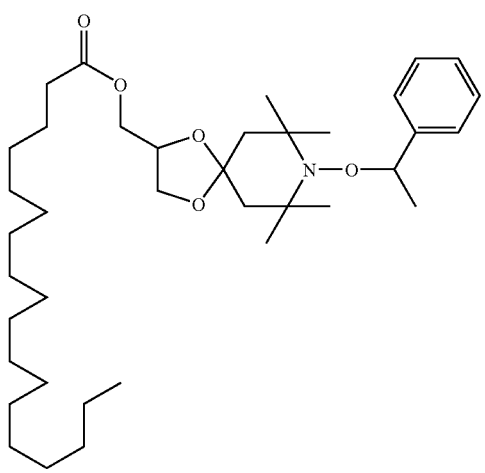
Octadecanoic acid 7,7,9,9-tetramethyl-8-(1-phenyl-ethoxy)-1,4-dioxa-8-aza-spiro [4.5]dec-2-ylmethyl ester 20
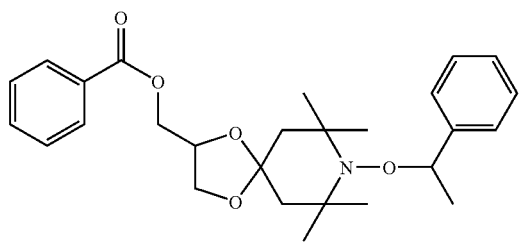
Benzoic acid 7,7,9,9-tetramethyl-8-(1-phenyl-ethoxy)-1,4-dioxa-8-aza-spiro[4.5]dec-2-ylmethyl ester TABLE 3-continued
Compounds according to formula IIIa
21 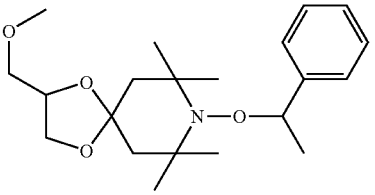
2-Methoxymethyl-7,7,9,9-
tetramethyl-8-(1-phenyl-
ethoxy)-1,4-dioxa-8-aza-
spiro[4.5]decane
22 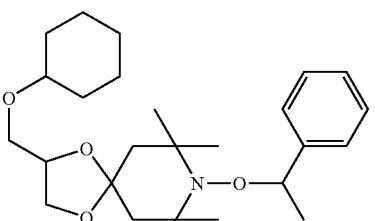
2-Cyclohexyloxymethyl-
7,7,9,9-tetramethyl-8-(1-
phenyl-ethoxy)-1,4-dioxa-8-
aza-spiro[4.5]decane
23 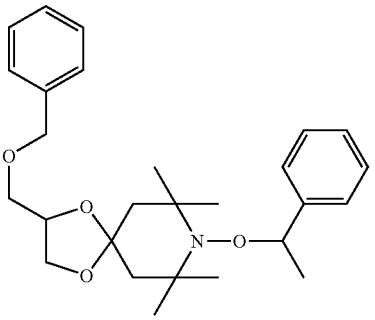
2-Benzyloxymethyl-7,7,9,9-
tetramethyl-8-(1-phenyl-
ethoxy)-1,4-dioxa-8-aza-
spiro[4.5]decane
24 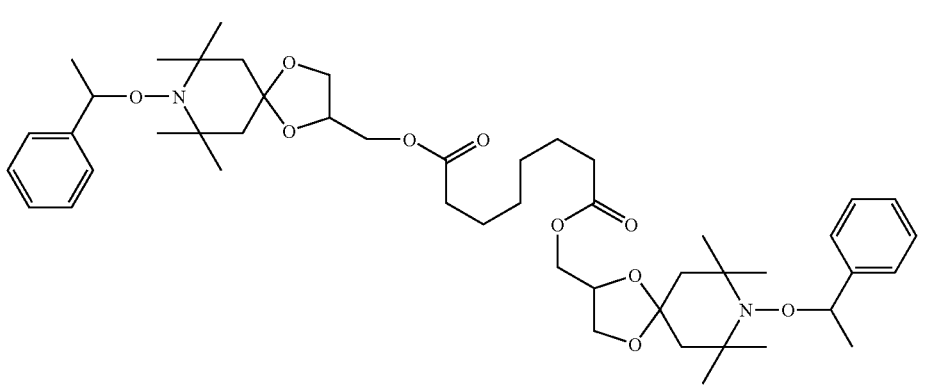
Octanedioic acid bis-
[7,7,9,9-tetramethyl-8-(1-
phenyl-ethoxy)-1,4-dioxa-8-
aza-spiro[4.5]dec-2-
ylmethyl] ester

TABLE 3-continued
Compounds according to formula IIIa
25
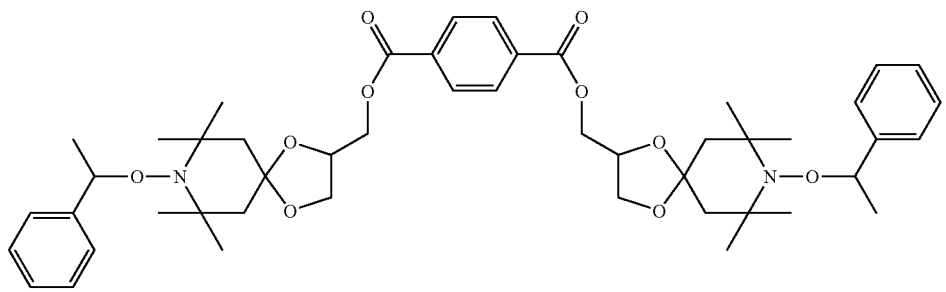
Terephthalic acid bis-
[7,7,9,9-tetramethyl-8-(1-
phenyl-ethoxy)-1,4-dioxa-8-
aza-spiro[4.5]dec-2-
ylmethyl] ester
26
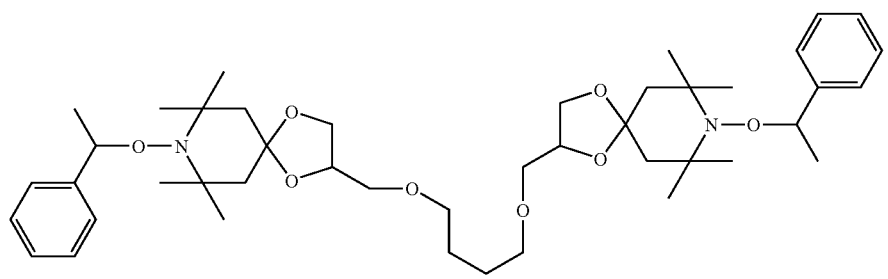
1,4-Bis-{[7,7,9,9-
tetramethyl-8-(1-phenyl-
ethoxy)1,4-dioxa-8-aza-
spiro[4.5]dec-2-yl]-
methyloxy}butane
27
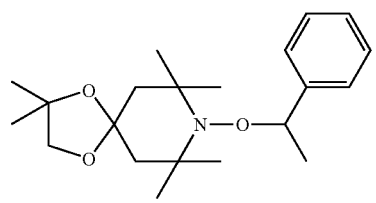
2,2,7,7,9,9-Hexamethyl-8-
(1-phenyl-ethoxy)-1,4-
dioxa-8-aza-
spiro[4.5]decane
28
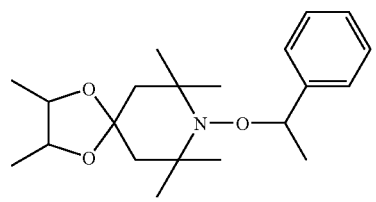
2,3,7,7,9,9-Hexamethyl-8-
(1-phenyl-ethoxy)-1,4-
dioxa-8-aza-
spiro[4.5]decane TABLE 3-continued Compounds according to formula IIIa 29 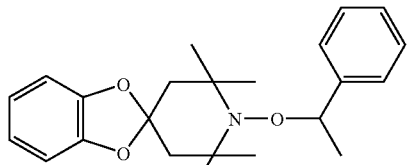

2,3-Benzo-7,7,9,9-
tetramethyl-8-(1-phenyl-
ethoxy)-1,4-dioxa-8-aza-
spiro[4.5]decane 30 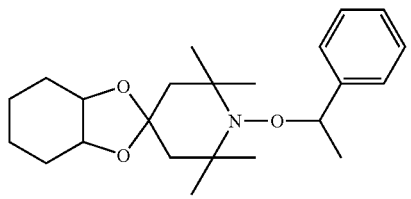

2,3-Cyclohexano-7,7,9,9-
tetramethyl-8-(1-phenyl-
ethoxy)-1,4-dioxa-8-aza-
spiro[4.5]decane 31 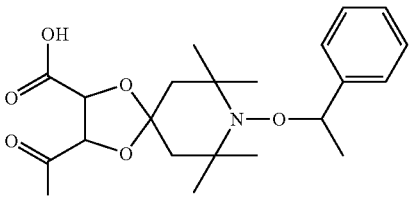

7,7,9,9-Tetramethyl-8-(1-
phenyl-ethoxy)-1,4-dioxa-8-
aza-spiro[4.5]decane-2,3-
dicarboxylic acid 32 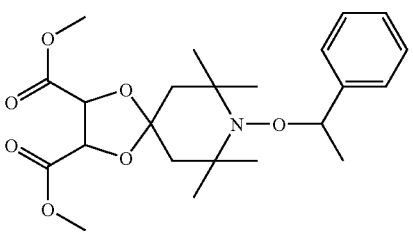

7,7,9,9-Tetramethyl-8-(1-
phenyl-ethoxy)-1,4-dioxa-8-
aza-spiro[4.5]decane-2,3-
dicarboxylic acid dimethyl
ester 33 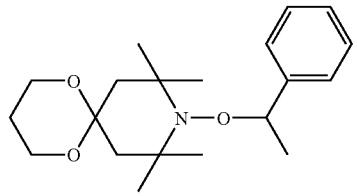

8,8,10,10-Tetramethyl-9-(1-
phenyl-ethoxy)-1,5-dioxa-9-
aza-spiro[5.5]undecane

TABLE 3-continued
Compounds according to formula IIIa
34 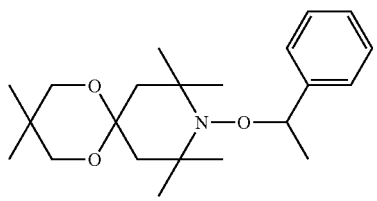
3,3,8,8,10,10-Hexamethyl-
9-(1-phenyl-ethoxy)-1,5-
dioxa-9-aza-
spiro[5.5]undecane
35 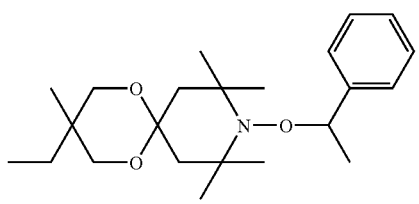
3-Ethyl-3,8,8,10,10-
pentamethyl-9-(1-phenyl-
ethoxy)-1,5-dioxa-9-aza-
spiro[5.5]undecane
36 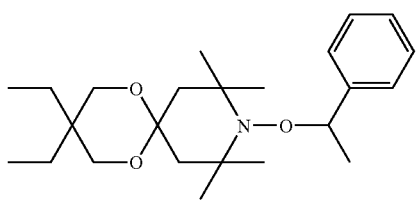
3,3-Diethyl-8,8,10,10-
tetramethyl-9-(1-phenyl-
ethoxy)1,5-dioxa-9-aza-
spiro[5.5]undecane
37 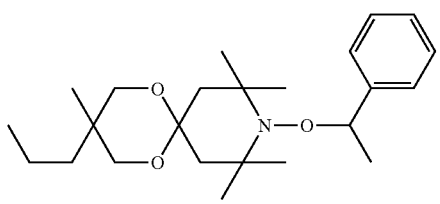
3,8,8,10,10-Pentamethyl-9-
(1-phenyl-ethoxy)-3-propyl-
1,5-dioxa-9-aza-
spiro[5.5]undecane
38 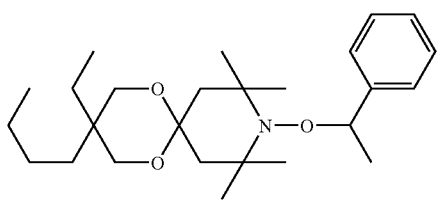
3-Butyl-3-ethyt-8,8,10,10-
tetramethyl-9-(1-phenyl-
ethoxy)-1,5-dioxa-9-aza-
spiro[5.5]undecane TABLE 3-continued Compounds according to formula IIIa

39

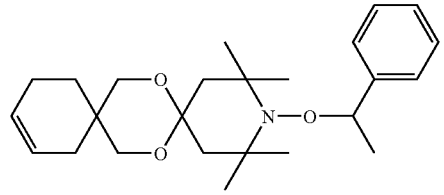

2,2,4,4-Tetramethyl-3-(1-phenyl-ethoxy)-7,16-dioxa-3-aza-dispiro[5.2.5.2]hexadec-11-ene

40

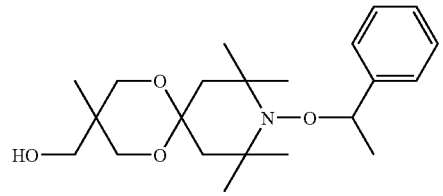

3,8,8,10,10-Pentamethyl-9-(1-phenyl-ethoxy)-1,5-dioxa-9-aza-spiro[5.5]undec-3-yl]-methanol

41

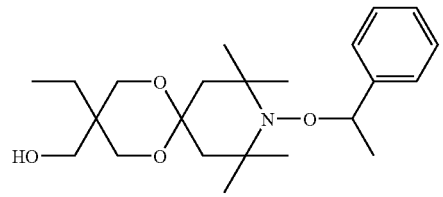

[3-Ethyl-8,8,10,10-tetramethyl-9-(1-phenyl-ethoxy)-1,5-dioxa-9-aza-spiro[5.5]undec-3-yl]-methanol

42

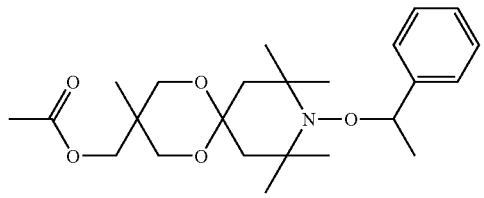

Acetic acid 3,8,8,10,10-pentamethyl-9-(1-phenyl-ethoxy)1,5-dioxa-9-aza-spiro[5.5]undec-3-ylmethyl ester

43

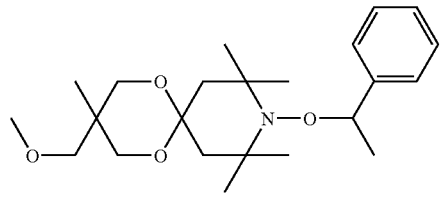

3-Methoxymethyl-3,8,8,10,10-pentamethyl-9-(1-phenyl-ethoxy)-1,5-dioxa-9-aza-spiro[5.5]undecane TABLE 3-continued Compounds according to formula IIIa

44

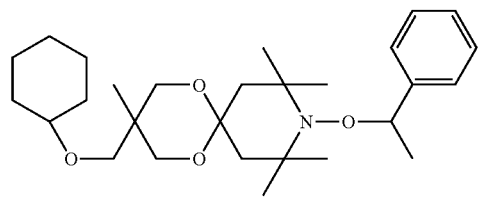

3-Cyclohexyloxymethyl-
3,8,8,10,10-pentamethyl-9-
(1-phenyl-ethoxy)-1,5-
dioxa-9-aza-
spiro[5.5]undecane

45

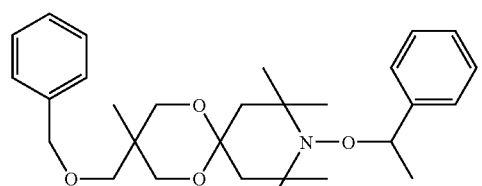

3-Benzyloxymethyl-
3,8,8,10,10-pentamethyl-9-
(1-phenyl-ethoxy)-1,5-
dioxa-9-aza-
spiro[5.5]undecane

46

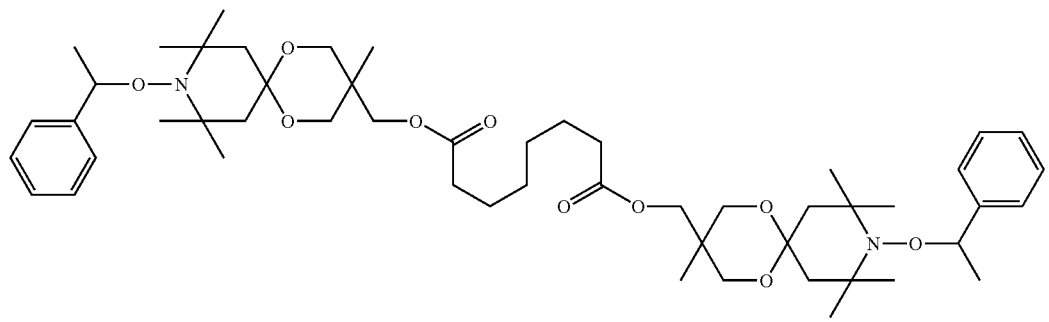

Octanedioic acid bis-
[3,8,8,10,10-pentamethyl-9-
(1-phenyl-ethoxy)-1,5-
dioxa-9-aza-
spiro[5.5]undec-3-ylmethyl]
ester

47

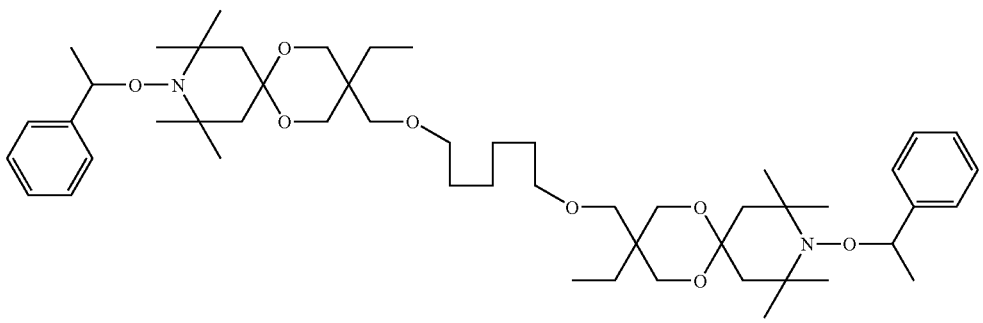

1-,6-Bis-{[3-ethyl-8,8,10,10-
tetramethyl-9-(1-phenyl-
ethoxy)-1,5-dioxa-9-aza-
spiro[5.5]undec-3-yl]-
methyloxy}-hexane TABLE 3-continued
Compounds according to formula IIIa
48
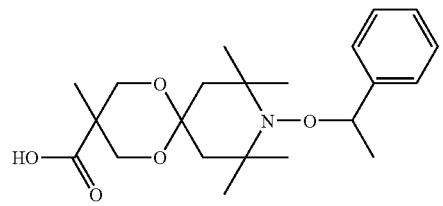
3,8,8,10,10-Pentamethyl-9-
(1-phenyl-ethoxy)-1,5-
dioxa-9-aza-
spiro[5.5]undecane-3-
carboxylic acid
49
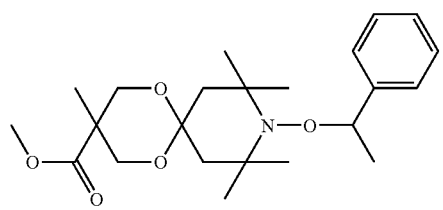
3,8,8,10,10-Pentamethyl-9-
(1-phenyl-ethoxy)-1,5-
dioxa-9-aza-
spiro[5.5]undecane-3-
carboxylic acid methyl ester
50
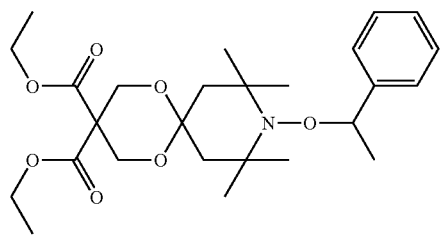
8,8,10,10-Tetramethyl-9-
(1-phenyl-ethoxy)-1,5-
dioxa-9-aza-
spiro[5.5]undecane-3,3-
dicarboxylic acid diethyl
ester
51
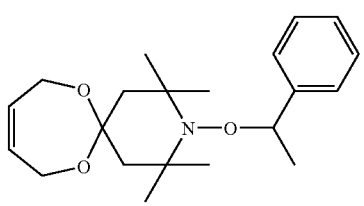
2,2,4,4-Tetramethyl-3-(1-
phenyl-ethoxy)-7,I 2-dioxa-
3-aza-spiro[5.6]dodec-9-
ene Particularly preferred are the compounds of Table 1 and 2.

Most preferred are following compounds:

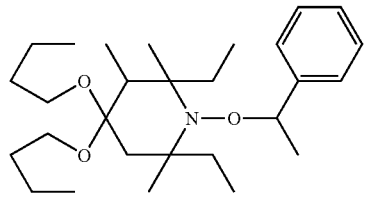

4,4-Dibutoxy-2,6-diethyl-2,3,6-trimethyl-1-(1-phenyl-ethoxy)-piperidine (Table 1, No. 4)

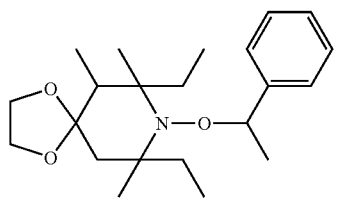

7,9-Diethyl-6,7,9-trimethyl-8-(1-phenyl-ethoxy)-1,4-dioxa-8-aza-spiro[4.5]decane (Table 1, No. 10)

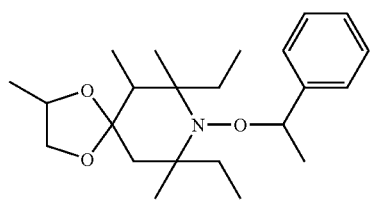

7,9-Diethyl-2,6,7,9-tetramethyl-8-(1-phenyl-ethoxy)-1,4-dioxa-8-aza-spiro[4.5]decane (Table 1, No. 11)

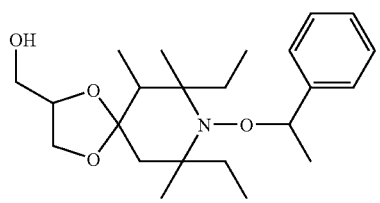

[7,9-Diethyl-6,7,9-trimethyl-8-(1-phenyl-ethoxy)-1,4-dioxa-8-aza-spiro[4.5]dec-2-yl]-methanol (Table 1, No. 18)

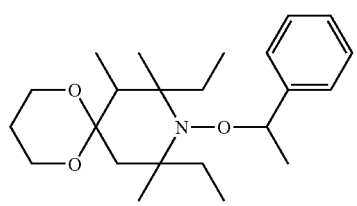

8,10-Diethyl-7,8,10-trimethyl-9-(1-phenyl-ethoxy)-1,5-dioxa-9-aza-spiro[5.5]undecane (Table 1, No. 34)

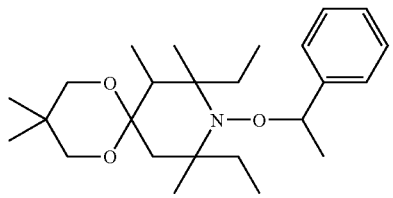

8,10-Diethyl-3,3,7,8,10-pentamethyl-9-(1-phenyl-ethoxy)-1,5-dioxa-9-aza-spiro[5.5]undecane (Table 1, No. 35)

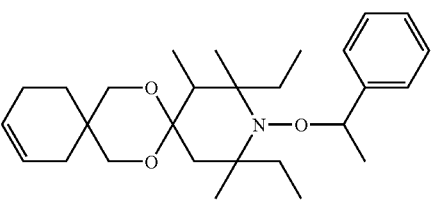

2,4-Diethyl-1,2,4-trimethyl-3-(1-phenylethoxy)-7,16-dioxa-3-aza-dispiro[5.2.5.2]hexadec-1-ene (Table 1, No. 40)

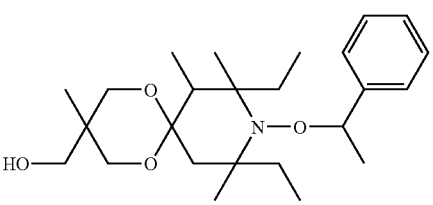

[8,10-Diethyl-3,7,8,10-tetramethyl-9-(1-phenylethoxy)-1,5-dioxa-9-aza-spiro[5.5]undec-3-yl]-methanol (Table 1, No 41)

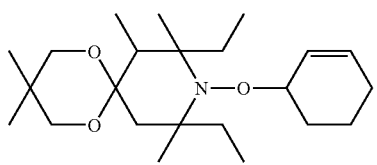

9-(Cyclohex-2-enyloxy)-8,10-diethyl-3,3,7,8,10-pentamethyl-1,5-dioxa-9-aza-spiro[5.5]undecane Preferably the ethylenically unsaturated monomer or oligomer is selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl)acrylamides, vinyl halides or vinylidene halides.

Particularly the ethylenically unsaturated monomers are ethylene, propylene, n-butylene, i-butylene, isoprene, 1,3-butadiene, $\alpha$-$C_5$-$C_{18}$alkene, styrene, $\alpha$-methyl styrene, p-methyl styrene or a compound of formula $CH_2$=$C(R_a)$—$(C$=$Z)$-$R_b$, wherein $R_a$ is hydrogen or $C_1$-$C_4$alkyl, $R_b$ is $NH_2$, $O^-(Me^+)$, glycidyl, unsubstituted $C_1$-$C_{18}$alkoxy, $C_2$-$C_{100}$alkoxy interrupted by at least one N and/or O atom, or hydroxy-substituted $C_1$-$C_{18}$alkoxy, unsubstituted $C_1$-$C_{18}$alkylamino, di($C_1$-$C_{18}$alkyl)amino, hydroxy-substituted $C_1$-$C_{18}$alkylamino or hydroxy-substituted di($C_1$-$C_{18}$alkyl)amino, —O—$CH_2$—$CH_2$—N($CH_3$)$_2$ or —O—$CH_2$—$CH_2$—$N^+H(CH_3)_2$ $An^-$;

$An^-$ is a anion of a monovalent organic or inorganic acid;

Me is a monovalent metal atom or the ammonium ion.

Z is oxygen or sulfur.

Examples for $R_a$ as $C_2$-$C_{100}$alkoxy interrupted by at least one O atom are of formula

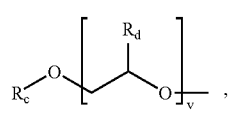

wherein $R_c$ is $C_1$-$C_{25}$alkyl, phenyl or phenyl substituted by $C_1$-$C_{18}$alkyl, $R_d$ is hydrogen or methyl and v is a number from 1 to 50. These monomers are for example derived from non ionic surfactants by acrylation of the corresponding alkoxylated alcohols or phenols. The repeating units may be derived from ethylene oxide, propylene oxide or mixtures of both.

Further examples of suitable acrylate or methacrylate monomers are given below.

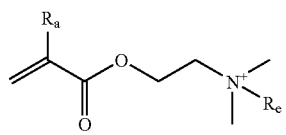

$An^-$ or

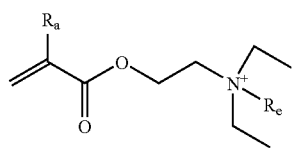

$An^-$, wherein $An^-$ and $R_a$ have the meaning as defined above and $R_e$ is methyl or benzyl. $An^-$ is preferably $Cl^-$, $Br^-$ or $^-O_3S$—$CH_3$.

Further acrylate monomers are

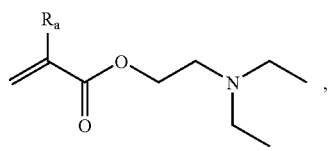

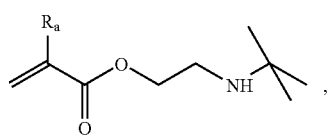

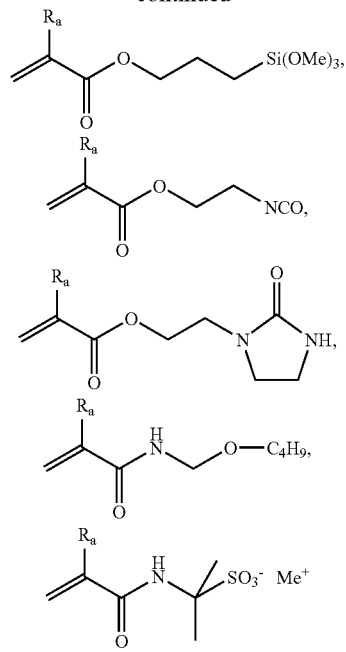

Examples for suitable monomers other than acrylates are

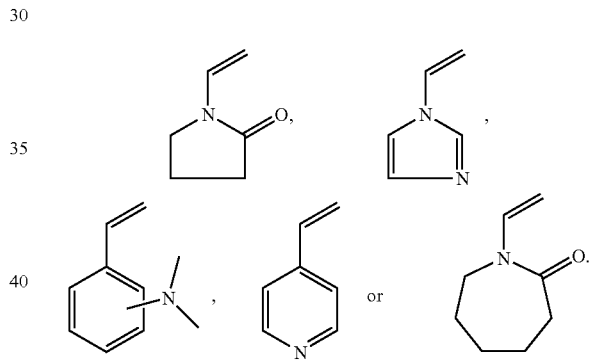

Preferably $R_a$ is hydrogen or methyl, $R_b$ is $NH_2$, gycidyl, unsubstituted or with hydroxy substituted $C_1$-$C_4$alkoxy, unsubstituted $C_1$-$C_4$alkylamino, di($C_1$-$C_4$alkyl)amino, hydroxy-substituted $C_1$-$C_4$alkylamino or hydroxy-substituted di($C_1$-$C_4$alkyl)amino; and Z is oxygen.

Particularly preferred ethylenically unsaturated monomers are styrene, methylacrylate, ethylacrylate, butylacrylate, isobutylacrylate, tert. butylacrylate, hydroxyethylacrylate, hydroxypropylacrylate, dimethylaminoethylacrylate, glycidylacrylates, methyl(meth)acrylate, ethyl(meth)acrylate, butyl(meth)acrylate, hydroxyethyl(meth)acrylate, hydroxypropyl(meth)acrylate, dimethylaminoethyl(meth)acrylate, glycidyl(meth)acrylates, acrylonitrile, acrylamide, methacrylamide or dimethylaminopropyl-methacrylamide.

Preferably the initiator compound is present in an amount of from 0.01 mol-% to 20 mol-%, more preferably in an amount of from 0.01 mol-% to 10 mol-% and most preferred in an amount of from 0.05 mol-% to 10 mol-% based on the monomer or monomer mixture.

When monomer mixtures are used mol-% is calculated on the average molecular weight of the mixture.

Another subject of the present invention is a process for preparing an oligomer, a cooligomer, a polymer or a copolymer (block or random) by free radical polymerization of at least one ethylenically unsaturated monomer or oligomer, which comprises (co)polymerizing the monomer or monomers/oligomers in the presence of an initiator compound of formula Ia, IIa or IIIa under reaction conditions capable of effecting scission of the O—C bond to form two free radicals, the radical •X being capable of initiating polymerization.

Preferably scission of the O—C bond is effected by ultrasonic treatment, healing or exposure to electromagnetic radiation, ranging from γ to microwaves.

More preferably the scission of the O—C bond is effected by heating and takes place at a temperature of between 50° C. and 160° C.

Preferred initiators and ethylenically unsaturated monomers have already been mentioned above.

The process may be carried out in the presence of an organic solvent or in the presence of water or in mixtures of organic solvents and water. Additional cosolvents or surfactants, such as glycols or ammonium salts of fatty acids, may be present. Other suitable cosolvents are described hereinafter.

Preferred processes use as little solvents as possible. In the reaction mixture it is preferred to use more than 30% by weight of monomer and initiator, particularly preferably more than 50% and most preferrably more than 80%.

If organic solvents are used, suitable solvents or mixtures of solvents are typically pure alkanes (hexane, heptane, octane, isooctane), hydrocarbons (benzene, toluene, xylene), halogenated hydrocarbons (chlorobenzene), alkanols (methanol, ethanol, ethylene glycol, ethylene glycol monomethyl ether), esters (ethyl acetate, propyl, butyl or hexyl acetate) and ethers (diethyl ether, dibutyl ether, ethylene glycol dimethyl ether), or mixtures thereof.

The aqueous polymerization reactions can be supplemented with a water-miscible or hydrophilic cosolvent to help ensure that the reaction mixture remains a homogeneous single phase throughout the monomer conversion. Any water-soluble or water-miscible cosolvent may be used, as long as the aqueous solvent medium is effective in providing a solvent system which prevents precipitation or phase separation of the reactants or polymer products until after all polymerization reactions have been completed. Exemplary cosolvents useful in the present invention may be selected from the group consisting of aliphatic alcohols, glycols, ethers, glycol ethers, pyrrolidines, N-alkyl pyrrolidinones, N-alkyl pyrrolidones, polyethylene glycols, polypropylene glycols, amides, carboxylic acids and salts thereof, esters, organosulfides, sulfoxides, sulfones, alcohol derivatives, hydroxyether derivatives such as butyl carbitol or cellosolve, amino alcohols, ketones, and the like, as well as derivatives thereof and mixtures thereof. Specific examples include methanol, ethanol, propanol, dioxane, ethylene glycol, propylene glycol, diethylene glycol, glycerol, dipropylene glycol, tetrahydrofuran, and other water-soluble or water-miscible materials, and mixtures thereof. When mixtures of water and water-soluble or water-miscible organic liquids are selected as the aqueous reaction media, the water to cosolvent weight ratio is typically in the range of about 100:0 to about 10:90.

The process is particularly useful for the preparation of block copolymers.

Block copolymers are, for example, block copolymers of polystyrene and polyacrylate (e.g., poly(styrene-co-acrylate) or poly(styrene-co-acrylate-co-styrene). They are usefull as adhesives or as compatibilizers for polymer blends or as polymer toughening agents. Poly(methylmethacrylate-co-acrylate) diblock copolymers or poly(methylacrylate-co-acrylate-co-methacrylate) triblock copolymers) are useful as dispersing agents for coating systeme, as coating additives (e.g. Theological agents, compatibilizers, reactive diluents) or as resin component in coatings (e.g. high solid paints) Block copolymers of styrene, (meth)acrylates and/or acrylonitrile are useful for plastics, elastomers and adhesives.

Furthermore, block copolymers of this invention, wherein the blocks alternate between polar monomers and non-polar monomers, are useful in many applications as amphiphilic surfactants or dispersants for preparing highly uniform polymer blends. The (co)polymers of the present invention may have a number average molecular weight from 1 000 to 400 000 g/mol, preferably from 2 000 to 250 000 g/mol and, more preferably, from 2 000 to 200 000 g/mol. When produced in bulk, the number average molecular weight may be up to 500 000 (with the same minimum weights as mentioned above). The number average molecular weight may be determined by size exclusion chromatography (SEC), gel permeation chromatography (GPC), matrix assisted laser desorption/ionization mass spectrometry (MALDI-MS) or, if the initiator carries a group which can be easily distinguished from the monomer(s), by NMR spectroscopy or other conventional methods.

The polymers or copolymers of the present invention have preferably a polydispersity of from 1.0 to 2, more preferably of from 1.1 to 1.9 and most preferably from 1.1 to 1.8.

Thus, the present invention also encompasses in the synthesis novel block, multi-block, star, gradient, random, hyperbranched and dendritic copolymers, as well as graft or copolymers.

The polymers prepared by the present invention are useful for following applications:

adhesives, detergents, dispersants, emulsifiers, surfactants, defoamers, adhesion promoters, corrosion inhibitors, viscosity improvers, lubricants, rheology modifiers, thickeners, crosslinkers, paper treatment, water treatment, electronic materials, paints, coatings, photography, ink materials, imaging materials, superabsorbants, cosmetics, hair products, preservatives, biocide materials or modifiers for asphalt, leather, textiles, ceramics and wood.

Because the present polymerizaton is a "living" polymerization, it can be started and stopped practically at will. Furthermore, the polymer product retains the functional alkoxyamine group allowing a continuation of the polymerization in a living matter. Thus, in one embodiment of this invention, once the first monomer is consumed in the initial polymerizing step a second monomer can then be added to form a second block on the growing polymer chain in a second polymerization step. Therefore it is possible to carry out additional polymerizations with the same or different monomer(s) to prepare multi-block copolymers.

Furthermore, since this is a radical polymerization, blocks can be prepared in essentially any order. One is not necessarily restricted to preparing block copolymers where the sequential polymerizing steps must flow from the least stabilized polymer intermediate to the most stabilized polymer intermediate, such as is the case in ionic polymerization. Thus it is possible to prepare a multi-block copolymer in which a polyacrylonitrile or a poly(meth)-acrylate block is prepared first, then a styrene or butadiene block is attached thereto, and so on.

Furthermore, there is no linking group required for joining the different blocks of the present block copolymer. One can simply add successive monomers to form successive blocks.

A plurality of specifically designed polymers and copolymers are accessible by the present invention, such as star and graft (co)polymers as described, inter alia, by C. J. Hawker in Angew. Chemie, 1995, 107, pages 1623-1627, dendrimers as described by K. Matyaszewski et al. in Macrmolecules 1996, Vol 29, No. 12, pages 41674171, graft (co)polymers as described by C. J. Hawker et al. in Macromol. Chem. Phys. 198, 155-166(1997), random copolymers as described by C. J. Hawker in Macromolecules 1996, 29, 2686-2688, or diblock and triblock copolymers as described by N. A. Listigovers in Macromolecules 1996, 29, 8992-8993.

The compounds of formula Ia, IIa and IIIa are novel. A further subject of the present invention is therefore a compound of formula Ia, IIa or IIIa

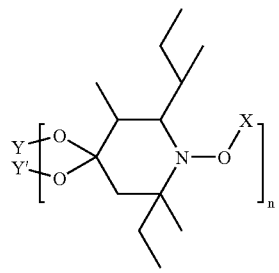
(Ia)

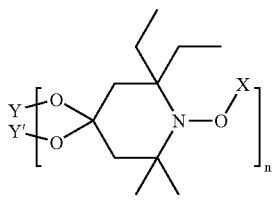
(IIa)

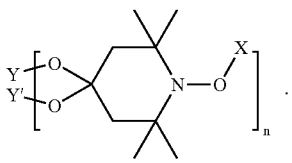
(IIIa)

wherein n is 1 or 2;

X is selected from the group consisting of —$CH_2$-phenyl, $CH_3$CH-phenyl, $(CH_3)_2$C-phenyl, $(C_5$-$C_6$cycloalkyl$)_2$CCN, 3-cyclohexenyl, 3-cyclopentenyl, $(CH_3)_2$CCN, —$CH_2$CH=$CH_2$, $CH_3$CH—CH=$CH_2$ ($C_1$-$C_4$alkyl)$CR_{20}$—C(O)-phenyl, ($C_1$-$C_4$)alkyl-$CR_{20}$—C(O)—($C_1$-$C_4$) alkoxy, ($C_1$-$C_4$)alkyl-$CR_{20}$—C(O)—($C_1$-$C_4$)alkyl, ($C_1$-$C_4$) alkyl-$CR_{20}$—C(O)—N-di($C_1$-$C_4$)alkyl, ($C_1$-$C_4$)alkyl-$CR_{20}$—C(O)—NH($C_1$-$C_4$)alkyl, ($C_1$-$C_4$)alkyl-$CR_{20}$—C(O)—$NH_2$, and a group of formula

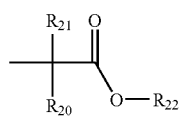

wherein $R_{20}$ is hydrogen or ($C_1$-$C_4$)alkyl, $R_{21}$ is hydrogen, $C_1$-$C_4$alkyl or phenyl and $R_{22}$ is $C_1$-$C_{12}$alkyl which is unsubstituted or substituted by OH or N($R_{20}$)($R_{21}$) or which is interrupted by O or $NR_{20}$;

if n is 1

Y and Y' are independently $C_1$-$C_{12}$alkyl, $C_3$-$C_{12}$alkenyl, $C_3$-$C_{12}$alkinyl, $C_5$-$C_8$cycloalkyl, phenyl, naphthyl, $C_7$-$C_9$phenylalkyl; or Y and Y' together form one of the bivalent groups —C($R_1$)($R_2$)—CH($R_3$)—, CH($R_1$)—$CH_2$—C($R_2$)($R_3$)—, —CH($R_2$)—$CH_2$—C($R_1$)($R_3$)—, —$CH_2$—C($R_1$)($R_2$)—CH($R_3$)—, o-phenylene, 1,2-cyclohexyliden, —$CH_2$—CH=CH—$CH_2$— or

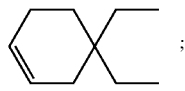

wherein $R_1$ is hydrogen, $C_1$-$C_{12}$alkyl, COOH, COO—($C_1$-$C_{12}$)alkyl or $CH_2OR_4$;

$R_2$ and $R_3$ are independently hydrogen, methyl ethyl, COOH or COO—($C_1$-$C_{12}$)alkyl;

$R_4$ is hydrogen, $C_1$-$C_{12}$alkyl, benzyl, or a monovalent acyl residue derived from an aliphatic, cycloaliphatic or aromatic monocarboxylic acid having up to 18 carbon atoms;

if n is 2

Y and Y' together form one of the tetravalent groups

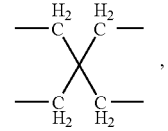

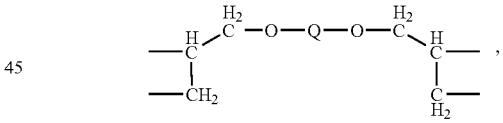

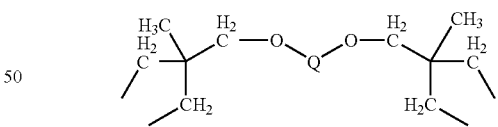

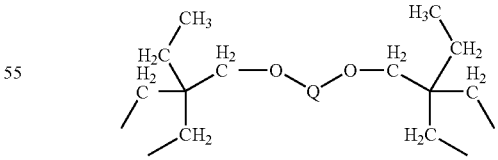

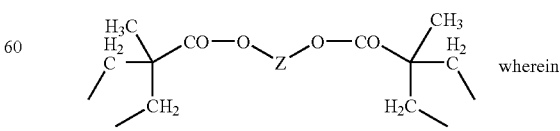
wherein

Q is a bisacyl residue which is derived from a $C_2$-$C_{12}$dicarboxylic acid or $C_1$-$C_{12}$alkylene; and Z is $C_1$-$C_{12}$alkylene; with the proviso that compounds A, B, C are excluded (A)
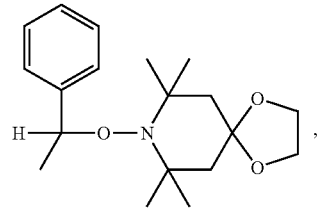

(B)
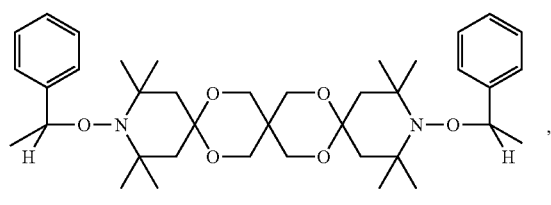

(C)
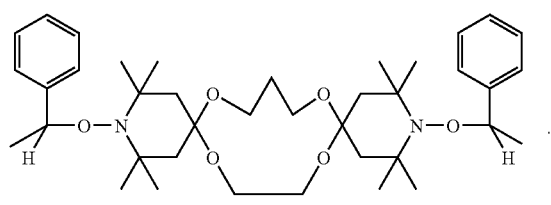

The definitions and preferrences given above apply also for the compounds.

The preparation of the compounds of the present invention is carried out according to known reaction steps. A general method for the preparation of the compounds of formula Ia, IIa, and IIIa starts from the 4-oxo compounds Xa or XIa which are described in GB 2335190 or from XIIa which is a known compound described for example in DE 2352127.

(Xa)
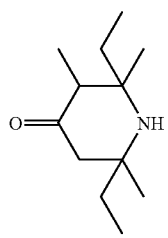

(XIa)
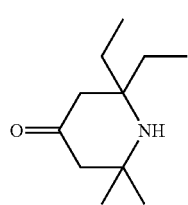

(XIIa)
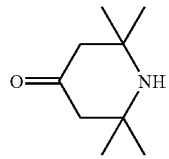

These starting compounds are reacted for example with suitable monoalcohols, diols or tetrafunctional alcohols to form intermediates of formula Xb, XIb or XIIb wherein Y, Y' and n are as defined above. Such ketalization reactions are well known in the art and the corresponding compounds are mostly known. The reaction is for example described in U.S. Pat. Nos. 3,790,525, 3,899,464, 4,007,158 and 4,105,626.

(Xb)
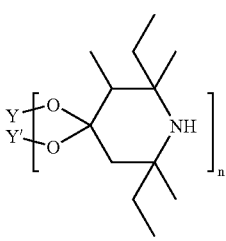

(XIb)
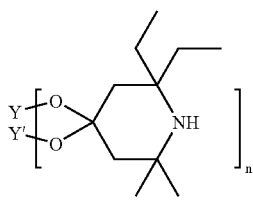

(XIIb)
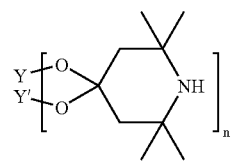

The compounds of formula Xb, XIb and XIIb are oxidized according to standard procedures to the corresponding nitroxides of formula Xc, XIc and XIIc, as for example described in GB 2335190 or WO 99/46261.

(Xc)
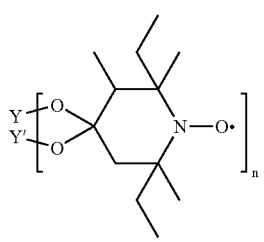

(XIc)
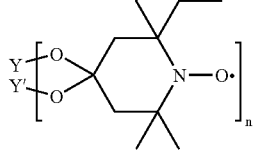

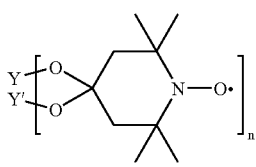
(XIIc)

The nitroxides are then coupled with a compound of formula HX under oxidative conditions. Suitable radicals X are as defined above. This coupling reaction is described for example in GB 2335190. Preferably the coupling reaction is carried out in the presence of a Cu(II) salt according to the method described in International Application No. PCT/EP01/05668.

These nitroxides can also be used as polymerization regulators in combination with a source of free radicals.

A further subject of the invention is therefore a polymerizable composition, comprising a) at least one ethylenically unsaturated monomer or oligomer;

b) a compound of formula Ib or IIb

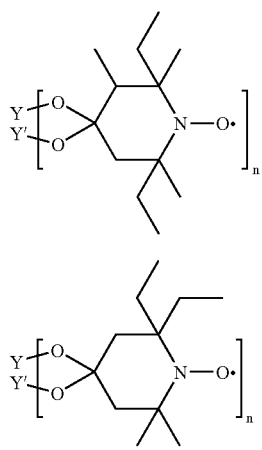
(Ib)

(IIb)

wherein n is 1 or 2;

if n is 1

Y and Y' are independently $C_1$-$C_{12}$alkyl, $C_3$-$C_{12}$alkenyl, $C_3$-$C_{12}$alkinyl, $C_5$-$C_8$cycloalkyl, phenyl, naphthyl, $C_7$-$C_9$phenylalkyl; or Y and Y' together form one of the bivalent groups —C($R_1$)($R_2$)—CH($R_3$)—, CH($R_1$)—CH$_2$—C($R_2$)($R_3$)—, —CH($R_2$)—CH$_2$—C($R_1$)$R_3$)—, —CH$_2$—C($R_1$)($R_2$)—CH($R_3$)—, o-phenylene, 1,2-cyclohexyliden, —CH$_2$—CH═CH—CH$_2$— or

wherein $R_1$ is hydrogen, $C_1$-$C_{12}$alkyl, COOH, COO—($C_1$-$C_{12}$)alkyl or CH$_2$OR$_4$;

$R_2$ and $R_3$ are independently hydrogen, methyl ethyl, COOH or COO—($C_1$-$C_{12}$)alkyl;

$R_4$ is hydrogen, $C_1$-$C_{12}$alkyl, benzyl, or a monovalent acyl residue derived from an aliphatic, cycloaliphatic or aromatic monocarboxylic acid having up to 18 carbon atoms;

if n is 2

Y and Y' together form one of the tetravalent groups

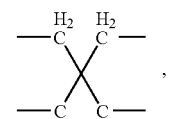

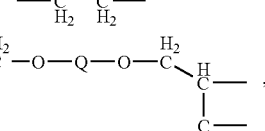

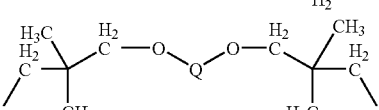

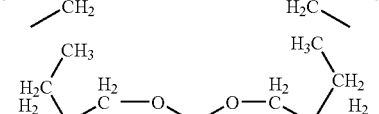

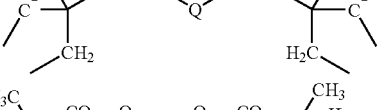
wherein

Q is a bisacyl residue which is derived from a $C_2$-$C_{12}$dicarboxylic acid or $C_1$-$C_{12}$alkylene; and Z is $C_1$-$C_{12}$alkylene; and c) a source of free radicals capable of initiating polymerization of ethylenically unsaturated monomers.

Preferred is a polymerizable composition wherein in the compound of formula Ib or IIb n is 1

Y and Y' are independently $C_1$-$C_{12}$alkyl, $C_3$-$C_{12}$alkenyl, phenyl or benzyl; or Y and Y' together form one of the bivalent groups —C($R_1$)($R_2$)—CH($R_3$)—, CH($R_1$)—CH$_2$—C($R_2$)($R_3$)—, —CH($R_2$)—CH$_2$—C($R_1$)($R_3$)—, —CH$_2$—C($R_1$)($R_2$)—CH($R_3$)—, —CH$_2$—CH═CH—CH$_2$— or; wherein $R_1$ is hydrogen, $C_1$-$C_{12}$alkyl, COO—($C_1$-$C_{12}$)alkyl or CH$_2$OR$_4$;

$R_2$ and $R_3$ are independently hydrogen, methyl ethyl, or COO—($C_1$-$C_{12}$)alkyl;

$R_4$ is hydrogen, $C_1$-$C_{12}$alkyl, benzyl, or a monovalent acyl residue derived from an aliphatic, cycloaliphatic or aromatic monocarboxylic acid having up to 12 carbon atoms.

Specific nitroxide compounds useful in the present invention are given in Tables 4 and 5.

TABLE 4
Compounds according to formula (Ib)
1 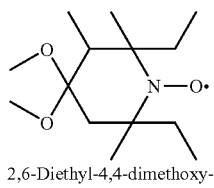
2,6-Diethyl-4,4-dimethoxy-
2,3,6-trimethyl-piperidin-1-
oxyl
2 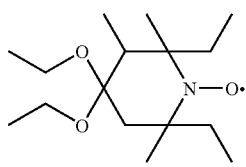
4,4-Diethoxy-2,6-diethyl-
2,3,6-trimethyl-piperidin-1-
oxyl
3 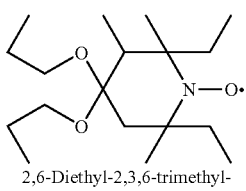
2,6-Diethyl-2,3,6-trimethyl-
4,4-dipropoxy-piperidin-1-
oxyl
4 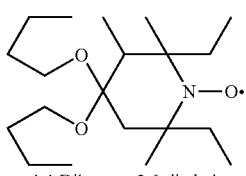
4,4-Dibutoxy-2,6-diethyl-
2,3,6-trimethyl-piperidin-1-
oxyl
5 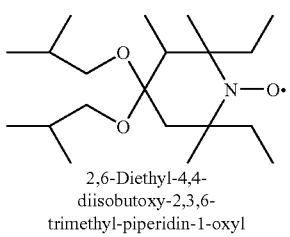
2,6-Diethyl-4,4-
diisobutoxy-2,3,6-
trimethyl-piperidin-1-oxyl
6 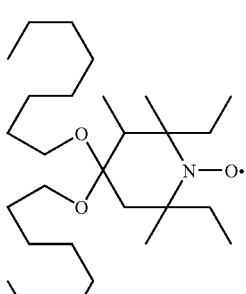
2,6-Diethyl-2,3,6-trimethyl-
4,4-bis-octyloxy-piperidin-1-
oxyl TABLE 4-continued
| Compounds according to formula (Ib) |
7 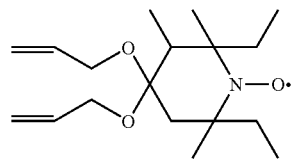
4,4-Bis-allyloxy-2,6-diethyl-
2,3,6-trimethyl-piperidin-1-
oxyl
8 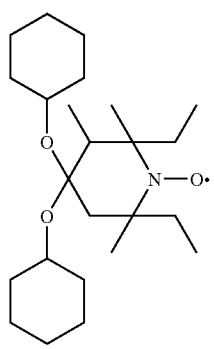
4,4-Bis-cyclohexyloxy-2,6-
diethyl-2,3,6-trimethyl-
piperidin-1-oxyl
9 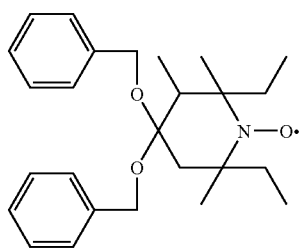
4,4-Bis-benzyloxy-2,6-
diethyl-2,3,6-trimethyl-
piperidin-1-oxyl
10 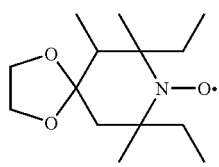
7,9-Diethyl-6,7,9-trimethyl-
1,4-dioxa-8-aza-
spiro[4.5]decan-8-oxyl
11 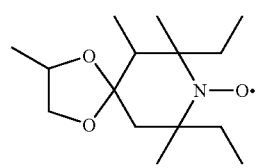
7,9-Diethyl-6,7,9-
tetramethyl-1,4-dioxa-8-
aza-spiro[4.5]decan-8-oxyl TABLE 4-continued
Compounds according to formula (Ib)
12
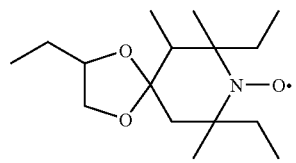
2,7,9-Triethyl-6,7,9-
trimethyl-1,4-dioxa-8-aza-
spiro[4.5]decan-8-oxyl
13
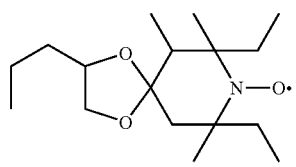
7,9-Diethyl-6,7,9-trimethyl-
2-propyl-1,4-dioxa-8-aza-
spiro[4.5]decan-8-oxyl
14
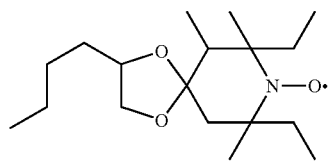
2-Butyl-7,9-diethyl-6,7,9-
trimethyl-1,4-dioxa-8-aza-
spiro[4.5]decan-8-oxyl
15
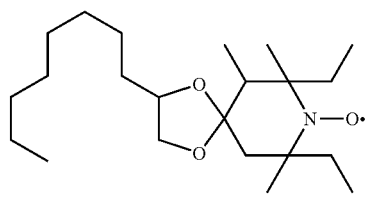
7,9-Diethyl-6,7,9-trimethyl-
2-octyl-1 14-dioxa-8-aza-
spiro[4.5]decan-8-oxyl
16
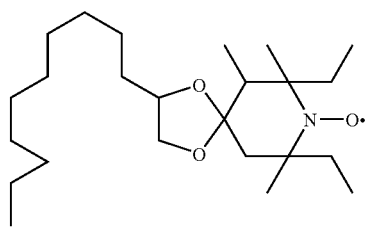
2-Decyl-7,9-diethyl-6,7,9-
trimethyl-1,4-dioxa-8-aza-
spiro[4.5]decan-8-oxyl TABLE 4-continued
Compounds according to formula (Ib)
17
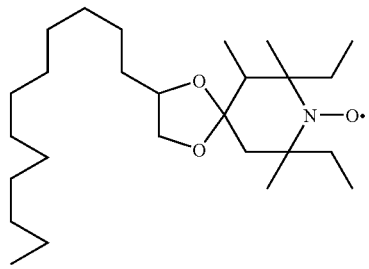
2-Dodecyl-7,9-diethyl-
6,7,9-trimethyl-1,4-dioxa-
8-aza-spiro[4.5]decan-8-
oxyl
18
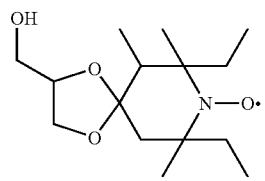
7,9-Diethyl-2-
hydroxymethyl-6,7,9-
trimethyl-1,4-dioxa-8-aza-
spiro[4.5]decan-8-oxyl
19
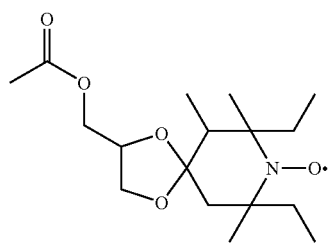
Acetic acid 7,9-diethyl-
6,7,9-trimethyl-1,4-dioxa-8-
aza-spiro[4.5]dec-2-
ylmethyl ester-8-oxyl
20
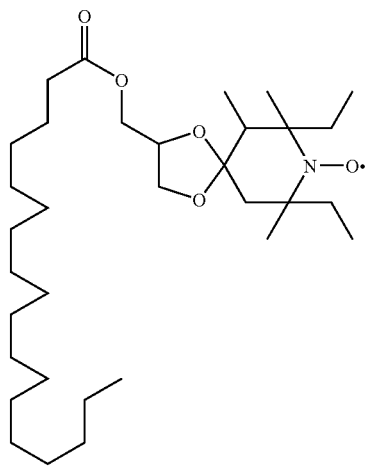
Octadecanoic acid 7,9-
diethyl-6,7,9-trimethyl-1,4-
dioxa-8-aza-spiro[4.5]dec-
2-ylmethyl ester-8-oxyl TABLE 4-continued
Compounds according to formula (Ib)
21 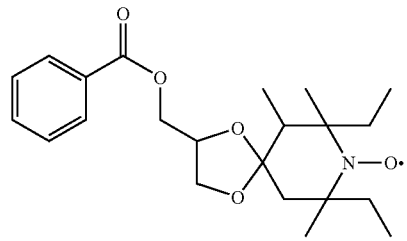
Benzoic acid 7,9-diethyl-
6,7,9-trimethyl-1,4-dioxa-8-
aza-spiro[4.5]dec-2-
ylmethyl ester-8-oxyl
22 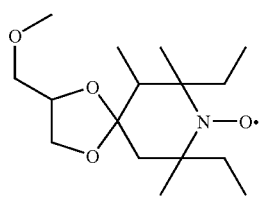
7,9-Diethyl-2-
methoxymethyl-6,7,9-
trimethyl-1,4-dioxa-8-aza-
spiro[4.5]decan-8-oxyl
23 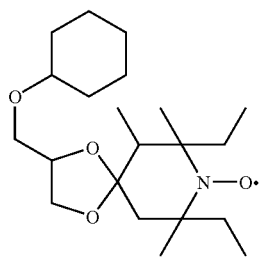
2-Cyclohexyloxymethyl
7,9-diethyl-6,7,9-trimethyl-
1,4-dioxa-8-aza-
spiro[4.5]decan-8-oxyl
24 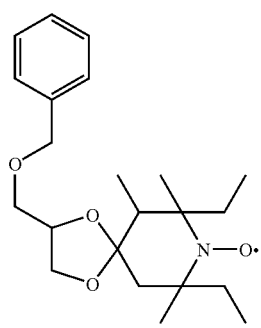
2-Benzyloxymethyl-7,9-
diethyl-6,7,9-trimethyl-1,4-
dioxa-8-aza-
spiro[4.5]decan-8-oxyl TABLE 4-continued
| Compounds according to formula (Ib) |
| --- |
25 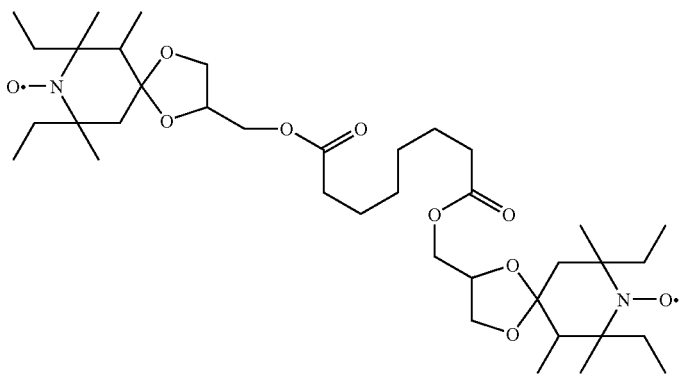
Octanedioic acid bis-(7,9-diethyl-8-oxyl-6,7,9-trimethyl-1,4-dioxa-8-aza-spiro[4.5]dec-2-ylmethyl)-ester
26 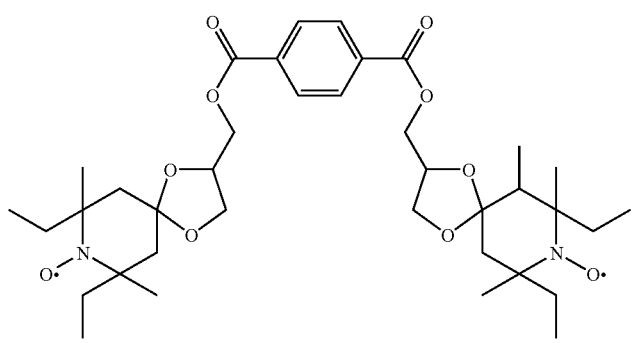
Terephthalic acid bis-(7,9-diethyl-8-oxyl-6,7,9-trimethyl-1,4-dioxa-8-aza-spiro[4.5]dec-2-ylmethyl) ester
27 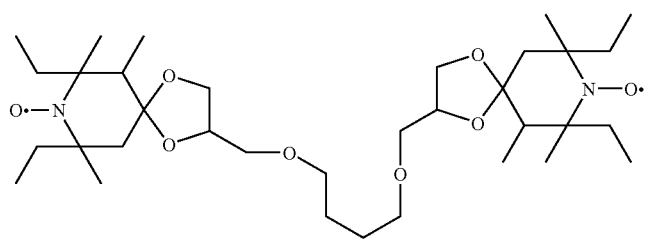
1,4-Bis-{[7,9-diethyl-6,7,9-trimethyl-8-oxyl-1,4-dioxa-azaspiro[4.5]dec-2-yl]-methyloxy}-butane
28 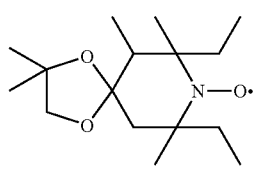
7,9-Diethyl-2,2,6,7,9-pentamethyl-1,4-dioxa-8-aza-spiro[4.5]decan-8-oxyl TABLE 4-continued Compounds according to formula (Ib)

29 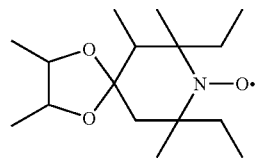

7,9-Diethyl-2,3,6,7,9-
pentamethyl-1,4-dioxa-8-
aza-spiro[4.5]decan-8-oxyl

30 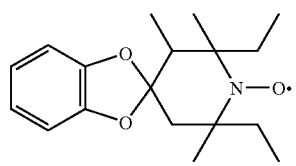

2,3-Benzo-7,9-diethyl-
6,7,9-trimethyl-8-oxyl-1,4-
dioxa-8-aza-
spiro[4.5]decane 31 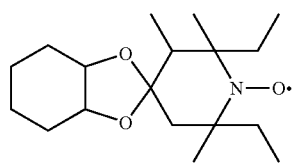

2,3-Cyclohexano-7,9-
diethyl-6,7,9-trimethyl-8-
oxyl-1,4-dioxa-8-aza-
spiro[4.5]decane 32 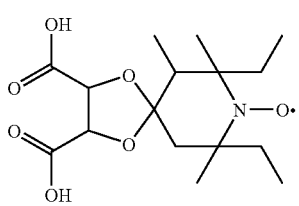

7,9-Diethyl-6,7,9-trimethyl-
1,4-dioxa-8-aza-
spiro[4.5]decane-2,3-
dicarboxylic acid-8-oxyl 33 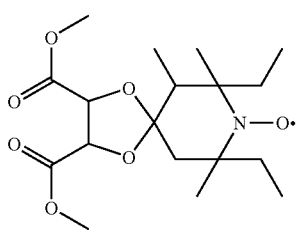

7,9-Diethyl-6,7,9-trimethyl-
1,4-dioxa-8-aza-
spiro[4.5]decane-2,3-
dicarboxylic acid dimethyl
ester-8-oxyl TABLE 4-continued Compounds according to formula (Ib)

34 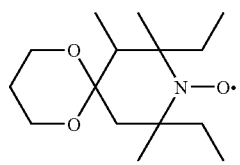
8,10-Diethyl-7,8,10-
trimethyl-1,5-dioxa-9-aza-
spiro[5.5]undecan-9-oxyl 35 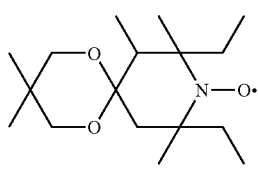
8,10-Diethyl-3,3,7,8,10-
pentamethyl-1,5-dioxa-9-
aza-spiro[5.5]undecan-9-
oxyl 36 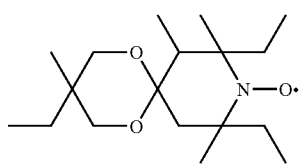
3,8,10-Triethyl-3,7,8,10-
tetramethyl-1,5-dioxa-9-
aza-spiro[5.5]undecan-9-
oxyl 37 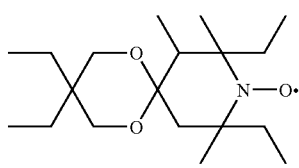
3,3,8,10-Tetraethyl-7,8,10-
trimethyl-1,5-dioxa-9-aza-
spiro[5.5]undecan-9-oxyl 38 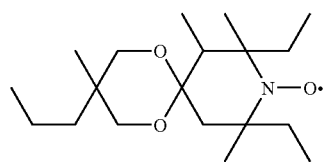
8,10-Diethyl-3,7,8,10-
tetramethyl-3-propyl-1,5-
dioxa-9-aza-
spiro[5.5]undecan-9-oxyl 39 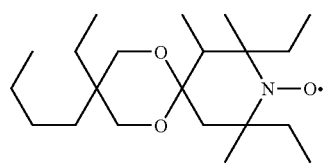
3-Butyl-3,8,10-triethyl-
7,8,10-trimethyl-1,5-dioxa-
9-aza-spiro[5.5]undecan-9-
oxyl TABLE 4-continued Compounds according to formula (Ib)

40 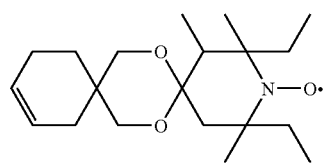

2,4-Diethyl-1,2,4-trimethyl-
7,16-dioxa-3-aza-
dispiro[5.2.5.2]hexadec-11-
en-3-oxyl 41 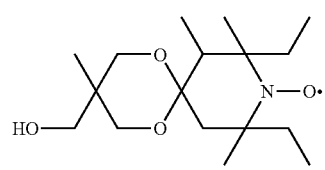

8,10-Diethyl-3-
hydroxymethyl-3,7,8,10-
tetramethyl-1,5-dioxa-9-
aza-spiro[5.5]undecan-9-
oxyl 42 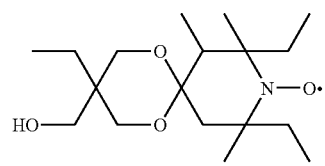

3,8,10-Triethyl-3-
hydroxymethyl-7,8,10-
trimethyl-1,5-dioxa-9-aza-
spiro[5.5]undecan-9-oxyl 43 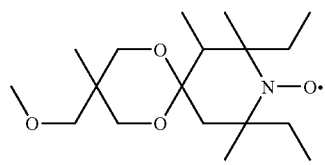

8,10-Diethyl-3-
methoxymethyl-3,7,8,10-
tetramethyl-1,5-dioxa-9-
aza-spiro[5.5]undecan-9-
oxyl 44 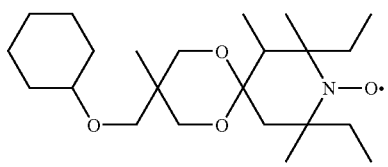

3-Cyclohexyloxymethyl-
8,10-diethyl-3,7,8,10-
tetramethyll 5-dioxa-9-
aza-spiro[5.5]undecan-9-
oxyl TABLE 4-continued
Compounds according to formula (Ib)
45
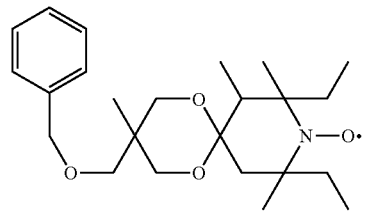
3-Benzyloxymethyl-8,10-
diethyl-3,7,8,10-
tetramethyl-1,5-dioxa-9-
aza-spiro[5.5]undecan-9-
oxyl
46
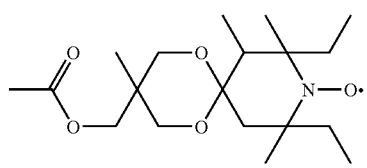
Acetic acid 8,10-diethyl-
3,7,8,10-tetramethyl-1,5-
dioxa-9-aza-
spiro[5.5]undec-3-ylmethyl
ester-9-oxyl
47
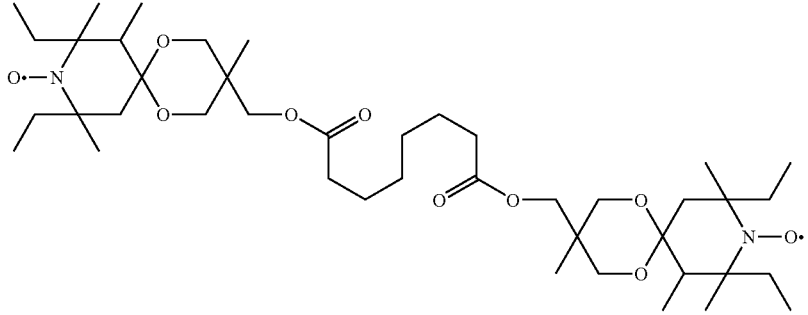
Octanedioic acid bis-
(8,10-diethyl-9-oxyl-
3,7,8,10-tetramethyl-1,5-
dioxa-9-aza-
spiro[5.5]undec-3-
ylmethyl) ester
48
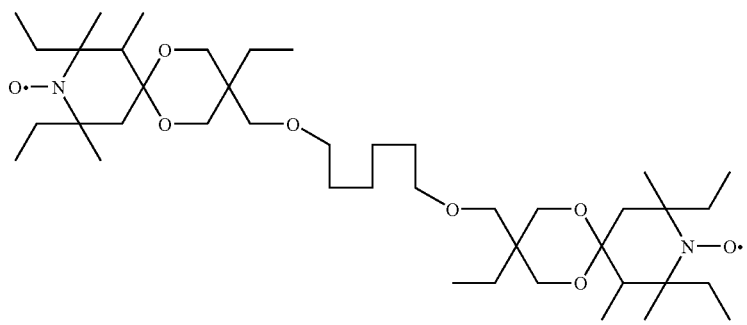
1,6-Bis-{3,8,10-triethyl-
7,8,10-trimethyl-9-oxyl-1,5-
dioxa-9-
azaspiro[5.5]undec-3-
methyloxy}-hexane TABLE 4-continued Compounds according to formula (Ib)

49
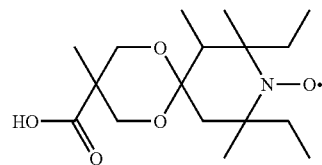
8,10-Diethyl-3,7,8,10-
tetramethyl-1,5-dioxa-9-
aza-spiro[5.5]undecane-3-
carboxylic acid-9-oxyl 50
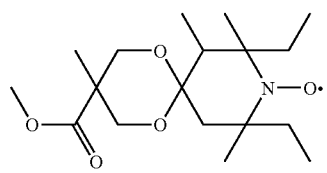
8,10-Diethyl-3,7,8,10-
tetramethyl-1,5-dioxa-9-
aza-spiro[5.5]undecane-3-
carboxylic acid methyl
ester-9-oxyl 51
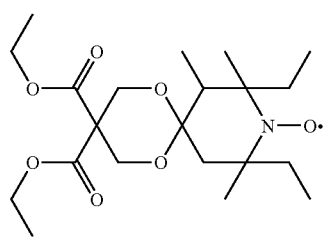
8,10-Diethyl-7,8,10-
trimethyl-1,5-dioxa-9-aza-
spiro[5.5]undecane-3,3-
dicarboxylic acid diethyl
ster-9-oxyl 52
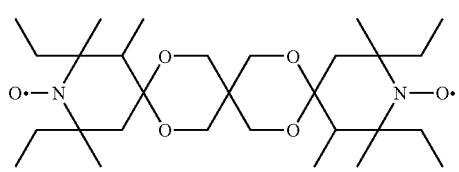
3,3-Bisspiro-{8,10-diethyl-
7,8,10-trimethyl-9-oxyl-1,5-
dioxa-9-aza-
spiro[5.5]undecane}

53
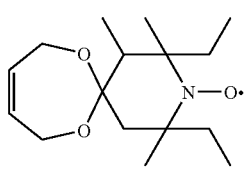
2,4-Diethyl-1,2,4-trimethyl-
7,12-dioxa-3-aza-
spiro[5.6]dodec-9-en-3-
oxyl

TABLE 4-continued

Compounds according to formula (Ib)

54

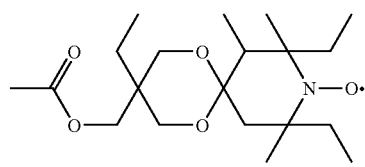

Acetic acid 3,8,10-triethyl-
7,8,10-trimethyl-1,5-dioxa-
9-aza-spiro[5.5]undec-3-yl-
methyl ester-9-oxyl

55

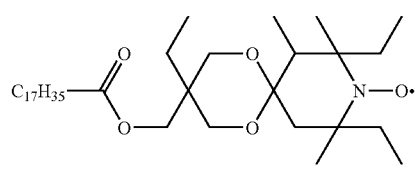

Octadecanoic acid 3,8,10-
triethyl-7,8,10-trimethyl-1,5-
dioxa-9-aza-spiro[5.5]un-
dec-3-ylmethyl ester-9-oxyl

TABLE 5

Compounds according to formula (IIb)

1

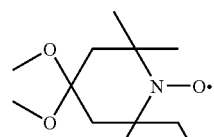

2,2-Diethyl-4,4-dimethoxy-
6,6-dimethyl-piperidin-1-
oxyl

2

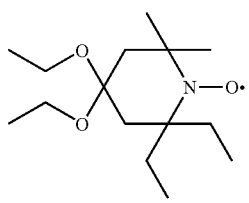

4,4-Diethoxy-2,2-diethyl-
6,6-dimethyl-piperidin-1-
oxyl

3

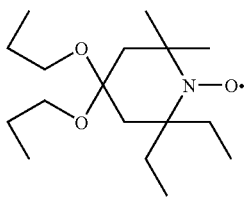

2,2-Diethyl-6-6-dimethyl-4,4-
dipropoxy-piperidin-1-oxyl

TABLE 5-continued
Compounds according to formula (IIb)
4
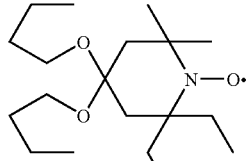
4,4-Dibutoxy-2,2-diethyl-
6,6-dimethyl-piperidin-1-
oxyl
5
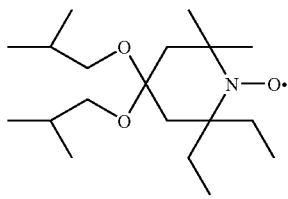
2,2-Diethyl-4,4-diisobutoxy-
6,6-dimethyl-piperidin-1-
oxyl
6
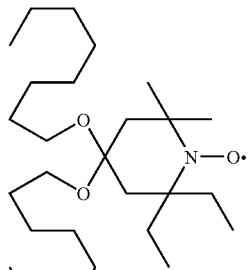
2,2-Diethyl-6,6-dimethyl-4,4-
bis-octyloxy-piperidin-1-oxyl
7
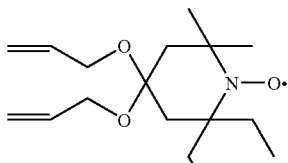
4,4-Bis-allyloxy-2,2-diethyl-
6,6-dimethyl-piperidin-1-
oxyl
8
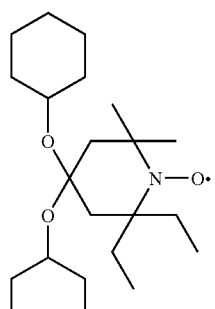
4-Bis-cyclohexyloxy-2,2-
diethyl-6,6-dimethyl-
piperidin-1-oxyl TABLE 5-continued
Compounds according to formula (IIb)
9 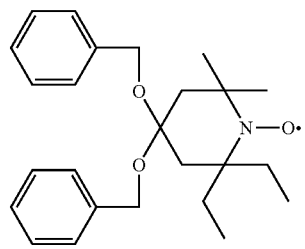
4,4-Bis-benzyloxy-2-2-
diethyl-6,6-dimethyl-
piperidin-1-oxyl
10 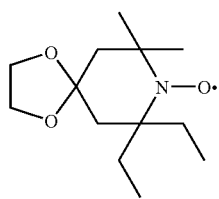
7,7-Diethyl-9,9-dimethyl-
1,4-dioxa-8-aza-
spiro[4.5]decan-8-oxyl
11 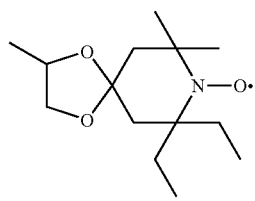
7,7-Diethyl-2,9,9-trimethyl-
1,4-dioxa-8-aza-
spiro[4.5]decan-8-oxyl
12 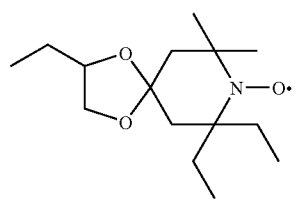
2,7,7-Thethyl-9,9-dimethyl-
1,4-dioxa-8-aza-
spiro[4.5]decan-8-oxyl
13 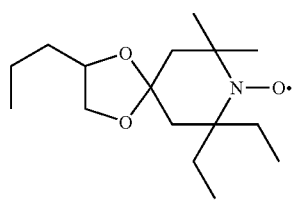
7,7-Diethyl-9,9-dimethyl-2-
propyl-1,4-dioxa-8-aza-
spiro[4.5]decan-8-oxyl TABLE 5-continued
Compounds according to formula (IIb)
14
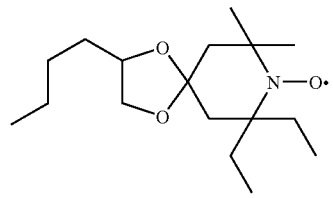
2-Butyl-7,7-diethyl-9,9-
dimethyl-1 14-dioxa-8-aza-
spiro[4.5]decan-8-oxyl
15
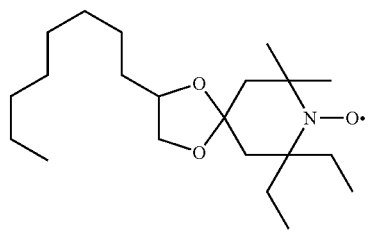
7,7-Diethyl-9,9-dimethyl-2-
octyl-1,4-dioxa-8-aza-
spiro[4.5]decan-8-oxyl
16
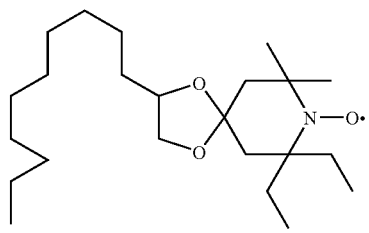
2-Decyl-7,7-diethyl-9,9-
dimethyl-1,4-dioxa-8-aza
spiro[4.5]decan-8-oxyl
17
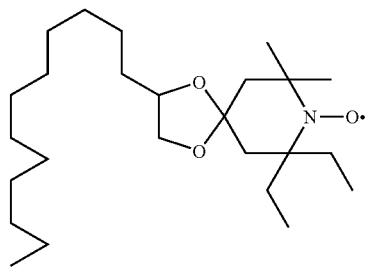
2-Dodecyl-7,7-diethyl-9,9-
dimethyl-1,4-dioxa-8-aza-
spiro[4.5]decan-8-oxyl
18
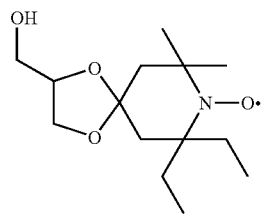
7,7-Diethyl-2-hydroxymethyl-
9,9-dimethyl-1,4-dioxa-8-aza
spiro[4.5]decan-8-oxyl TABLE 5-continued
Compounds according to formula (IIb)
19
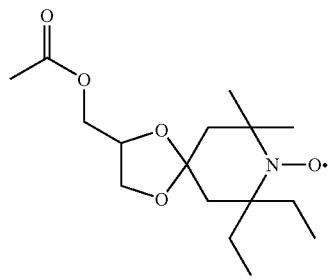
Acetic acid 7,7-diethyl-9,9-
dimethyl-1 4-dioxa-8-aza-
spiro[4.5]dec-2-ylmethyl
ester-8-oxyl
20
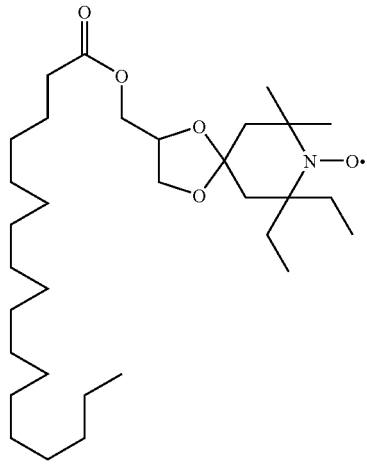
Octadecanoic acid 7,7-
diethyl-9,9-dimethyl-1,4-
dioxa-8-aza-spiro[4.5]dec-
2-ylmethyl ester-8-oxyl
21
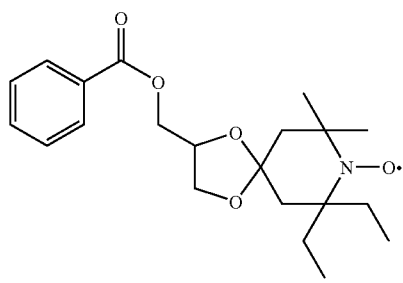
Benzoic acid 7,7-diethyl-9,9-
dimethyl-1,4-dioxa-8-aza-
spiro[4.5]dec-2-ylmethyl
ester-8-oxyl
22
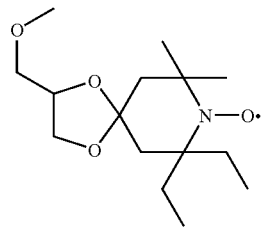
7,7-Diethyl-2-
methoxymethyl-9,9-
dimethyl-1,4-dioxa-8-aza-
spiro[4.5]decan-8-oxyl TABLE 5-continued
| Compounds according to formula (IIb) |
23
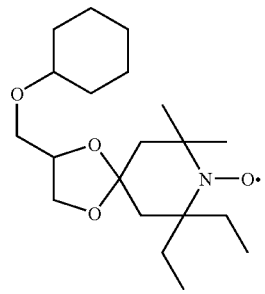
2-Cyclohexyloxymethyl-7,7-
diethyl-9,9-dimethyl-1,4-
dioxa-8-aza-
spiro[4.5]decan-8-oxyl
24
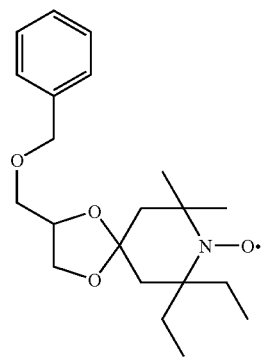
2-Benzyloxymethyl-7,7-
diethyl-9,9-dimethyl-1,4-
dioxa-8-aza-spiro[4.5]decan-
8-oxyl
25
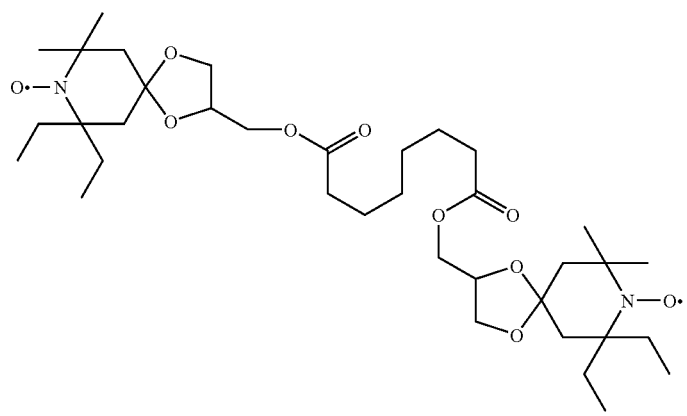
Octanedioic acid bis-(7,7-
diethyl-8-oxyl-9,9-dimethyl-
1,4-dioxa-8-aza-
spiro[4.5]dec-2-ylmethyl)
ester TABLE 5-continued
Compounds according to formula (IIb)
26 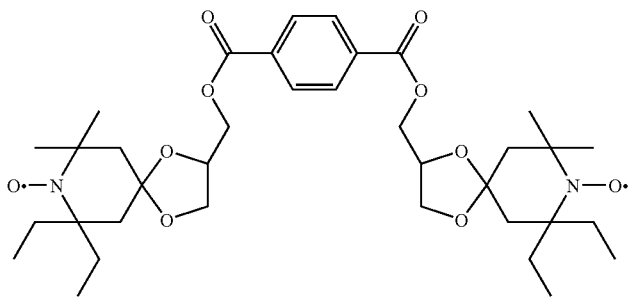
Terephthalic acid bis-(7,7-
diethyl-8-oxyl-9,9-dimethyl-
1,4-dioxa-8-aza-
spiro[4.5]dec-2-ylmethyl)
ester
27 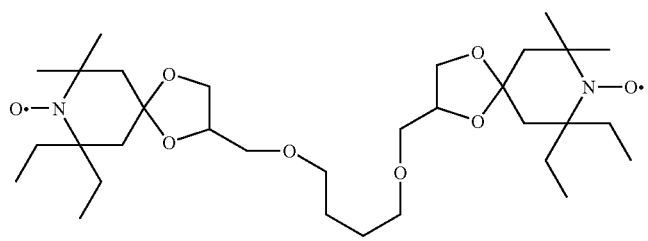
1,4-Bis-{[7,7-diethyl-9,9-
dimethyl-8-oxyl-1,4-dioxa-8-
aza-spiro[4.5]dec-2-yl]-
methyloxy}-butane
28 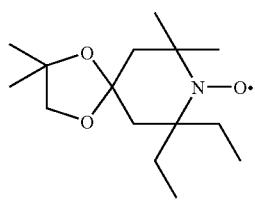
7,7-Diethyl-2,2,9,9-
tetramethyl-1,4-dioxa-8-
aza-spiro[4.5]decan-8-oxyl
29 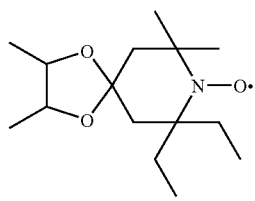
7,7-Diethyl-2,3,9,9-
tetramethyl-1,4-dioxa-8-
aza-spiro[4.5]decan-8-oxyl
30 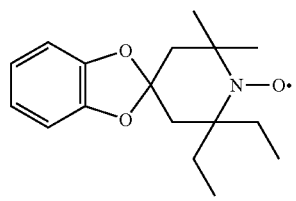
2,3-Benzo-7,7-diethyl-9,9-
dimethyl-8-oxyl-1,4-dioxa-8-
aza-spiro[4.5]decane TABLE 5-continued
Compounds according to formula (IIb)
31 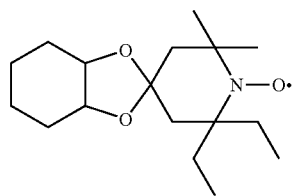
2,3-Cyclohexano-7,7-
diethyl-9,9-dimethyl-8-oxyl-
1,4-dioxa-8-azaspiro
[4.5]decane
32 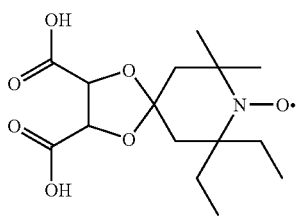
7,7-Diethyl-9,9-dimethyl-
1,4-dioxa-8-aza-
spiro[4.5]decane-2,3-
dicarboxylic acid-8-oxyl
33 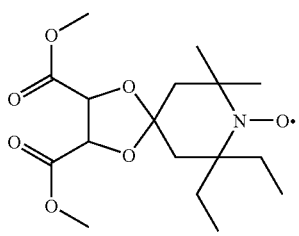
7,7-Diethyl-9,9-dimethyl-1,4-
dioxa-8-aza-
spiro[4.5]decane-2,3-
dicarboxylic acid dimethyl
ester-8-oxyl
34 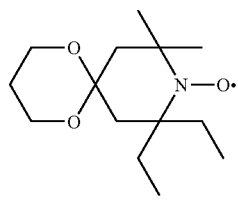
8,8-Diethyl-10,10-dimethyl-
1,5-dioxa-9-aza-
spiro[5.5]undecan-9-oxyl
35 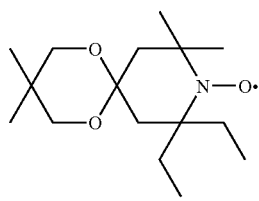
8,8-Diethyl-3,3,10,10-
etramethyl-1,5-dioxa-9-
aza-spiro[5.5]undecan-9-
oxyl TABLE 5-continued
Compounds according to formula (IIb)
36 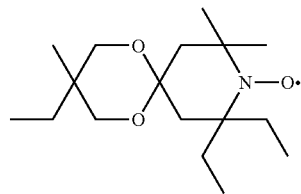
3,8,8-Triethyl-3,10,10-
trimethyl-1,5-dioxa-9-aza-
spiro[5.5]undecan-9-oxyl
37 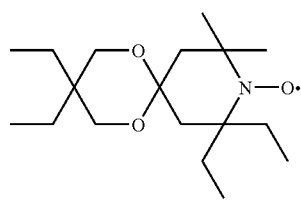
3,3,8,8-Tetraethyl-10,10-
dimethyl-1,5-dioxa-9-aza-
spiro[5.5]undecan-9-oxyl
38 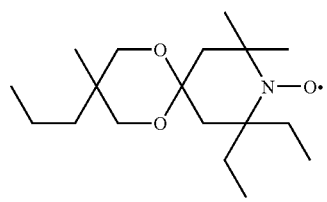
8,8-Diethyl-3,10,10-
trimethyl-3-propyl-1,5-
dioxa-9-aza-
spiro-5.5]undecan-9-oxyl
39 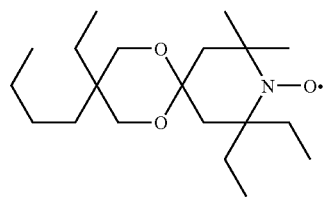
3-Butyl-3,8,8-triethyl-10,10-
dimethyl-1,5-dioxa-9-aza-
spiro[5.5]undecan-9-oxyl
40 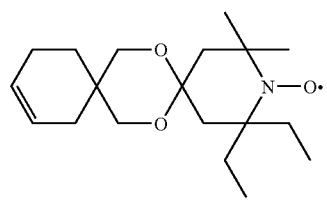
2,2-Diethyl-4,4-dimethyl-
7,16-dioxa-3-aza-
dispiro[5.2.5.2]hexadec-11-
en-3-axyl TABLE 5-continued Compounds according to formula (IIb)

41 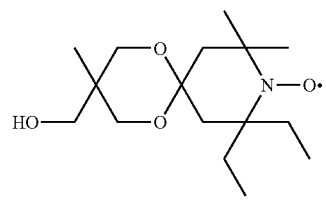

8,8-Diethyl-3-
hydroxymethyl-3,10,10-
trimethyl-1,5-dioxa-9-aza-
spiro[5.5]undecan-9-oxyl 42 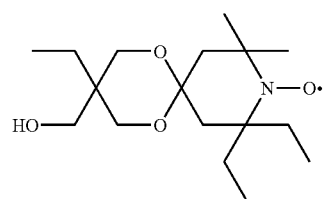

3,8,8-Triethyl-3-
hydroxyniethyl-10,10-
dimethyl-1,5-dioxa-9-aza-
spiro[5.5]undecan-9-oxyl 43 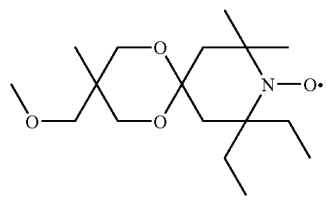

8,8-Diethyl-3-
methoxymethyl-3,10,10-
trimethyl-1,5-dioxa-9-aza-
spiro[5.5]undecan-9-oxyl 44 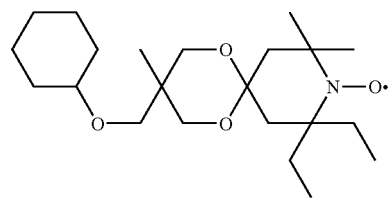

3-Cyclohexyloxymethyl-8,8-
diethyl-3,10,10-trimethyl-
1,5-dioxa-9-aza-
spiro[5.5]undecan-9-oxyl 45 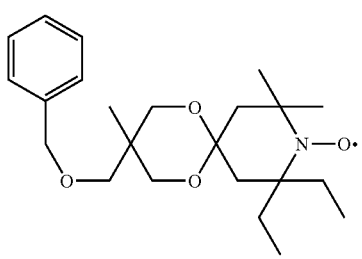

3-Benzyloxymethyl-8,8-
diethyl-3,10,10-trimethyt-1,5-
dioxa-9-aza-
spiro[5.5]undecan-9-oxyl TABLE 5-continued
Compounds according to formula (IIb)
46
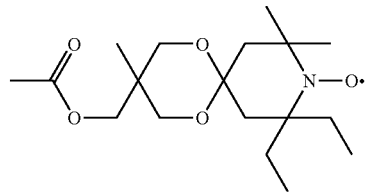
Acetic acid 8,8-diethyl-
3,10,10-trimethyl-1,5-dioxa-
9-aza-spiro[5.5]undec-3-
ylmethyl ester-9-oxyl
47
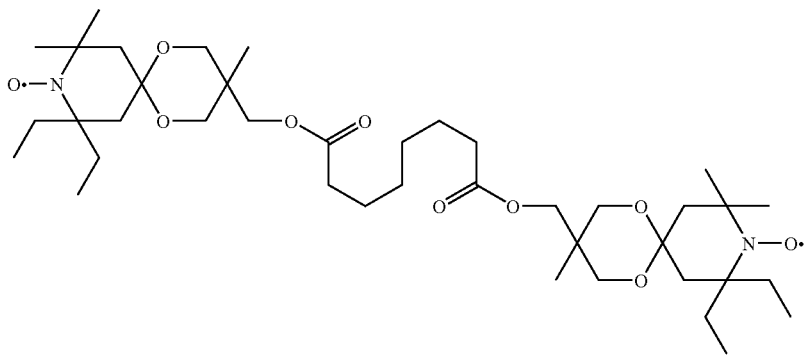
Octanedioic acid bis-(8,8-
diethyl-9oxyl-3,10,10-
trimethyl-1,5-dioxa-9-aza-
spiro[5.5]undec-3-ylmethyl)
ester
48
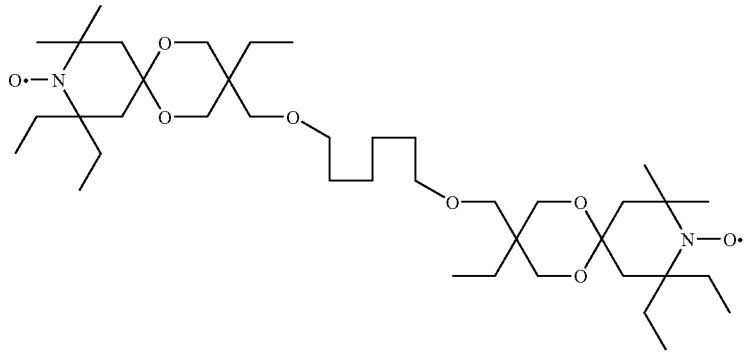
1,6-Bis{[3,8,8-triethyl-10,10-
dimethyl-9-oxyl-1,5-dioxa-9-
aza-spiro[5.5]undec-3-yl]-
methyloxy}-hexane
49
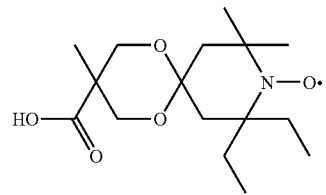
8,8-Diethyl-3,10,10-
trimethyt-1,5-dioxa-9-aza-
spiro[5.5]undecane-3-
carboxylic acid-9-oxyl TABLE 5-continued
Compounds according to formula (IIb)
50 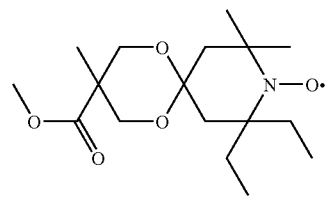
8,8-Diethyl-3,10,10-
trimethyl-1,5-dioxa-9-aza-
spiro[5.5]undecane-3-
carboxylic acid methyl
ester-9-oxyl
51 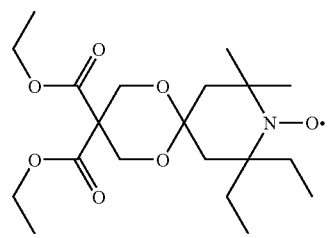
8,8-Diethyl-10,10-dimethyl-
1,5-dioxa-9-aza-
spiro[5.5]undecane-3,3-
dicarboxylic acid diethyl
ester-9-oxyl
52 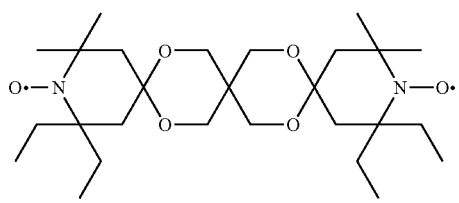
3,3-Bisspiro{8,8-diethyl-
10,10-dimethyl-9-oxyl-1,5-
dioxa-9-aza-
spiro[5.5]undecane}
53 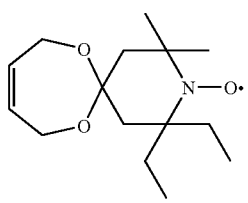
2,2-Diethyl-4,4-dimethyl-
7,12-dioxa-3-aza-
spiro[5.6]dodec-9-en-3-oxyl The compounds of Table 4, and 5 are particularly preferred.

Most preferred are the following compounds.

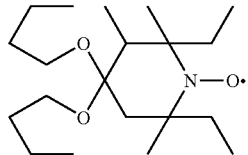

4,4-Dibutoxy-2,6-diethyl-2,3,6-trimethyl-piperidin-1-oxyl (Tab. 4, No. 4)

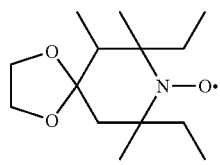

7,9-Diethyl-6,7,9-trimethyl-1,4-dioxa-8-aza-spiro[4.5]decan-8-oxyl (Tab. 4, No. 10)

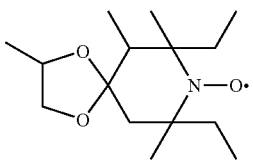

7,9-Diethyl-2,6,7,9-tetramethyl-1,4-dioxa-8-aza-spiro[4.5]decan-8-oxyl (Tab. 4, No. 11)

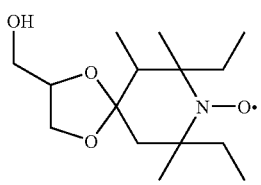

7,9-Diethyl-2-hydroxymethyl-6,7,9-trimethyl-1,4-dioxa-8-aza-spiro[4.5]decan-8-oxyl (Tab. 4, No. 18)

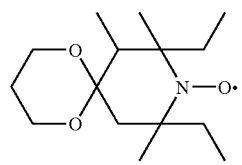

8,10-Diethyl-7,8,10-trimethyl-1,5-dioxa-9-aza-spiro[5.5]undecan-9-oxyl (Tab. 4, No. 34)

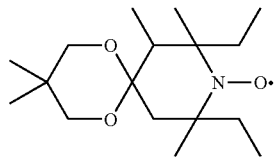

8,10-Diethyl-3,3,7,8,10-pentamethyl-1,5-dioxa-9-aza-spiro[5.5]undecan-9-oxyl (Tab. 4, No. 35)

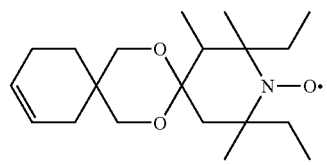

2,4-Diethyl-1,2,4-trimethyl-7,16-dioxa-3-aza-dispiro[5.2.5.2]hexadec-11-en-3-oxyl (Tab. 4, No. 40)

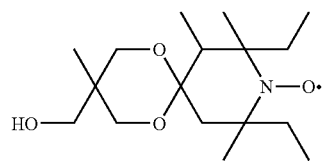

8,10-Diethyl-3-hydroxymethyl-3,7,8,10-tetramethyl-1,5-dioxa-9-aza-spiro[5.5]undecan-9-oxyl (Tab. 4, No. 41)

The source of radicals may be a bis-azo compound, a peroxide or a hydroperoxide.

The production of C-centered radicals is described, inter alia, in Houben Weyl, Methoden der Organischen Chemie, Vol. E 19a, pages 60-147. These methods can be applied in general analogy.

Preferably, the source of radicals is 2,2'-azobisisobutyronitrile, 2,2'-azobis(2-methylbutyronitrile), 2,2'-azobis(2,4dimethylvaleronitrile), 2,2'-azobis(4-methoxy-2,4-dimethylvaleronitrile), 1,1'-azobis(1-cyclohexanecarbonitrile), 2,2'-azobis(isobutyramide)dihydrate, 2-phenylazo-2,4-dimethylmethoxyvaleronitrile, dimethyl-2,2'-azobisisobutyrate, 2-(carbamoylazo)isobutyronitrile, 2,2'-azobis(2,4,4-trimethylpentane), 2,2'-azobis(2-methylpropane), 2,2'-azobis(N,N'-dimethyleneisobutyramidine), free base or hydrochloride, 2,2'-azobis(2-amidinopropane), free base or hydrochloride, 2,2'-azobis{2-methyl-N-[1,1-bis(hydroxymethyl)ethyl]propionamide} or 2,2'-azobis{2-methyl-N-[1,1-bis(hydroxymethyl)-2-hydroxyethyl]propionamide.

Preferred peroxides and hydroperoxides are acetyl cyclohexane sulphonyl peroxide, diisopropyl peroxy dicarbonate, t-amyl perneodecanoate, t-butyl perneodecanoate, t-butyl perpivalate, t-amylperpivalate, bis(2,4-dichlorobenzoyl)peroxide, diisononanoyl peroxide, didecanoyl peroxide, dioctanoyl peroxide, dilauroyl peroxide, bis (2-methylbenzoyl) peroxide, disuccinic acid peroxide, diacetyl peroxide, dibenzoyl peroxide, t-butyl per 2-ethylhexanoate, bis-(4-chlorobenzoyl)-peroxide, t-butyl perisobutyrate, t-butyl permaleinate, 1,1-bis(t-butylperoxy)3,5,5-trimethylcyclohexane, 1,1-bis(t-butylperoxy)cyclohexane, t-butyl peroxy isopropyl carbonate, t-butyl perisononaoate, 2,5-dimethylhexane 2,5- dibenzoate, t-butyl peracetate, t-amyl perbenzoate, t-butyl perbenzoate, 2,2-bis(t-butylperoxy)butane, 2,2 bis (t-butylperoxy)propane, dicumyl peroxide, 2,5-dimethylhexane-2,5-di-t-butylperoxide, 3-t-butylperoxy 3-phenylphthalide, di-t-amyl peroxide, α, α'-bis(t-butylperoxy isopropyl)benzene, 3,5-bis(t-butylperoxy)3,5-dimethyl 1,2-dioxolane, di-t-butyl peroxide, 2,5-dimethylhexyne-2,5-di-t-butylperoxide, 3,3,6,6,9,9-hexamethyl 1,2,4,5-tetraoxa cyclononane, p-menthane hydroperoxide, pinane hydroperoxide, diisopropylbenzene mono-α-hydroperoxide, cumene hydroperoxide or t-butyl hydroperoxide.

These compounds are commercially available.

If more than one radical source is used, a mixture of substitution patterns is obtainable.

The radical source is preferably present in an amount of from 0.01 mol-% to 30 mol-%, more preferred in an amount of from 0.1 mol-% to 20 mol-% and most preferred in an amount of from 0.5 mol-% to 10 mol-% based on the monomer or monomer mixture.

Preferably the nitroxyl compound is present in an amount of from 0.01 mol-% to 20 mol-%, more preferably in an amount of from 0.01 mol-% to 10 mol-% and most preferred in an amount of from 0.05 mol-% to 10 mol-% based on the monomer or monomer mixture.

The molar ratio of the radical source to the compound of formulae Ib, IIb or IIIb may be from 1:10 to 10:1, preferably from 1:5 to 5:1 and more preferably from 1:2 to 2:1.

Still another subject of the present invention is a process for preparing an oligomer, a cooligomer, a polymer or a copolymer (block or random) by free radical polymerization of at least one ethylenically unsaturated monomer/oligomer, which comprises subjecting the above composition to heat or actinic radiation.

The composition is preferably subjected to heat from 90° C. to 160° C.

A further subject of the invention is a compound of formula Ib or IIb

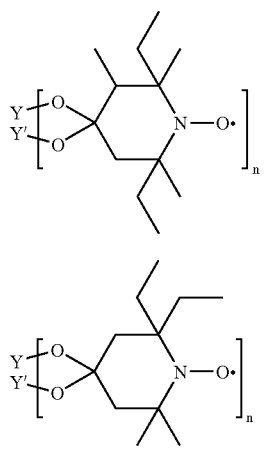

wherein n is 1 or 2;

if n is 1

Y and Y' are independently $C_1$-$C_{12}$alkyl, $C_3$-$C_{12}$alkenyl, $C_3$-$C_{12}$alkinyl, $C_5$-$C_8$cycloalkyl, phenyl, naphthyl, $C_7$-$C_9$phenylalkyl; or Y and Y' together form one of the bivalent groups —C($R_1$)($R_2$)—CH($R_3$)—, CH($R_1$)—$CH_2$—C($R_2$)($R_3$)—, —CH($R_2$)—$CH_2$—C($R_1$)($R_3$)—, —$CH_2$—C($R_1$)($R_2$)—CH($R_3$)—, o-phenylene, 1,2-cyclohexyliden, —$CH_2$—CH=CH—$CH_2$— or

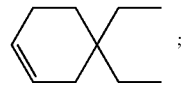

wherein $R_1$ is hydrogen, $C_1$-$C_{12}$alkyl, COOH, COO—($C_1$-$C_{12}$)alkyl or $CH_2OR_4$;

$R_2$ and $R_3$ are independently hydrogen, methyl ethyl, COOH or COO—($C_1$-$C_{12}$)alkyl;

$R_4$ is hydrogen, $C_1$-$C_{12}$alkyl, benzyl, or a monovalent acyl residue derived from an aliphatic, cycloaliphatic or aromatic monocarboxylic acid having up to 18 carbon atoms;

if n is 2

Y and Y' together form one of the tetravalent groups

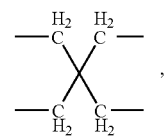

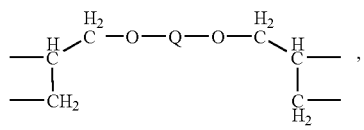

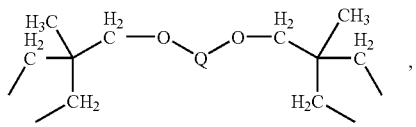

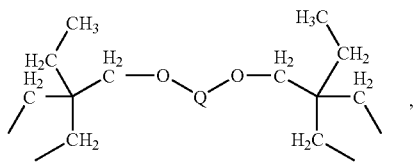

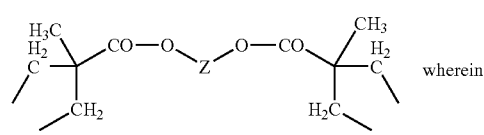

Q is a bisacyl residue which is derived from a $C_2$-$C_{12}$dicarboxylic acid or $C_1$-$C_{12}$alkylene; and Z is $C_1$-$C_{12}$alkylene; with the proviso that compounds D, E, F, G, H (D) 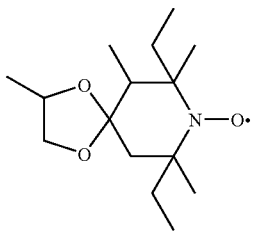

(E) 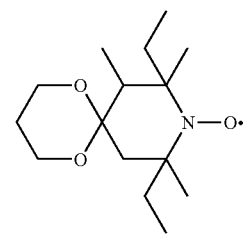

(F) 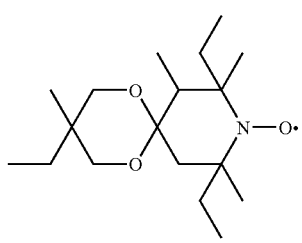

(G) 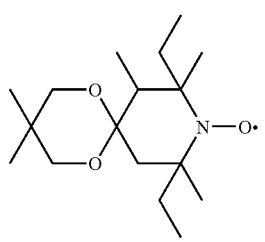

(H) 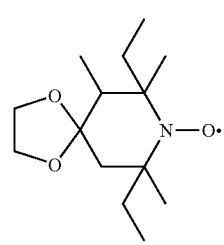

are excluded.

Yet another subject of the invention is a polymer or oligomer, having attached at least one oxyamine group derived from formula Ia, IIa or IIIa.

The polymers or oligomers can also be termed macroinitiators. They can be used to start polymerization for example with a second monomer which then results in the formation of a block copolymer as already described above.

Further subjects of the invention are the use of a compound of formulae Ia, IIa or IIIa for the polymerization of ethylenically unsaturated monomers and the use of a compound of formulae Ib or IIb together with a source of free radicals for the polymerization of an ethylenically unsaturated monomer.

Definitions and preferences for the various substituents have already been mentioned. They apply also for the other subjects of the invention including the preferences and the individual compounds.

The following examples illustrate the invention.

EXAMPLE A1

7,9-diethyl-6,7,9-trimethyl-1,4-dioxa-8-aza-spiro[4.5]decan-8-oxyl (Table 4, compound 10)

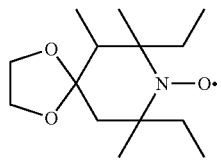

The compound is prepared according to U.S. Pat. No. 4,105,626 (example 5).

EXAMPLE A2

7,9-diethyl-2-hydroxymethyl-6,7,9-trimethyl-1,4-dioxa-8-aza-spiro[4.5]decan-8-oxyl (Table 4, compound 18)

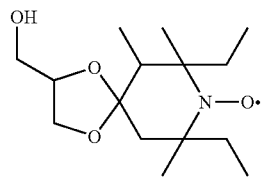

The title compound is prepared by oxidising 7,9-diethyl-2-hydroxymethyl-6,7,9-trimethyl-1,4-dioxa-8-aza-spiro[4.5]decan, prepared according to U.S. Pat. No. 4,105,626. A red oil is obtained. Elemental analysis for $C_{15}H_{28}NO_4$ calculated: C 62.91%, H 9.85%, N 4.89%; found: C 62.83%, H 9.83%, N 4.75%.

EXAMPLE A3

8,10-diethyl-3,3,7,8,10-pentamethyl-1,5-dioxa-9-aza-spiro[5.5]undecan-9-oxyl (Tabelle 2, compound 35)

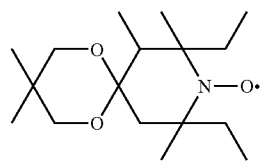

The title compound is prepared by oxidising 7,9-diethyl-2-hydroxymethyl-6,7,9-trimethyl-1,4-dioxa-8-aza-spiro[4.5]decan, prepared according to U.S. Pat. No. 4,105,626. A red oil is obtained. Elemental analysis for $C_{15}H_{28}NO_4$ calculated: C 68.42%, H 10.81, N 4.69; found: C 68.21%, H 10.66%, N 4.63%.

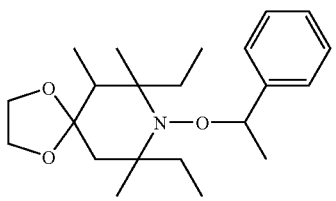

EXAMPLE A4

7,9-diethyl-6,7,9-trimethyl-8-(1-phenyl-ethoxy)-1,4-dioxa-8-aza-spiro[4.5]decane (Table 1, compound 10)

To a solution of 10.3 g (0.04 mol) 7,9-diethyl-6,7,9-trimethyl-1,4-dioxa-8-aza-spiro[4.5]decan-8-oxyl (Table 2, compound 10) in 40 ml ethylbenzene 8.3 ml (0.06 mol) 70% t-butyl-hydroperoxide in water and 0.7 ml of a catalyst solution (containing 13.44 g $CuCl_2$ and 4.24 g LiCl in 153 ml ethanol) are added. The mixture is stirred at 65° C. until it is colorless (approximately 90 minutes). After cooling to room temperature 25 ml water and 5 g $Na_2S_2O_5$ are added and the mixture is vigorously stirred for 10 minutes. The organic phase is separated, washed with $H_2O$ and the remaining ethylbenzene is evaporated. The residue chromatographically purified ($SiO_2$ hexane-ethylacetate (19:1)) and 10.3 g of the title compound is obtained as colorless oil. Elemental analysis for $C_{22}H_{35}NO_3$ calculated: C 73.09%, H 9.76%, N 3.87%; found: C 72.95%, H 9.79%, N 3.68%.

EXAMPLE A5

[7,9-diethyl-6,7,9-trimethyl-8-(1-phenyl-ethoxy)-1,4-dioxa-8-aza-spiro[4,5]dec-2-yl]-methanol (Table 1, compound 18)

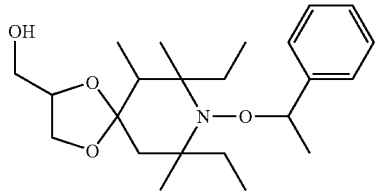

The title compound is prepared in analogy to example A4 from 7,9-diethyl-2-hydroxymethyl-6,7,9-trimethyl-1,4-dioxa-8-aza-spiro[4.5]decan-8-oxyl (Table 4, compound 18). Colorless oil, $^1$H-NMR($CDCl_3$, 300 MHz, d ppm): 7.4-7.1 m, (5 ArH), 4.74.55 m (1H), 4.3-3.55 m (5H), 2.1-0.5 m (26H).

EXAMPLE A6

8,10-diethyl-3,3,7,8,10-pentamethyl-9-(1-phenyl-ethoxy)-1,5-dioxa-9-aza-spiro[5.5]undecane (Table 1, compound 35)

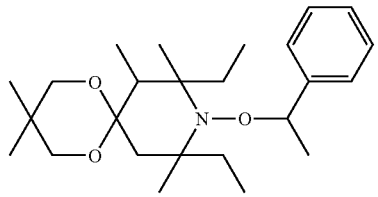

The title compound is prepared in analogy to example A4 from 8,10-diethyl-3,3,7,8,10-pentamethyl-1,5-dioxa-9-aza-spiro[5.5]undecan-9-oxyl (Table 4, compound 35). Colorless oil. Elemental analysis for $C_{25}H_{41}NO_3$ calculated: C 74.40%, H 10.24%, N 3.47%; found: C 74.19%, H 10.43%, N 3.43%.

EXAMPLE A7

3,8,10-triethyl-3-hydroxymethyl-7,8,10-trimethyl-1,5-dioxa-9-aza-spiro[5.5]undecan-9-oxyl (Table 4, compound 42)

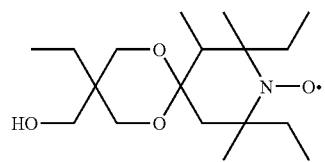

The title compound is prepared in analogy to Example A1 by oxidizing (3,8,10-triethyl-7,8,10-trimethyl-1,5-dioxa-9-aza-spiro[5.5]undec-3-yl)-methanol (prepared as described in U.S. Pat. No. 4,105,626) as a red oil. GC-MS: narrow bundle of 4 peaks (diastereomers) with $M^+$=328 ($C_{18}H_{34}NO_4$=328.48).

EXAMPLE A8 acetic acid 3,8,10-triethyl-7,8,10-trimethyl-1,5-dioxa-9-aza-spiro[5.5]undec-3-yl-methyl ester-9-oxyl (Table 4, compound 54)

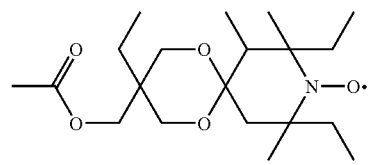

The title compound is prepared in analogy to Example A1 by oxidizing acetic acid 3,8,10-triethyl-7,8,10-trimethyl-1,5-dioxa-9-aza-spiro[5.5]undec-3-yl-methyl ester (prepared in analogy to U.S. Pat. No. 4,105,626, Example 4) as a red oil.

EXAMPLE A9 octadecanoic acid 3,8,10-triethyl-7,8,10-trimethyl-1,5-dioxa-9-aza-spiro[5.5]undec-3-ylmethyl ester-9-oxyl (Table 4, compound 55).

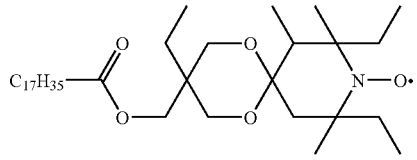

The title compound is prepared in analogy to Example 1 by oxidizing octadecanoic acid 3,8,10-triethyl-7,8,10-trimethyl-1,5-dioxa-9-aza-spiro[5.5]undec-3-yl-methyl ester (prepared in analogy to U.S. Pat. No. 4,105,626, Example 4) as a red oil. MS (CI): MH$^+$=595 (C$_{36}$H$_{68}$NO$_5$=594.95).

EXAMPLE A10 acetic acid 7,9-diethyl-6,7,9-trimethyl-1,4-dioxa-8-aza-spiro[4.5]dec-2-yl-methyl ester-8-oxyl (Table 4, compound 19)

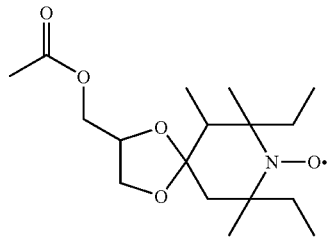

The title compound is prepared in analogy to Example A1 by oxidizing acetic acid 7,9-diethyl-6,7,9-trimethyl-1,4-dioxa-8-aza-spiro[4.5]dec-2-yl-methyl ester (prepared as described in U.S. Pat. No. 4,105,626, Example 4) as a red oil. GC-MS: narrow bundle of 6 peaks (diastereomers) with M$^+$=328 (C$_{17}$H$_{30}$NO$_5$=328.43).

EXAMPLE A11

2-(8,10-diethyl-3,3,7,8,10-pentamethyl-1,5-dioxa-9-aza-spiro[5.5]undec-9-yloxy)-propionic acid 2-hydroxy-ethyl ester (Table 1, compound 54)

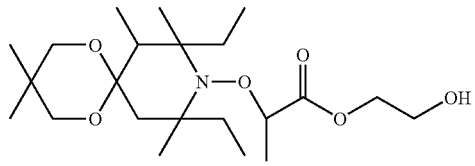

To a stirred mixture of 89.54 g (0.3 mol) 8,10-diethyl-3,3,7,8,10-pentamethyl-1,5-dioxa-9-aza-spiro[5.5]undecan-9-oxyl (Tab. 4, Nr. 35), 43.04 (0.3 mol) copper (I) bromide, 19.06 (0.3 mol) copper powder and 103.9 g (0.6 mol) pentamethyl-ethylene-triamine in 500 ml toluene are added dropwise within 30 minutes and under nitrogen 59.1 g (0.3 mol) 2-bromopropionic acid-2-hydroxyethylester. The mixture is stirred at rt for 17 h and then filtered. The filtrate is washed with water (3×500 ml) and then with a solution of EDTA (300 ml, 1%). The organic layer is dried over Na$_2$SO$_4$ and then evaporated to afford 122.8 g (98.5%) of the title compound as a slightly yellow oil.

$^1$H-NMR(CDCl$_3$, 300 MHz, d ppm): 4.45-4.26 m, (1H), 4.25-4.23 m (2H), 3.85 bs m (2H), 3.71-0.72 (36H).

B) Polymerizations with n-butylacrylate using Compounds of Formulae Ia, IIa or IIIa as initiators/regulators General Remarks:

Solvents and monomers are distilled over a Vigreux column under argon atmosphere or under vacuum, shortly before being used.

To remove oxygen all polymerization reaction mixtures are flushed before polymerization with argon and evacuated under vaccum applying a freeze-thaw cycle. The reaction mixtures are then polymerized under argon atmosphere.

At the start of the polymerization reaction, all starting materials are homogeneously dissolved.

Conversion is determined by removing unreacted monomers from the polymer at 80° C. and 0.002 torr for 30 minutes, weighing the remaining polymer and subtract the weight of the initiator.

Characterization of the polymers is carried out by MALDI-MS (Matrix Assisted Laser Desorption Ionization Mass Spectrometry) and/or GPC (Gel Permeation Chromatography).

MALDI-MS: Measurements are performed on a linear TOF (Time Of Flight) MALDI-MS LDI-1700 Linear Scientific Inc., Reno, USA. The matrix is 2,5-dihydroxybenzoic acid and the laser wavelength is 337 nm.

GPC: Is performed using RHEOS 4000 of FLUX INSTRUMENTS. Tetrahydrofurane (THF) is used as a solvent and is pumped at 1 ml/min. Two chromatography columns are put in series: type Pigel 5 μm mixed-C of POLYMER INSTRUMENTS, Shropshire, UK. Measurements are performed at 40° C. The columns are calibrated with low polydispersity polystyrenes having Mn from 200 to 2 000 000 Dalton. Detection is carried out using a RI-Detector ERC-7515A of ERCATECH AG at 30° C.

EXAMPLE B1

Polymerization of n-butylacrylate with compound 10, Table 1 (example A4) at 145° C.

In a 50 ml three neck flask, equipped with thermometer, cooler and magnetic stirrer, 644 mg (1.78 mmol) of compound 10, Table 1 and 15 g (117 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 11.1 g (74%) of the initial monomer have reacted. A clear yellow viscous fluid is obtained. Mn=6460, Mw=8280, PD=1.28

EXAMPLE B2

Polymerization of n-butylacrylate with compound 35, Table 1 (example A6) at 145° C.

In a 50 ml three neck flask, equipped with thermometer, cooler and magnetic stirrer, 718 mg (1.78 mmol) of compound 35, Table 1 and 15 g (117 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 12.3 g (82%) of the initial monomer have reacted. A clear yellow viscous fluid is obtained. Mn=6630, Mw=8450, PD=1.27

EXAMPLE B3

Polymerization of n-butylacrylate with compound 18, Table 1 (example A5) at 145° C.

In a 50 ml three neck flask, equipped with thermometer, cooler and magnetic stirrer, 679 mg (1.78 mmol) of compound 18, Table 1 and 15 g (117 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 12.37 g (82.5%) of the initial monomer have reacted. A clear yellow viscous fluid is obtained. Mn=7000, Mw=9000, PD=1.29

EXAMPLE B4

Preparation of a block copolymer from n-butylacrylate and N,N-dimethylaminoethylacrylate (DMAEA) using compound 10, Table 1

1) Preparation of Poly-n-butylacrylate

In a 50 ml three neck flask, equipped with thermometer, cooler and magnetic stirrer, 644 mg (1.78 mmol) of compound 10, Table 1 and 15 g (117 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 11.1 g (74%) of the initial monomer have reacted. A yellow viscous fluid is obtained.

Mn=5700, Mw=8050, PD=1.41

2) Preparation of a Block Copolymer with DMAEA

In a 50 ml three neck flask, equipped with thermometer, cooler and magnetic stirrer, 6.5 g of the above poly(n-butylacrylate and 6.5 g (45.5 mmol) N,N-dimethylaminoethylacrylate are mixed and degased. The clear solution obtained is heated under argon to 145° C. and polymerization is carried out during 3 h. The reaction mixture is then cooled to 70° C. The remaining monomer is removed by evaporation under high vacuum. 1. g (15%) of the monomer have reacted. A yellow/brownish viscous fluid is obtained.

Composition (NMR): 87 weight-% butylacrylate/13 weight-% N,N-dimethylaminoethylacrylate Mn=5700, Mw=8170, PD=1.43

EXAMPLE B5

Preparation of a block copolymer from n-butylacrylate and N,N-dimethylaminoethylacrylate (DMAEA) using compound 35, Table 1

1) Preparation of Poly-n-butylacrylate

In a 50 ml three neck flask, equipped with thermometer, cooler and magnetic stirrer, 718 mg (1.78 mmol) of compound 35, Table 1 and 15 g (117 mmol) of n-butylacrylate are mixed and degased. The clear solution obtained is heated under argon to 145° C. and polymerization is carried out during 5 h. The reaction mixture is then cooled to 60° C. The remaining monomer is removed by evaporation under high vacuum. 12.3 g (82%) of the initial monomer have reacted. A clear yellow viscous fluid is obtained.

Mn=6170, Mw=8300, PD=1.34

2) Preparation of a Block Copolymer with DMAEA

In a 50 ml three neck flask, equipped with thermometer, cooler and magnetic stirrer, 6.5 g of the above poly(n-butylacrylate and 5 g (35 mmol) N,N-dimethylaminoethylacrylate are mixed and degased. The clear solution obtained is heated under argon to 145° C. and polymerization is carried out during 3 h. The reaction mixture is then cooled to 70° C. The remaining monomer is removed by evaporation under high vacuum. 1. g (22%) of the monomer have reacted. A yellow/brownish viscous fluid is obtained.

Composition (NMR): 82 weight-% butylacrylate/18 weight-% N,N-dimethylaminoethylacrylate Mn=5700, Mw=8350, PD=1.46

C) Polymerizations with Styrene Using Compounds of Formulae Ia, IIa or IIIa as Initiators/Regulators In an evacuated Schlenk tube, flushed with Argon and equipped with magnetic stirrer, the amount of nitroxylether given in Table 6 is added to 50 mol freshly distilled n-styrene under an Argon atmosphere. The Schlenk tube is closed and the remaining oxygen is removed in two freeze thaw cycles with liquid nitrogen. The tube is filled with Argon and heated to the temperatures given in Table 6 for 6 hours with stirring. The remaining monomer is removed under vacuum at room temperature. Drying is continued until constant weight of the residue. Molecular weight and distribution are determined using gel permeation chromatography with tetrahydrofurane and calibrated with polystyrene standards. The results are given in Table 6.

TABLE 6

| Exp. No. | Temp (° C.) | Amount of regulator | Conversion (%) | $M_n$ (GPC) | $M_w$ (GPC) | $M_w/M_n$ |
|---|---|---|---|---|---|---|
| C0 | 130 | 1 mol % | 82 | 7600 | 9500 | 1.24 |
| C1 | 130 | 0.1 mol % | 81 | 42700 | 62800 | 1.47 |
| C2 | 120 | 1 mol % | 65 | 6200 | 7400 | 1.19 |
| C3 | 120 | 0.1 mol % | 55 | 35000 | 47900 | 1.37 |
| C4 | 110 | 1 mol % | 40 | 3800 | 4700 | 1.25 |
| C5 | 110 | 0.1 mol % | 28 | 22700 | 28300 | 1.25 |
| C6 | 100 | 1 mol % | 20 | 1700 | 2800 | 1.65 |
| C7 | 100 | 0.1 mol % | 15 | 13100 | 17800 | 1.36 |

1 mol % corresponds to $8.72 \times 10^{-2}$ mol NOR/I styrene, 0.1 mol % corresponds to $8.72 \times 10^{-3}$ mol NOR/I styrene.

Initiator/regulator is compound 35, Table 1

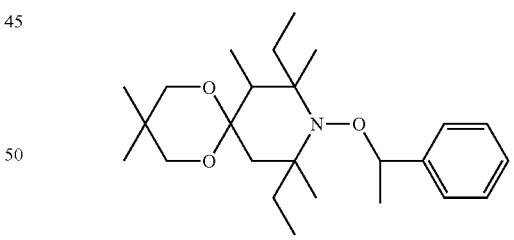

Polymerizations with Styrene Using Compounds of Formulae Ib, IIb and Dibenzovylperoxide (BPO) as Regulators/Initiators In an evacuated Schlenk tube, flushed with argon and equipped with magnetic stirrer, the amount of nitroxyl and BPO given in Table 7 is added to 50 mol freshly distilled n-styrene under an argon atmosphere. The Schlenk tube is closed and the remaining oxygen is removed in two freeze thaw cycles with liquid nitrogen. The tube is filled with argon and heated to the temperatures given in Table 7 for 6 hours with stirring. The remaining monomer is removed under vacuum at room temperature. Drying is continued until constant weight of the residue. Molecular weight and distribution are determined using gel permeation chromatography with tetrahydrofurane and calibrated with polystyrene standards. The results are given in Table 7.

TABLE 7

| Exp. No. | Temp (°C.) | Concentrations | Yield (%) | $M_n$ (calc) | $M_n$ (GPC) | $M_w$ (GPC) | $M_w/M_n$ |
|---|---|---|---|---|---|---|---|
| C8 | 130 | [NO•] = $8.72 \times 10^{-2}$ mol/l<br>[BPO] = $6.7 \times 10^{-2}$ mol/l | 44 | 5100 | 5300 | 6600 | 1.24 |
| C9 | 130 | [NO•] = $8.72 \times 10^{-2}$ mol/l<br>[BPO] = $6.7 \times 10^{-2}$ mol/l | 47 | 5300 | 5400 | 7100 | 1.32 |
| C10 | 130 | [NO•] = $8.72 \times 10^{-3}$ mol/l<br>[BPO] = $6.7 \times 10^{-3}$ mol/l | 77 | 81000 | 39000 | 55900 | 1.43 |
| C11 | 120 | [NO•] = $8.72 \times 10^{-3}$ mol/l<br>[BPO] = $6.7 \times 10^{-3}$ mol/l | 43 | 45500 | 29400 | 38900 | 1.33 |

[BPO] = $6.7 \times 10^{-3}$ mol/l corresponds 0.077 mol % Initiator,
[BPO] = $6.7 \times 10^{-2}$ mol/l corresponds 0.77 mol % Initiator
[NO•] = $8.72 \times 10^{-3}$ mol/l corresponds 0.1 mol % NO Radical,
[NO•] = $8.72 \times 10^{-2}$ mol/l corresponds 1 mol % NO Radical The NO radical is compound 35, Table 4:

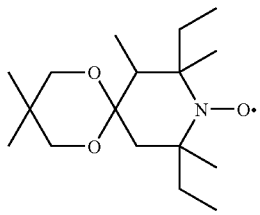

D. Blockcopolymerizations 20 grams of a styrene macroinitiator obtained by polymerizing styrene at 120° C. following the procedure as described in section C with a concentration of 0.05 mol % of compound 35 (Table 1) (molecular weight data see table) are dissolved in a glass autoclave in 1) 100 g styrene, 2) a mixture of 90 g of styrene and 30 g of acrylonitrile.

The solutions are degassed by argon purge for 30 minutes and subsequently heated in an oil bath at 110° C. for 6 hours. The polymer is obtained by precipitation into a 10 fold excess of methanol and dried in vacuo to remove unreacted monomer until constant weight. Molecular weights were determined by GPC as described in section C. The shift in molecular weight from D 0 to experiments D1 und D2 (Table 8) clearly indicates the formation of a block copolymer and confirms the capability of reinitiation of polymers synthesized using the instant compounds.

TABLE 8

| Exp.# | Comonomer(s) | Yield of added monomer(s) (%) | $M_n$ | $M_w$ | $M_w/M_n$ |
|---|---|---|---|---|---|
| D 0 |  |  | 60400 | 108600 | 1.80 |
| D 1 | Styrene | 45 | 96700 | 165600 | 1.71 |
| D 2 | Sty/AN | 50 | 143900 | 258700 | 1.80 |

This invention claimed is:

1. A polymerizable composition, comprising
   a) at least one ethylenically unsaturated monomer or oligomer selected from the group consisting of ethylene, propylene, n-butylene, i-butylene, styrene, substituted styrene, conjugated dienes, acrolein, vinyl acetate, vinylpyrrolidone, vinylimidazole, maleic anhydride, (alkyl)acrylic acidanhydrides, (alkyl)acrylic acid salts, (alkyl)acrylic esters, (meth)acrylonitriles, (alkyl) acrylamides, vinyl halides and vinylidene halides and
   b) a compound of formula Ia, IIa or IIIa

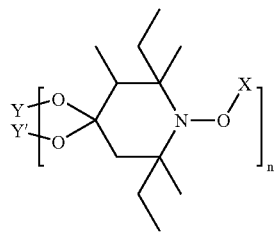

(Ia)

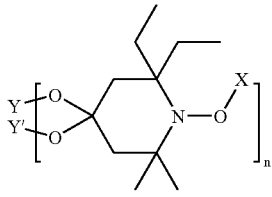

(IIa)

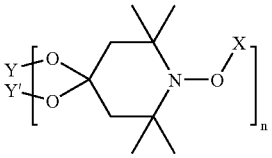

(IIIa)

wherein
X is $CH_3CH$-phenyl;
n is 1
Y and Y' are independently $C_1$-$C_{12}$alkyl, $C_3$-$C_{12}$alkenyl, phenyl or benzyl; or
Y and Y' together form one of the bivalent groups —C($R_1$)($R_2$)—CH($R_3$)—, CH($R_1$)—$CH_2$—C($R_2$)($R_3$)—, —CH($R_2$)—$CH_2$—C($R_1$)($R_3$)— or —$CH_2$—C($R_1$)($R_2$)—CH($R_3$)— wherein
$R_1$ is hydrogen, $C_1$-$C_{12}$alkyl, COO—($C_1$-$C_{12}$)alkyl or $CH_2OR_4$;
$R_2$ and $R_3$ are independently hydrogen, methyl, ethyl, or COO—($C_1$-$C_{12}$)alkyl; and
$R_4$ is hydrogen, $C_1$-$C_{12}$alkyl, benzyl, or a monovalent acyl residue derived from an aliphatic, cycloaliphatic or aromatic monocarboxylic acid having up to 12 carbon atoms.

2. A polymerizable composition according to claim 1 wherein the compound of component b) is of formula Ia or IIa.

3. A polymerizable composition according to claim 1 wherein the compound of formula Ia or IIa is 1.) 2,6-Diethyl-4,4-dimethoxy-2,3,6-trimethyl-1-(1-phenyl-ethoxy)-piperidine
2.) 4,4-Diethoxy-2,6-diethyl-2,3,6-trimethyl-1-(1-phenyl-ethoxy)-piperidine
3.) 2,6-Diethyl-2,3,6-trimethyl-1-(1-phenyl-ethoxy)-4,4-dipropoxy-piperidine
4.) 4,4-Dibutoxy-2,6-diethyl-2,3,6-trimethyl-1-(1-phenyl-ethoxy)-piperidine
5.) 2,6-Diethyl-4,4-diisobutoxy-2,3,6-trimethyl-1-(1-phenyl-ethoxy)-piperidine
6.) 2,6-Diethyl-2,3,6-trimethyl-4,4-bis-octyloxy-1-(1-phenyl-ethoxy)-piperidine
7.) 4,4-Bis-allyloxy-2,6-diethyl-2,3,6-trimethyl-1-(1-phenyl-ethoxy)-piperidine
9.) 4,4-Bis-benzyloxy-2,6-diethyl-2,3,6-trimethyl-1-(1-phenyl-ethoxy)-piperidine
10.) 7,9-Diethyl-6,7,9-trimethyl-8-(1-phenyl-ethoxy)-1,4-dioxa-8-aza-spiro[4.5]decane
11.) 7,9-Diethyl-2,6,7,9-tetramethyl-8-(1-phenyl-ethoxy)-1,4-dioxa-8-aza-spiro[4.5]decane
12.) 2,7,9-Triethyl-6,7,9-trimethyl-8-(1-phenyl-ethoxy)-1,4-dioxa-8-aza-spiro[4.5]decane
13.) 7,9-Diethyl-6,7,9-trimethyl-8-(1-phenyl-ethoxy)-2-propyl-1,4-dioxa-8-aza-spiro[4.5]decane
14.) 2-Butyl-7,9-diethyl-6,7,9-trimethyl-8-(1-phenyl-ethoxy)-1,4-dioxa-8-aza-spiro[4.5]decane
15.) 7,9-Diethyl-6,7,9-trimethyl-2-octyl-8-(1-phenyl-ethoxy)-1,4-dioxa-8-aza-spiro[4.5]decane
16.) 2-Decyl-7,9-diethyl-6,7,9-trimethyl-8-(1-phenyl-ethoxy)-1,4-dioxa-8-aza-spiro[4.5]decane
17.) 2-Dodecyl-7,9-diethyl-6,7,9-trimethyl-8-(1-phenyl-ethoxy)-1,4-dioxa-8-aza-spiro[4.5]decane
18.) [7,9-Diethyl-6,7,9-trimethyl-8-(1-phenyl-ethoxy)-1,4-dioxa-8-aza-spiro[4.5]dec-2-yl]-methanol
19.) Acetic acid 7,9-diethyl-8-hydroxy-6,7,9-trimethyl-1,4-dioxa-8-aza-spiro[4.5]dec-2-ylmethyl ester; compound with isopropyl-benzene
20.) Octadecanoic acid 7,9-diethyl-6,7,9-trimethyl-8-(1-phenyl-ethoxy)-1,4-dioxa-8-aza-spiro[4.5]dec-2-ylmethyl ester
21.) Benzoic acid 7,9-diethyl-8-hydroxy-6,7,9-trimethyl-1,4-dioxa-8-aza-spiro[4.5]dec-2-ylmethyl ester; compound with isopropyl-benzene
22.) 7,9-Diethyl-2-methoxymethyl-6,7,9-trimethyl-8-(1-phenyl-ethoxy)-1,4-dioxa-8-aza-spiro[4.5]decane
23.) 2-Cyclohexyloxymethyl-7,9-diethyl-6,7,9-trimethyl-8-(1-phenyl-ethoxy)-1,4-dioxa-8-aza-spiro[4.5]decane
24.) 2-Benzyloxymethyl-7,9-diethyl-6,7,9-trimethyl-8-(1-phenyl-ethoxy)-1,4-dioxa-8-aza-spiro[4.5]decane
25.) Octanedioic acid bis-[7,9-diethyl-6,7,9-trimethyl-8-(1-phenyl-ethoxy)-1,4-dioxa-8-aza-spiro[4.5]dec-2-ylmethyl]ester
26.) Terephthalic acid bis-[7,9-diethyl-6,7,9-trimethyl-8-(1-phenyl-ethoxy)-1,4-dioxa-8-aza-spiro[4.5]dec-2-ylmethyl]ester
27.) 1,4-Bis-{[7,9-diethyl-6,7,9-trimethyl-8-(1-phenyl-ethoxy)-1,4-dioxa-8-aza-spiro[4.5]dec-2-yl]-methyloxy}-butane
28.) 7,9-Diethyl-2,2,6,7,9-pentamethyl-8-(1-phenyl-ethoxy)-1,4-dioxa-8-aza-spiro[4.5]decane
29.) 7,9-Diethyl-2,3,6,7,9-pentamethyl-8-(1-phenyl-ethoxy)-1,4-dioxa-8-aza-spiro[4.5]decane
30.) 2,3-Benzo-7,9-diethyl-6,7,9-trimethyl-8-(1-phenyl-ethoxy)-1,4-dioxa-8-aza-spiro[4.5]decane
31.) 2,3-Cyclohexano-7,9-diethyl-6,7,9-trimethyl-8-(1-phenyl-ethoxy)-1,4-dioxa-8-aza-spiro[4.5]decane
32.) 7,9-Diethyl-6,7,9-trimethyl-8-(1-phenyl-ethoxy)-1,4-dioxa-8-aza-spiro[4.5]decane-2,3-dicarboxylic acid
33.) 7,9-Diethyl-6,7,9-trimethyl-8-(1-phenyl-ethoxy)-1,4-dioxa-8-aza-spiro[4.5]decane-2,3-dicarboxylic acid dimethyl ester
34.) 8,10-Diethyl-7,8,10-trimethyl-9-(1-phenyl-ethoxy)-1,5-dioxa-9-aza-spiro[5.5]undecane
35.) 8,10-Diethyl-3,3,7,8,10-pentamethyl-9-(1-phenyl-ethoxy)-1,5-dioxa-9-aza-spiro[5.5]undecane
36.) 3,8,10-Triethyl-3,7,8,10-tetramethyl-9-(1-phenyl-ethoxy)-1,5-dioxa-9-aza-spiro[5.5]undecane
37.) 3,3,8,10-Tetraethyl-7,8,10-trimethyl-9-(1-phenyl-ethoxy)-1,5-dioxa-9-aza-spiro[5.5]undecane
38.) 8,10-Diethyl-3,7,8,10-tetramethyl-9-(1-phenyl-ethoxy)-3-propyl-1,5-dioxa-9-aza-spiro-[5.5]undecane
39.) 3-Butyl-3,8,10-triethyl-7,8,10-trimethyl-9-(1-phenyl-ethoxy)-1,5-dioxa-9-aza-spiro[5.5]undecane
40.) 2,4-Diethyl-1,2,4-trimethyl-3-(1-phenyl-ethoxy)-7,16-dioxa-3-aza-dispiro[5.2.5.2]hexadec-11-ene
41.) [8,10-Diethyl-3,7,8,10-tetramethyl-9-(1-phenyl-ethoxy)-1,5-dioxa-9-aza-spiro[5.5]undec-3-yl]methanol
42.) [3,8,10-Triethyl-7,8,10-trimethyl-9-(1-phenyl-ethoxy)-1,5-dioxa-9-aza-spiro[5.5]undec-3-yl]-methanol
43.) 8,10-Diethyl-3-methoxymethyl-3,7,8,10-tetramethyl-9-(1-phenyl-ethoxy)-1,5-dioxa-9-aza-spiro[5.5]undecane
44.) 3-Cyclohexyloxymethyl-8,10-diethyl-3,7,8,10-tetramethyl-9-(1-phenyl-ethoxy)-1,5-dioxa-9-aza-spiro[5.5]undecane
45.) 3-Benzyloxymethyl-8,10-diethyl-3,7,8,10-tetramethyl-9-(1-phenyl-ethoxy)-1,5-dioxa-9-aza-spiro[5.5]undecane
46.) Acetic acid 8,10-diethyl-3,7,8,10-tetramethyl-9-(1-phenyl-ethoxy)-1,5-dioxa-9-aza-spiro[5.5]undec-3-yl-methyl ester
47.) Octanedioic acid bis-[8,10-diethyl-3,7,8,10-tetramethyl-9-(1-phenyl-ethoxy)-1,5-dioxa-9-aza-spiro[5.5]undec-3-ylmethyl]ester
48.) 1,6-Bis-{3,8,10-triethyl-7,8,10-trimethyl-9-(1-phenyl-ethoxy)-1,5-dioxa-9-aza-spiro[5.5]undec-3-methyloxy}-hexane
49.) 8,10-Diethyl-3,7,8,10-tetramethyl-9-(1-phenyl-ethoxy)-1,5-dioxa-9-aza-spiro[5.5]undecane-3-carboxylic acid
50.) 8,10-Diethyl-3,7,8,10-tetramethyl-9-(1-phenyl-ethoxy)-1,5-dioxa-9-aza-spiro[5.5]undecane-3-carboxylic acid methyl ester
51.) 8,10-Diethyl-7,8,10-trimethyl-9-(1-phenyl-ethoxy)-1,5-dioxa-9-aza-spiro[5.5]undecane-3,3-dicarboxylic acid diethyl ester
52.) 3,3-Bisspiro-{8,10-diethyl-7,8,10-trimethyl-9-(1-phenyl-ethoxy)-1,5-dioxa-9-aza-spiro[5.5]undecane}
53.) 2,4-Diethyl-1,2,4-trimethyl-3-(1-phenyl-ethoxy)-7,12-dioxa-3-aza-spiro[5.6]dodec-9-ene
54.) 2,2-Diethyl-4,4-dimethoxy-6,6-dimethyl-1-(1-phenyl-ethoxy)-piperidine
55.) 4,4-Diethoxy-2,2-diethyl-6,6-dimethyl-1-(1-phenyl-ethoxy)-piperidine
56.) 2,2-Diethyl-6,6-dimethyl-1-(1-phenyl-ethoxy)-4,4-dipropoxy-piperidine
57.) 4,4-Dibutoxy-2,2-diethyl-6,6-dimethyl-1-(1-phenyl-ethoxy)-piperidine 58.) 2,2-Diethyl-4,4-diisobutoxy-6,6-dimethyl-1-(1-phenyl-ethoxy)-piperidine
59.) 2,2-Diethyl-6,6-dimethyl-4,4-bis-octyloxy-1-(1-phenyl-ethoxy)-piperidine
60.) 4,4-Bis-allyloxy-2,2-diethyl-6,6-dimethyl-1-(1-phenyl-ethoxy)-piperidine
62.) 4,4-Bis-benzyloxy-2,2-diethyl-6,6-dimethyl-1-(1-phenyl-ethoxy)-piperidine
63.) 7,7-Diethyl-9,9-dimethyl-8-(1-phenyl-ethoxy)-1,4-dioxa-8-aza-spiro[4.5]decane
64.) 7,7-Diethyl-2,9,9-trimethyl-8-(1-phenyl-ethoxy)-1,4-dioxa-8-aza-spiro[4.5]decane
65.) 2,7,7-Triethyl-9,9-dimethyl-8-(1-phenyl-ethoxy)-1,4-dioxa-8-aza-spiro[4.5]decane
66.) 7,7-Diethyl-9,9-dimethyl-8-(1-phenyl-ethoxy)-2-propyl-1,4-dioxa-8-aza-spiro[4.5]decane
67.) 2-Butyl-7,7-diethyl-9,9-dimethyl-8-(1-phenyl-ethoxy)-1,4-dioxa-8-aza-spiro[4.5]decane
68.) 7,7-Diethyl-9,9-dimethyl-2-octyl-8-(1-phenyl-ethoxy)-1,4-dioxa-8-aza-spiro[4.5]decane
69.) 2-Decyl-7,7-diethyl-9,9-dimethyl-8-(1-phenyl-ethoxy)-1,4-dioxa-8-aza-spiro[4.5]decane
70.) 2-Dodecyl-7,7-diethyl-9,9-dimethyl-8-(1-phenyl-ethoxy)-1,4-dioxa-8-aza-spiro[4.5]decane
71.) [7,7-Diethyl-9,9-dimethyl-8-(1-phenyl-ethoxy)-1,4-dioxa-8-aza-spiro[4.5]dec-2-yl]-methanol
72.) Acetic acid 7,7-diethyl-8-hydroxy-9,9-dimethyl-1,4-dioxa-8-aza-spiro[4.5]dec-2-ylmethyl ester; compound with isopropyl-benzene
73.) Octadecanoic acid 7,7-diethyl-9,9-dimethyl-8-(1-phenyl-ethoxy)-1,4-dioxa-8-aza-spiro[4.5]dec-2-ylmethyl ester
74.) Benzoic acid 7,7-diethyl-8-hydroxy-9,9-dimethyl-1,4-dioxa-8-aza-spiro[4.5]dec-2-ylmethyl ester; compound with isopropyl-benzene
75.) 7,7-Diethyl-2-methoxymethyl-9,9-dimethyl-8-(1-phenyl-ethoxy)-1,4-dioxa-8-aza-spiro[4.5]decane
76.) 2-Cyclohexyloxymethyl-7,7-diethyl-9,9-dimethyl-8-(1-phenyl-ethoxy)-1,4-dioxa-8-aza-spiro-[4.5]decane
77.) 2-Benzyloxymethyl-7,7-diethyl-9,9-dimethyl-8-(1-phenyl-ethoxy)-1,4-dioxa-8-aza-spiro[4.5]decane
78.) Octanedioic acid bis-[7,7-diethyl-9,9-dimethyl-8-(1-phenyl-ethoxy)-1,4-dioxa-8-aza-spiro[4.5]dec-2-ylmethyl]ester
79.) Terephthalic acid bis-[7,7-diethyl-9,9-dimethyl-8-(1-phenyl-ethoxy)-1,4-dioxa-8-aza-spiro[4.5]dec-2-ylmethyl]ester
80.) 1,4-Bis-{[7,7-Diethyl-9,9-dimethyl-8-(1-phenyl-ethoxy)-1,4-dioxa-8-aza-spiro[4.5]dec-2-yl]-methyloxy}-butane
81.) 7,7-Diethyl-2,2,9,9-tetramethyl-8-(1-phenyl-ethoxy)-1,4-dioxa-8-aza-spiro[4.5]decane
82.) 7,7-Diethyl-2,3,9,9-tetramethyl-8-(1-phenyl-ethoxy)-1,4-dioxa-8-aza-spiro[4.5]decane
83.) 2,3-Benzo-7,7-diethyl-9,9-dimethyl-8-(1-phenyl-ethoxy)-1,4-dioxa-8-aza-spiro[4.5]decane
84.) 2,3-Cyclohexano-7,7-diethyl-9,9-dimethyl-8-(1-phenyl-ethoxy)-1,4-dioxa-8-aza-spiro[4.5]decane
85.) 7,7-Diethyl-9,9-dimethyl-8-(1-phenyl-ethoxy)-1,4-dioxa-8-aza-spiro[4.5]decane-2,3-dicarboxylic acid
86.) 7,7-Diethyl-9,9-dimethyl-8-(1-phenyl-ethoxy)-1,4-dioxa-8-aza-spiro[4.5]decane-2,3-dicarboxylic acid dimethyl ester
87.) 8,8-Diethyl-10,10-dimethyl-9-(1-phenyl-ethoxy)-1,5-dioxa-9-aza-spiro[5.5]undecane
88.) 8,8-Diethyl-3,3,10,10-tetramethyl-9-(1-phenyl-ethoxy)-1,5-dioxa-9-aza-spiro[5.5]undecane
89.) 3,8,8-Triethyl-3,10,10-trimethyl-9-(1-phenyl-ethoxy)-1,5-dioxa-9-aza-spiro[5.5]undecane
90.) 3,3,8,8-Tetraethyl-10,10-dimethyl-9-(1-phenyl-ethoxy)-1,5-dioxa-9-aza-spiro[5.5]undecane
91.) 8,8-Diethyl-3,10,10-trimethyl-9-(1-phenyl-ethoxy)-3-propyl-1,5-dioxa-9-aza-spiro[5.5]undecane
92.) 3-Butyl-3,8,8-triethyl-10,10-dimethyl-9-(1-phenyl-ethoxy)-1,5-dioxa-9-aza-spiro[5.5]undecane
93.) 2,2-Diethyl-4,4-dimethyl-3-(1-phenyl-ethoxy)-7,16-dioxa-3-aza-dispiro[5.2.5.2]hexadec-11-ene
94.) [8,8-Diethyl-3,10,10-trimethyl-9-(1-phenyl-ethoxy)-1,5-dioxa-9-aza-spiro[5.5]undec-3-yl]-methanol
95.) [3,8,8-Triethyl-10,10-dimethyl-9-(1-phenyl-ethoxy)-1,5-dioxa-9-aza-spiro[5.5]undec-3-yl]-methanol
96.) 8,8-Diethyl-3-methoxymethyl-3,10,10-trimethyl-9-(1-phenyl-ethoxy)-1,5-dioxa-9-aza-spiro[5.5]undecane
97.) 3-Cyclohexyloxymethyl-8,8-diethyl-3,10,10-trimethyl-9-(1-phenyl-ethoxy)-1,5-dioxa-9-aza-spiro[5.5]undecane
98.) 3-Benzyloxymethyl-8,8-diethyl-3,10,10-trimethyl-9-(1-phenyl-ethoxy)-1,5-dioxa-9-aza-spiro[5.5]undecane
99.) Acetic acid 8,8-diethyl-3,10,10-trimethyl-9-(1-phenyl-ethoxy)-1,5-dioxa-9-aza-spiro[5.5]undec-3-ylmethyl ester
100.) Octanedioic acid bis-[8,8-diethyl-3,10,10-trimethyl-9-(1-phenyl-ethoxy)-1,5-dioxa-9-aza-spiro[5.5]undec-3-ylmethyl]ester
101.) 1,6-Bis{[3,8,8-triethyl-10,10-dimethyl-9-(1-phenyl-ethoxy)-1,5-dioxa-9-aza-spiro[5.5]undec-3-yl]-methyloxy}-hexane
102.) 8,8-Diethyl-3,10,10-trimethyl-9-(1-phenyl-ethoxy)-1,5-dioxa-9-aza-spiro[5.5]undecane-3-carboxylic acid
103.) 8,8-Diethyl-3,10,10-trimethyl-9-(1-phenyl-ethoxy)-1,5-dioxa-9-aza-spiro[5.5]undecane-3-carboxylic acid methyl ester
104.) 8,8-Diethyl-10,10-dimethyl-9-(1-phenyl-ethoxy)-1,5-dioxa-9-aza-spiro[5.5]undecane-3,3-dicarboxylic acid diethyl ester
105.) 3,3-Bisspiro{8,8-diethyl-10,10-dimethyl-9-(1-phenyl-ethoxy)-1,5-dioxa-9-aza-spiro[5.5]undecane} or
106.) 2,2-Diethyl-4,4-dimethyl-3-(1-phenyl-ethoxy)-7,12-dioxa-3-aza-spiro[5.6]dodec-9-ene.

4. A composition according to claim 1 wherein the compound of formula Ia or IIa is 4,4-Dibutoxy-2,6-diethyl-2,3,6-trimethyl-1-(1-phenyl-ethoxy)-piperidine;

7,9-Diethyl-6,7,9-trimethyl-8-(1-phenyl-ethoxy)-1,4-dioxa-8-aza-spiro[4.5]decane;

7,9-Diethyl-2,6,7,9-tetramethyl-8-(1-phenyl-ethoxy)-1,4-dioxa-8-aza-spiro[4.5]decane;

[7,9-Diethyl-6,7,9-trimethyl-8-(1-phenyl-ethoxy)-1,4-dioxa-8-aza-spiro[4.5]dec-2-yl]-methanol;

8,10-Diethyl-7,8,10-trimethyl-9-(1-phenyl-ethoxy)-1,5-dioxa-9-aza-spiro[5.5]undecane;

8,10-Diethyl-3,3,7,8,10-pentamethyl-9-(1-phenyl-ethoxy)-1,5-dioxa-9-aza-spiro[5.5]undecane;

2,4-Diethyl-1,2,4-trimethyl-3-(1-phenyl-ethoxy)-7,16-dioxa-3-aza-dispiro[5.2.5.2]hexadec-11-ene;

[8,10-Diethyl-3,7,8,10-tetramethyl-9-(1-phenyl-ethoxy)-1,5-dioxa-9-aza-spiro[5.5]undec-3-yl]-methanol or 9-(Cyclohex-2-enyloxy)-8,10-diethyl-3,3,7,8,10-pentamethyl-1,5-dioxa-9-aza-spiro[5.5]undecane.

5. A composition according to claim 1, wherein the compound of formula Ia, IIa or IIIa is present in an amount of from 0.01 mol-% to 20 mol-% based on the at least one monomer or oligomer.

* * * * *